(12) United States Patent
Stoddart et al.

(10) Patent No.: US 12,074,314 B2
(45) Date of Patent: Aug. 27, 2024

(54) RECHARGEABLE ALUMINUM ORGANIC BATTERIES

(71) Applicants: Northwestern University, Evanston, IL (US); King Abdulaziz City for Science and Technology (KACST), Riyadh (SA); Seoul National University R&DB Foundation, Seoul (KR)

(72) Inventors: James Fraser Stoddart, Evanston, IL (US); Dong Jun Kim, Evanston, IL (US); Jang Wook Choi, Seoul (KR); Dong-Joo Yoo, Seoul (KR)

(73) Assignees: Northwestern University, Evanston, IL (US); King Abdulaziz City for Science and Technology (KACST), Riyadh (SA); Seoul National University R&DB Foundation, South (KR)

(*) Notice: Subject to any disclaimer, the term of this patent is extended or adjusted under 35 U.S.C. 154(b) by 864 days.

(21) Appl. No.: 17/261,490

(22) PCT Filed: Jul. 19, 2019

(86) PCT No.: PCT/US2019/042547
§ 371 (c)(1),
(2) Date: Jan. 19, 2021

(87) PCT Pub. No.: WO2020/018881
PCT Pub. Date: Jan. 23, 2020

(65) Prior Publication Data
US 2021/0242452 A1    Aug. 5, 2021

Related U.S. Application Data

(60) Provisional application No. 62/700,614, filed on Jul. 19, 2018.

(51) Int. Cl.
*H01M 4/36* (2006.01)
*C07C 49/563* (2006.01)
(Continued)

(52) U.S. Cl.
CPC .......... *H01M 4/364* (2013.01); *C07C 49/563* (2013.01); *C07F 5/069* (2013.01); *H01M 4/38* (2013.01);
(Continued)

(58) Field of Classification Search
CPC ........ H01M 4/364; H01M 4/38; H01M 4/583; H01M 4/60; H01M 4/625; C07C 49/563; C07F 5/069
(Continued)

(56) References Cited

U.S. PATENT DOCUMENTS 8,338,027 B2   12/2012   Ohtsuka
9,843,070 B2   12/2017   Dai
(Continued)

FOREIGN PATENT DOCUMENTS

WO   WO-2017151653 A2 *   9/2017   ........... C07D 471/22

OTHER PUBLICATIONS

Wang, S., Yu, Z., Tu, J., Wang, J., Tian, D., Liu, Y., Jiao, S. (2016). A Novel Aluminum-Ion Battery: Al/AlCl3-[EMIm]Cl/Ni3S2@Graphene. Adv. Energy Mater., 6: 1600137. doi: 10.1002/aenm.201600137 (Year: 2016).*
(Continued)

*Primary Examiner* — James M Erwin
(74) *Attorney, Agent, or Firm* — Quarles & Brady LLP

(57) ABSTRACT

Disclosed herein are rechargeable aluminum organic batteries and active materials used therein. The cathodic materials
(Continued)

used herein comprise a macrocycle comprising a substituted or unsubstituted phenanthrenequinone unit and a graphite flake.

19 Claims, 32 Drawing Sheets

(51) Int. Cl.
| | |
|---|---|
| C07F 5/06 | (2006.01) |
| H01M 4/38 | (2006.01) |
| H01M 4/583 | (2010.01) |
| H01M 4/60 | (2006.01) |
| H01M 4/62 | (2006.01) |
| H01M 10/054 | (2010.01) |
| H01M 10/0566 | (2010.01) |

(52) U.S. Cl.
CPC ............. *H01M 4/583* (2013.01); *H01M 4/60* (2013.01); *H01M 4/625* (2013.01); *H01M 10/054* (2013.01); *H01M 10/0566* (2013.01); *C07C 2603/92* (2017.05); *H01M 2300/0025* (2013.01)

(58) Field of Classification Search
USPC .......................................................... 429/199
See application file for complete search history.

(56) References Cited

U.S. PATENT DOCUMENTS

| | | | | |
|---|---|---|---|---|
| 2015/0194665 | A1* | 7/2015 | Ohtsuka | H01M 4/9008 429/188 |
| 2016/0276669 | A1 | 9/2016 | Chen | |
| 2016/0301096 | A1* | 10/2016 | Zhamu | H01G 11/24 |
| 2017/0358815 | A1* | 12/2017 | Chang | H01M 4/582 |

OTHER PUBLICATIONS

Wu, Y, et al. "Quinone electrode materials for rechargeable lithium/sodium ion batteries." Advanced Energy Materials 7.24 (2017): 1700278.
Yang, H., et al. "An aluminum-sulfur battery with a fast kinetic response." Angewandte Chemie 130.7 (2018): 1916-1920.
Yoo D.-J., et al. Stable performance of aluminum metal battery by incorporating lithium ion chemistry. ChemElectroChem 4, 2345-2351 (2017).
Yu, X., et al. "Room-temperature aluminum-sulfur batteries with a lithium-ion-mediated ionic liquid electrolyte." Chem 4.3 (2018): 586-598.
Zhang J., et al. Metal-free phenanthrenequinone cyclotrimer as an effective heterogeneous catalyst. J. Am. Chem. Soc. 131, 11296-11297 (2009).
Zhang Z., et al. Discovery of a "bipolar charging" mechanism in the solid-state electrochemical process of a flexible metal-organic framework. Chem. Mater. 28, 1298-1303 (2016).
Angell, M., et al. "High Coulombic efficiency aluminum-ion battery using an AlCl3-urea ionic liquid analog electrolyte." Proceedings of the National Academy of Sciences 114.5 (2017): 834-839.
Armand M., et al. Building better batteries. Nature 451, 652-657 (2008).
Armand M., et al. Conjugated dicarboxylate anodes for Li-ion batteries. Nat. Mater. 8, 120-125 (2009).
Atwood D. A. Cationic group 13 complexes. Coord. Chem. Rev. 176, 407-430 (1998).
Aurbach D., et al. Prototype systems for rechargeable magnesium batteries. Nature 407, 724-727 (2000).
Barker P. E., et al. The reaction of aluminium trichloride with 9,10-phenanthrenequinone. J. Organomet. Chem. 208, C1-C2 (1981).

Buchanan R. M. et al. Tautomeric catecholate-semiquinone interconversion via metal-ligand electron-transfer—structural, spectral, and magnetic-properties of (3,5-di-tert-butylcatecholato)-(3,5-di-tert-butylsemiquinone)(bipyridyl) cobalt(III), a complex containing mixed-valence organic-ligands. J. Am. Chem. Soc. 102, 4951-4957 (1980).
Canepa P., et al. Odyssey of multivalent cathode materials: Open questions and future challenges. Chem. Rev. 117, 4287-4341 (2017).
Chaudhuri D., et al. Tuning the singlet triplet gap in metal-free phosphorescent p-conjugated polymers. Angew. Chem. Int. Ed. 49, 7714-7717 (2010).
Chen C. J., et al. Highly conductive, lightweight, low-tortuosity carbon frameworks as ultrathick 3D current collectors. Adv. Energy. Mater. 7, 1700595 (2017).
Chen, C.-Y., et al. "Rechargeable aluminum batteries utilizing a chloroaluminate inorganic ionic liquid electrolyte." Chemical Communications 54.33 (2018): 4164-4167.
Choi J. W. et al. Promise and reality of post-lithium-ion batteries with high energy densities. Nat. Rev. Mater. 1, 16013 (2016).
Chu S., et al. The path towards sustainable energy. Nat. Mater. 16, 16-22 (2017).
Ciszek J. W. & Tour J. M. Synthesis of ladder polyaromatics as new molecular device candidates. Tetrahedron Lett. 45, 2801-2803 (2004).
Connelly N. G. et al. Chemical redox agents for organometallic chemistry. Chem. Rev. 96, 877-910 (1996).
Dagorne S. et al. Synthesis, characterization, and applications of group 13 cationic compounds. Chem. Rev. 108, 4037-4071 (2008).
Dunn B., et al. Electrical energy storage for the grid: A battery of choices. Science 334, 928-935 (2011).
Elia G. A., et al. An overview and future perspectives of aluminum batteries. Adv. Mater. 28, 7564-7579 (2016).
Fang C., et al. A metal-organic compound as cathode material with superhigh capacity achieved by reversible cationic and anionic redox chemistry for high-energy sodium-ion batteries. Angew. Chem. Int. Ed. 129, 6897-6901 (2017).
Geim A. K. et al. The rise of graphene. Nat. Mater. 6, 183-191 (2007).
Goodenough J. B. et al. The Li-ion rechargeable battery: A perspective. J. Am. Chem. Soc. 135, 1167-1176 (2013).
Hassan F. M., et al. Evidence of covalent synergy in silicon-sulfur-graphene yielding highly efficient and long-life lithium-ion batteries. Nat. Commun. 6, 8597 (2015).
Hudak N. S. Chloroaluminate-doped conducting polymers as positive electrodes in rechargeable aluminum batteries. J. Phys. Chem. C 118, 5203-5215 (2014).
International Searching Authority. International Search Report and Written Opinion for application PCT/US2019/042547. Mailed on Oct. 10, 2019. 8 pages.
Jayaprakash N., et al. The rechargeable aluminum-ion battery. Chem. Commun. 47, 12610-12612 (2011).
Kaim W. Radical-forming electron-transfer reactions involving main-group organometallics. Acc. Chem. Res. 18, 160-166 (1985).
Kim D. J., et al. Redox-active macrocycles for organic rechargeable batteries. J. Am. Chem. Soc. 139, 6635-6643 (2017).
Kim Y. A., et al. Structure-property relationship of D-A type copolymers based on phenanthrene and naphthalene units for organic electronics. J Mater Chem C 5, 10332-10342 (2017).
Kim, D. J., et al. "Rechargeable aluminium organic batteries." Nature Energy 4.1 (2019): 51-59. Originally published Dec. 3, 2018.
Kitada, A., et al. "AlCl3-dissolved diglyme as electrolyte for room-temperature aluminum electrodeposition." Electrochemistry 82.11 (2014): 946-948.
Klimov E. S., et al. Electron-spin-resonance spectra of chelate complexes of 1,2-naphthoquinone and 9,10-phenanthrenequinone with halides of group-III elements. Russ. Chem. Bull. 30, 1664-1666 (1981).
Koten G. V., et al. Stable 1,4-diaza-1,3-butadiene(a-diimine)-zinc and -aluminium radicals formed in single electron transfer reactions: Their consequences for organic syntheses. J. Organomet. Chem. 250, 49-61 (1983).
Kravchyk K. V., et al. Efficient aluminum chloride-natural graphite battery. Chem. Mater. 29, 4484-4492 (2017).

(56) References Cited

OTHER PUBLICATIONS

Lee J. H., et al. Restacking-inhibited 3d reduced graphene oxide for high performance supercapacitor electrodes. Acs Nano 7, 9366-9374 (2013).

Lee M., et al. Organic nanohybrids for fast and sustainable energy storage. Adv. Mater. 26, 2558-2565 (2014).

Li Q. et al. Aluminum as anode for energy storage and conversion: A review. J. Power Sources 110, 1-10 (2002).

Liang Y., et al. Organic electrode materials for rechargeable lithium batteries. Adv. Energy. Mater. 2, 742-769 (2012).

Lin M.-C., et al. An ultrafast rechargeable aluminium-ion battery. Nature 520, 324-328 (2015).

Morita Y., et al. Organic tailored batteries materials using stable open-shell molecules with degenerate frontier orbitals. Nat. Mater. 10, 947-951 (2011).

Muldoon J., et al. Quest for nonaqueous multivalent secondary batteries: Magnesium and beyond. Chem. Rev 114, 11683-11720 (2014).

Piskunov A. V., et al. Quinone complexes of aluminum: Synthesis and structures. Russ. J. Coord. Chem. 36, 161-169 (2010).

Razuvaev G. A., et al. Reactions of sterically hindered o-quinones with alkyl derivatives of group III elements. Russ. Chem. Bull. 26, 1034-1037 (1977).

Schwab M. G., et al. Torands revisited: Metal sequestration and self-assembly of cyclo-2,9-tris-1,10-phenanthroline hexaaza macrocycles. Chem. Eur. J. 21, 8426-8434 (2015).

Tang L., et al. Preparation, structure, and electrochemical properties of reduced graphene sheet films. Adv. Funct. Mater. 19, 2782-2789 (2009).

Tarascon J.-M. et al. Issues and challenges facing rechargeable lithium batteries. Nature 414, 359-367 (2001).

Tsuda, T., et al. "electrochemical surface finishing and energy storage technology with room-temperature haloaluminate ionic liquids and mixtures." Journal of the Electrochemical Society 164.8 (2017): H5007.

Wang D.-Y., et al. Advanced rechargeable aluminium ion battery with a high-quality natural graphite cathode. Nat. Commun. 8, 14283 (2017).

Wang, H., et al. "High-voltage and noncorrosive ionic liquid electrolyte used in rechargeable aluminum battery." ACS applied materials & interfaces 8.41 (2016): 27444-27448.

Wang, S. et al. Aluminum chloride-graphite batteries with flexible current collectors prepared from Earth-abundant elements. Adv. Sci. 5, 1700712 (2018).

Wu K. H., et al. The value of mixed conduction for oxygen electroreduction on graphene-chitosan composites. Carbon 73, 234-243 (2014).

\* cited by examiner

PQ-Ref

PQ-Δ

PQ-Lin

PQ-Δ³•⁻·3AlCl₂

PQ-Δ-HY

After cycling 50 times by cyclic voltammetry

PQ-Ref    PQ-Lin    PQ-Δ

RECHARGEABLE ALUMINUM ORGANIC BATTERIES

CROSS-REFERENCE TO RELATED APPLICATIONS

This application represents the U.S. national stage entry of International Application PCT/US2019/042547 filed Jul. 19, 2019, which claims benefit of priority to U.S. Provisional Application 62/700,614, filed Jul. 19, 2018, the contents of each are incorporated herein by reference in their entireties.

FIELD OF INVENTION

The disclosed technology is generally related to active materials for use with rechargeable aluminum organic batteries. More specifically, the present technology is directed to cathode materials comprising triangular phenanthrenequinones and graphite.

BACKGROUND

Since the 1990s, lithium-ion batteries (LIBs), based on lithium-containing inorganic cathodes and graphite anodes, have met with stunning successes in applications associated with mobile electronic devices.[4,5] The overall performance of LIBs remains, however, unsatisfactory for renewable energy-storage applications because of their limited cycle life, safety, and relatively high cost.[6,7] It follows that next generation energy-storage devices need to satisfy very much higher standards than the current state-of-the-art LIBs. With this goal in mind, rechargeable aluminum batteries (ALBs) offer considerable promise. Aluminum is the third most abundant element[8] (8.1 wt %) in the Earth's crust, after oxygen and silicon, and has one of the highest theoretical volumetric capacities (8056 mAh cm$^{-3}$) on account of its multiple redox states.[8,9,10] It is worth noting that the development of ALBs has not reached an advanced stage yet. In particular, it has proved difficult to design electrode materials that can intercalate aluminum (complex) ions reversibly.[8,11] Also, the number of currently available materials for use in electrochemically stable aluminum-based electrolytes is limited.[9,12] As a result, there is a need for new materials for use with rechargeable aluminum batteries.

BRIEF SUMMARY OF THE INVENTION

Disclosed herein are rechargeable aluminum organic batteries and active materials used therein. The active materials are materials that participate in the electrochemical charge or discharge reaction such as cathodic materials. The cathodic materials used herein comprise a macrocycle comprising a substituted or unsubstituted phenanthrenequinone unit and a graphite flake.

Suitably, the macrocycle comprises three substituted or unsubstituted phenanthrenequinone units in a triangular arrangement. The substituted or unsubstituted phenanthrenequinone unit may comprise

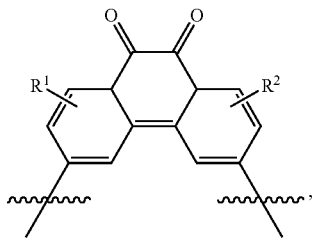

wherein $R^1$ and $R^2$ are independently selected from hydrogen, halogen, azide, alkyl, aralkyl, alkenyl, alkynyl, cycloalkyl, hydroxyl, alkoxyl, amino, nitro, imino, amido, carbonyl, —C(O)alkyl, carboxy, —CO$_2$alkyl, alkylthio, sulfonyl, sulfonamido, sulfhydryl, sulfonamide, heterocyclyl, aryl, heteroaryl, —CF$_3$, or —CN. In some embodiments of the invention, the macrocycle comprises a compound of formula

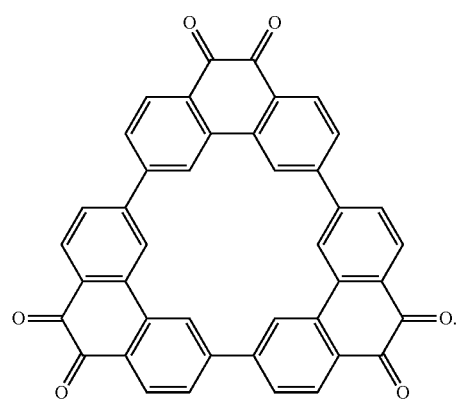 [SMILES: O=c1c(=O)c2ccc3cc2c2cc(ccc12)c1ccc2c(=O)c(=O)c4ccc(cc4c2c1)c1ccc2c(=O)c(=O)c4ccc3cc4c2c1]

The macrocycle may comprise a cationic aluminum complex. Suitably, the macrocycle comprises three substituted or unsubstituted phenanthrenequinone units in a triangular arrangement and each of the phenathrenequinone units chelate a cationic aluminum center. The substituted or unsubstituted phenanthrenequinone unit may comprise

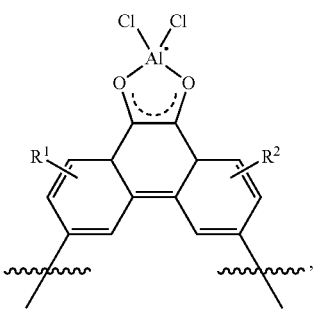

wherein $R^1$ and $R^2$ are independently selected from hydrogen, halogen, azide, alkyl, aralkyl, alkenyl, alkynyl, cycloalkyl, hydroxyl, alkoxyl, amino, nitro, imino, amido, carbonyl, —C(O)alkyl, carboxy, —CO$_2$alkyl, alkylthio, sulfonamido, sulfhydryl, sulfonamide, heterocyclyl, aryl, heteroaryl, —CF$_3$, or —CN. In some embodiments, the macrocycle comprises the cationic aluminum complex of formula

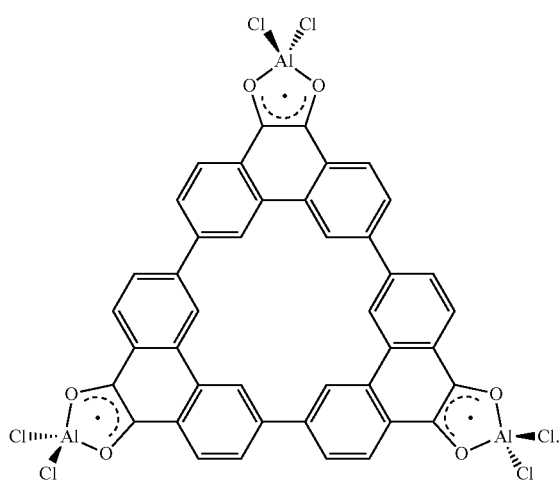

The cathodic materials described herein may comprise about 2.0:1.0 and about 1.0:2.0 of the macrocycle to the graphite flake by weight.

The cathodic material may further comprise an electron-conducting additive. Suitably the electron-conducting additive is a carbon or graphitic material such as Denka Black.

The cathodic material may further comprises a binder material. Suitably the binder material is a polymer such as polyvinylidene (PVDF).

The cathodic material described herein may be used to prepare an electrode. The electrode may comprise any of the cathodic materials described herein and a substrate.

Another aspect of the invention is a battery comprising a cathode made of any of the cathodic materials described herein and an electrolyte. Suitably, the electrolyte comprises an aluminum halide. In certain embodiments, the aluminum halide is tetrachloraluminate. The electrolyte may comprise an imidazolium, suitably ethyl-3-methylimidazolium. The battery may further comprise an anode, suitably comprising aluminum or an aluminum-based active material.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 1A shows a graphical representation of the phenanthrenequinone monomer (PQ-Ref). FIG. 1B shows a graphical representation of the phenanthrenequinone triangle (PQ-Δ). FIG. 1C shows a graphical representation of the linear phenanthrenequinone trimer (PQ-Lin). FIG. 1D shows a graphical representation of the tetracoordinate complex, $(PQ\text{-}\Delta^{3*})\cdot 3AlCl_2$. FIG. 1E shows a graphical representation of the graphite flake-blended phenanthrenequinone triangle hybrid (PQ-Δ-HY).

FIG. 2A shows the cyclic voltammetry of each of the PQ derivatives, PQ-Δ, PQ-Lin, and PQ-Ref, at a scan rate of 5 mV $s^{-1}$. FIG. 2B shows the comparison of the galvanostatic voltage profiles of the PQ derivatives, PQ-Δ, PQ-Lin, and PQ-Ref. FIG. 2C shows the cycling performances of PQ derivatives, of the PQ derivatives PQ-Δ, PQ-Lin, and PQ-Ref, at a current rate of 0.2 A $g^{-1}$ (=2 C). FIG. 2D shows the rate capability measurement of PQ-Δ. The initial 30 cycles were measured at 1 C and the current rate was increased every 20 cycles up to 100 C. FIG. 2E shows the extended cycling test of PQ-Δ at a current rate of 2 A $g^{-1}$ (=20 C). The Coulombic efficiency is defined on the right axis.

FIG. 3A shows the galvanostatic voltage profile of PQ-Δ and its schematic illustration for each ex-situ state. FIGS. 3B-3D show the transmission electron microscopic (TEM) images of ex-situ electrodes and corresponding (inset) powder X-ray (PXRD) diffraction traces for pristine PQ-Δ (FIG. 3B), discharged PQ-Δ (FIG. 3C), and charged PQ-Δ (FIG. 3D). FIG. 3E shows the energy-dispersive X-ray spectroscopy of the discharged state sample—carbon (C), oxygen (O), aluminum (Al), and chlorine (Cl).

FIGS. 4A-4B show the SEM (FIG. 4A) and TEM (FIG. 4B) images which characterize the microstructures. FIG. 4C shows the galvanostatic voltage profile of PQ-Δ-HY and its electrochemical redox schematic. Specific energy contributed from PQ-Δ and graphite flakes are represented in Region 1 and Region 2, respectively. FIG. 4D shows the cycling performance of PQ-Δ-HY at the current rate of 0.2 A $g^{-1}$ (=2 C). FIG. 4E shows the rate capability measurement of PQ-Δ-HY.

FIGS. 5A-5B show the SEM images and digital photographs (insets) of PQ-Δ (FIG. 5A) and PQ-Δ-HY (FIG. 5B) electrodes at their pristine states. The areal loadings of the active materials in FIGS. 5A and 5B are 2 and 9 mg $cm^{-2}$, respectively. The electrode compositions in FIGS. 5A-5B are PQ-Δ:Denka black:PVDF=4:5:1 and PQ-Δ-HY:graphite:Denka black:PVDF=4:4:1:1, respectively. FIG. 5C shows the galvanostatic voltage profiles and FIG. 5D shows the rate capability measurement of PQ-Δ-HY electrodes with different mass loadings of 2 and 9 mg $cm^{-2}$ at 0.1 A $g^{-1}$. FIGS. 5E-5F show the cycling performance areal capacity (FIG. 5E) and specific capacity (FIG. 5F) of the PQ-Δ-HY electrodes at a current rate of 0.2 A $g^{-1}$ (=2 C).

FIG. 7A shows the cyclic voltammetry (CV) of pyrolytic graphite-based current collector at 0.7-1.75 V. FIG. 7B shows the cyclic voltammetry (CV) of pyrolytic graphite-based current collector at 0.7-2.0 V voltage range.

FIG. 8A shows the CV results of PQ-Ref up to 200 cycles at 100 mV $S^{-1}$ scan rate. FIG. 8B shows the CV results of PQ-Lin up to 200 cycles at 100 mV $S^{-1}$ scan rate. FIG. 8C shows the CV results of PQ-Δ up to 200 cycles at 100 mV $S^{-1}$ scan rate.

FIG. 9A shows the cyclic voltammetry profiles of PVDF. FIG. 9B shows the cyclic voltammetry profiles of Denka black at a voltage range of 0.5-2.3 V in ALB configuration. Denka black electrode was composed of Denka black and PVDF in a weight ratio of 1:1.

FIG. 10A shows the CV profiles of the first three cycles at a scan rate of 5 mV s$^{-1}$. FIG. 10B shows the galvanostatic measurement profile at the 0.2 C current rate. FIG. 10C shows the corresponding cycling data.

FIG. 11A shows the voltage versus differential capacity plot of graphite flake. FIG. 11B shows the voltage versus differential capacity plot of PQ-Δ-HY. The galvanostatic measurement was performed at the current rate of 100 mA g$^{-1}$ in the voltage range of 0.50-2.35 V.

FIG. 13A shows the spectra obtained before 50 cycles of CV. FIG. 13B shows the spectra obtained after 50 cycles of CV.

FIG. 14A shows the power X-ray diffraction result of PQ-Ref. FIG. 14B shows the power X-ray diffraction result of PQ-Lin.

FIG. 14C shows the power X-ray diffraction result of PQ-Δ.

FIG. 15A shows the Powder X-ray diffraction results of PQ-Δ-HY. FIG. 15B shows the powder X-ray diffraction results of PQ-Ref-HY compounds. The ratio between PQ derivative and graphite flake was 0.7 for both composites. PQ-Δ-HY diffraction shows restacking of PQ-Δ along with graphite flake, whereas the crystalline phase of PQ-Ref was still preserved in PQ-Ref-HY after the formation of the hybrid electrode.

FIG. 18A shows the SEM image of PQ-Ref-HY. FIG. 18B shows the EDX mapping of carbon. FIG. 18C shows the EDX mapping of oxygen.

FIG. 19A shows the XPS Spectra of pristine, discharged, and charged PQ-Δ electrodes in the regions of O 1s. FIG. 19B shows the XPS Spectra of pristine, discharged, and charged PQ-Δ electrodes in the regions of Al 2p.

DETAILED DESCRIPTION OF THE INVENTION

Disclosed herein are rigid chiral redox-active triangular macrocycles. Also disclosed are methods of synthesizing the redox-active macrocycles as well as devices fabricated from the disclosed macrocycles. The redox-active macrocycles comprise a mixture of redox-active subunits that are capable of undergoing reversibly accept electrons. Because of the use of different redox-active subunits, the subunits may be sequentially reduced and the reduction potentials for the macrocycle may be significantly tuned to provide unique electrochemical behavior. As a result, these redox-active macrocycles may be exploited for novel device fabrication.

Herein, we demonstrate a new class of active materials for ALBs, namely a redox-active macrocyclic compound, in which the redox-active units are covalently linked together to form a triangular constitution. We prepared a triangular macrocycle, namely, the phenanthrenequinone triangle (PQ-Δ)

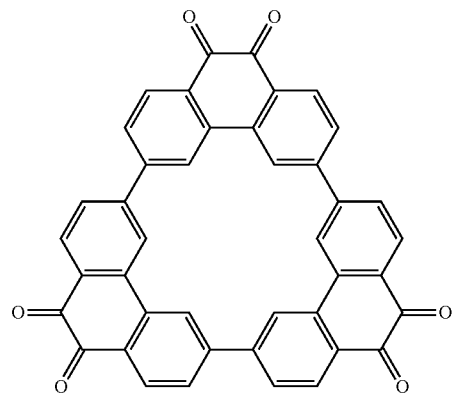 [SMILES: O=c1c(=O)c2ccc3cc2c2cc(ccc12)c1ccc2c(=O)c(=O)c4ccc(cc4c2c1)c1ccc2c(=O)c(=O)c4ccc3cc4c2c1]

Figure 1A:
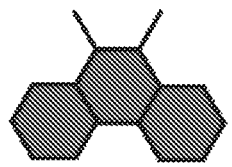
FIGS. 1A-1E show a series of phenanthrenequinone (PQ) derivatives for rechargeable aluminum batteries (ALBs).
Figure 1B:
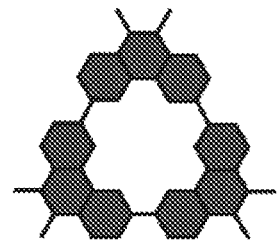

(see, also, FIG. 1B) and confirmed the reversible intercalation of cationic chloroaluminate. PQ-Δ showed a reversible specific capacity of 94 mAh g$^{-1}$ with a cyclability of up to 5000 cycles, most likely resulting from the sterically hindered constitution of the molecular triangle with sufficient flexibility that can accommodate the strain accompanied by chloroaluminate ion (de)intercalation. Furthermore, we fabricated a phenanthrenequinone triangle hybrid material (PQ-Δ-HY) (FIG. 1E) by blending PQ-Δ with graphite flakes. This optimization enabled the dual intercalation of cationic and anionic chloroaluminates, increasing the specific capacity to 126 mAh g$^{-1}$ at 1.7 V vs Al/Al3+, along with other advantages such as enhanced conductivity and high loading capability. Our findings suggest that redox-active compounds with defined constitutional arrangements are able to achieve homogeneous stacking, ensuring the reversible intercalation of chloroaluminate ions during the operation of ALBs.

The macrocycles disclosed herein, may be used to prepare active materials, cathodes, and batteries. Rigid macrocycles are cyclic macromolecules or a macromolecular cyclic portion of a molecule that is constrained against large-amplitude conformational rearrangement around the cyclic portion of the molecule. The macrocycle comprises a substituted or unsubstituted phenanthrenequinone (PQ) unit. The PQ unit comprises a diradical having a formula

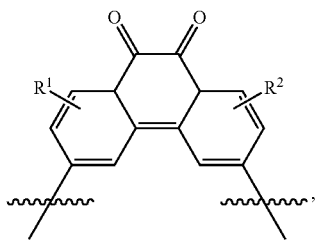

The PQ unit may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. In certain embodiments, the aromatic ring is substituted at one or more ring positions with halogen, alkyl, hydroxyl, or alkoxyl. In certain other embodiments, the aromatic ring is not substituted. $R^1$ and $R^2$ may be independently selected from hydrogen, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, or —CN.

These active materials, cathodes, and batteries may comprise any of the rigid macrocycles described here, including, without limitation PQ-Δ.

The macrocycle may comprise a cationic aluminum complex. Suitably, any of the substituted or unsubstituted phenanthrenequinone (PQ) unit described above may be used to prepare the complex. The complex may comprise a cationic aluminum center chelated by the oxygen atoms of the PQ unit. The cationic aluminum center may comprise $AlCl_2^+$. This allows for the preparation of aluminum containing complexes such as

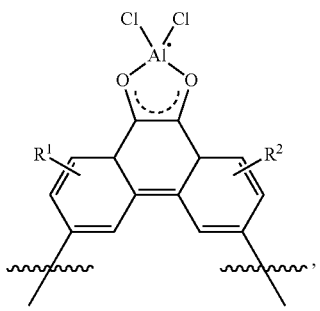

In certain embodiments, the macrocycle comprises PQ-Δ³⁻·3AlCl₂

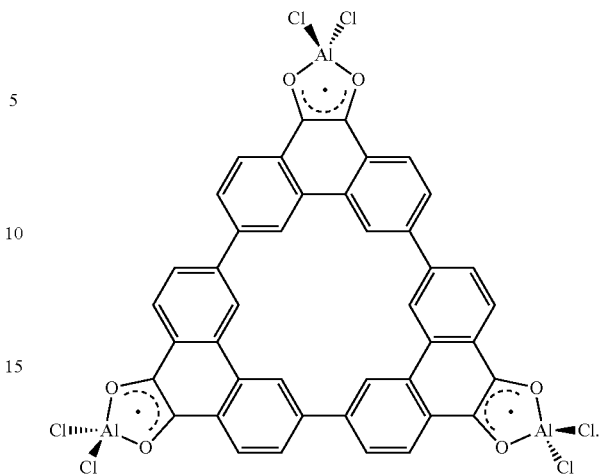

(FIG. 1D).

Figure 1C:
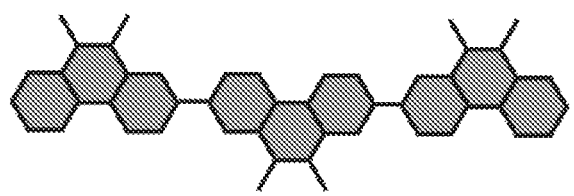
Figure 1D:
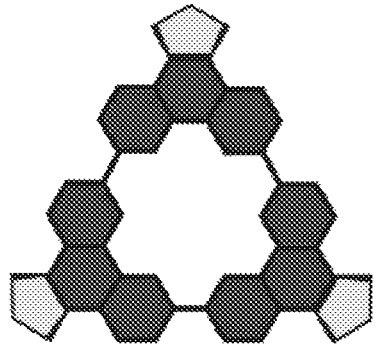
Figure 1E:
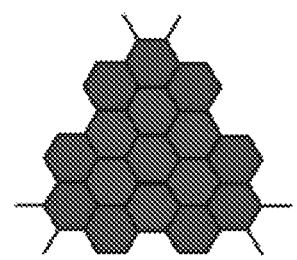

The cathodic material may also comprise graphite flake. Not only does the graphite flake improve conductivity of the cathodic material, but the graphite flake may also be an active substance. The cathodic material may comprise any suitable weight ratio of the macrocycle and the graphite flake. In some embodiments, the cathodic material comprises between about 2.0:1.0 and about 1.0:2.0 of the macrocycle to the graphite flake by weight, including between about 1.8:1.0 and about 1.0:1.8, about 1.5:1.0 to about 1.0:1.5, or about 1.2:1.0 and about 1.0:1.2. Suitably, the graphite flake is used to prepare a hybrid materials with any of the macrocycles described herein. Suitably, the hybrid material is PQ-Δ-HY (FIG. 1E).

The active materials may further comprise a binder material and/or an electron-conducting material. In some embodiments, the cathode material further comprises a solvent.

In some embodiments, the macrocycle is 1-90 wt % (e.g., 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or any ranges therebetween) of the cathodic material. In some embodiments, the macrocycle is 5-80 wt %, 10-70 wt %, 20-60 wt %, 30-50 wt %, etc. of the cathode material.

In some embodiments, the binder material comprises a polymer selected from the group consisting of: styrene-butadiene rubber (SBR); polyvinylidene fluoride (PVDF); polytetrafluoroethylene (PTFE); copolymer of tetrafluoroethylene, hexafluoropropylene, and vinylidene fluoride; copolymer of hexafluoropropylene and vinylidene fluoride; copolymer of tetrafluoroethylene and perfluorinated vinyl ether; methyl cellulose; carboxymethyl cellulose; hydroxymethyl cellulose; hydroxyethyl cellulose; hydroxypropylcellulose; carboxymethylhydroxyethyl cellulose; nitrocellulose; colloidal silica; and combinations thereof. In some embodiments, binder material comprises PVDF. In some embodiments, the binder material is 1-25 wt % (e.g., 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, or any ranges therebetween) of the cathodic material. In some embodiments, the binder material is 5-15 wt % of the cathode material.

In some embodiments, the solvent comprises N-methyl-pyrrolidone (NMP).

In some embodiments, the electron-conducting additive is a carbon or graphitic material. In some embodiments, the carbon or graphitic material is selected from the list consisting of: a graphite, a carbon black, a graphene, and a carbon nanotube. In some embodiments, the carbon or graphitic material is a graphite selected from the group consisting of: graphite worms and expanded graphite. In some embodiments, the carbon or graphitic material is chemically-etched or expanded soft carbon, chemically-etched or expanded hard carbon, or exfoliated activated carbon. In some embodiments, the carbon or graphitic material is a carbon black selected from the group consisting of: acetylene black (e.g., Denka black), channel black, furnace black, lamp black thermal black, chemically-etched or expanded carbon black, and combinations thereof. In some embodiments, the carbon or graphitic material is a carbon nanotube selected from the group consisting of: chemically-etched multi-walled carbon nanotube, nitrogen-doped carbon nanotube, boron-doped carbon nanotube, chemically-doped carbon nanotube, ion-implanted carbon nanotube, and combinations thereof. In some embodiments, the electron-conducting additive comprises carbon black. In some embodiments, the electron-conducting additive is 1-99 wt % (e.g., 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 91 wt %, 92 wt %, 93 wt %, 94 wt %, 95 wt %, 96 wt %, 97 wt %, 98 wt %, 99 wt %, or any ranges therebetween) of the cathode material. In some embodiments, the electron-conducting additive is 5-85 wt % of the cathode material.

In some embodiments, the cathodic material is present as a slurry. In some embodiments, the slurry comprises a solid content of 40-80% 40 wt %, 45 wt %, 50 wt %, 55 wt %, 60 wt %, 65 wt %, 70 wt %, 75 wt %, 80 wt %, or any ranges there between).

In some embodiments, the cathodic material is dried (e.g., solvent evaporated out of a slurry). In some embodiments, the cathodic material is dried under increased heat (e.g., above room temperature (e.g., 40° C., 50° C., 60° C., 70° C., 80° C., 90° C., 100° C., 110° C., 120° C., 130° C., 140° C., 150° C.), reduced pressure (e.g., below atmospheric pressure, under vacuum), etc. In some embodiments, provided herein are cathodes comprising a cathode material described herein. In some embodiments, a cathode further comprises a foil substrate. In some embodiments, the foil substrate is an aluminum foil substrate. In some embodiments, a slurry comprising the cathode material is coated onto the foil substrate and dried.

In some embodiments provided herein are batteries comprising a cathode described herein. In some embodiments, a battery described herein is rechargeable. In some embodiments, provided herein are methods of storing energy within a batter described herein.

The battery may further comprise an anode. In some embodiments, an anode comprises: (a) an aluminum or other aluminum-based active material; (b) a binder material; (c) an electron-conducting additive; and (e) a substrate. In some embodiments, an anode further comprises a solvent. In some embodiments, the binder material, electron-conducting additive, and/or solvent of the anode are selected from the binder materials, electron-conducting additives, and/or solvents described herein for use in cathodes.

In some embodiments, a battery further comprises a separator. In some embodiments, the separator comprises polypropylene (PP), polyethylene (PE), or a combination of layers thereof.

In some embodiments, a battery further comprises an electrolyte material. The electrolyte within the electrochemical cell will be tailored to the particular application and components within the electrochemical cell. In some cases the electrolyte is a room-temperature ionic liquid (RTIL). "Room-temperature ionic liquid" or "RTIL" refers to salts that liquefy below 373 K. The interest in these materials stems from their favorable physicochemical properties, such as low-flammability, negligible vapor pressure, relatively high ionic conductivity, and high electrochemical stability.

RTILs may be prepared from a Lewis Acid and a Lewis base. The Lewis acid may be any chemical species capable of accepting an electron pair to from a Lewis base to form a Lewis adduct. RTILs may be prepared by the mixing of the Lewis Acid with a salt of a Lewis base. The salt's anionic Lewis base can reversibly react with the Lewis acid to form an anionic adduct, resulting the RTIL comprising the anionic adduct and the salt's cation.

Many Lewis acids are known in the art, including metal containing Lewis acids capable of forming an RTIL. Examples of metal containing Lewis acids capable of forming ionic liquids include, without limitation, Group IIIA halometallates or a Group IVA metalhalide. Exemplary Group IIIA halometallates include, without limitation, haloaluminates, halogallates, and haloindates such as $AlCl_3$, $AlBr_3$, $GaCl_3$, or $InCl_3$. Exemplary Group IVA metalhalides include, without limitation, silicon halides and germanium halides such as $SiCl_4$ or $GeCl_4$.

The salt comprising the Lewis base may be any suitable Lewis base that can form an ionic liquid with the selected Lewis acid. Lewis bases capable of forming ionic liquids, include without limitation, halides such as F, Cl, and Br; fluorous-anions such as $PF_6^-$, $BF_4^-$, $CF_3SO_3^-$; or $(CF_3SO_3)_2N^-$, or non-fluorous anions such as alkylsulfates. In some embodiments, the salt may also comprise a nitrogen containing organic cation such as an imidazolium, a pyridinium, an ammonium, a pyrrolidinium, or any combination thereof. Examples include, without limitation, 1-ethyl-3-methylimidazolium, 1-butyl-3-methylimidazolium, or 1-(1-butyl)pyridinium. In other embodiments, the salt may comprise an alkali cation such as $Li^+$, $Na^+$, $K^+$, or any combination thereof. Exemplary salt include, without limitation, 1-ethyl-3-methylimidazolium chloride, 1-butyl-3-methylimidazolium chloride, or 1-(1-butyl)pyridinium chloride, LiCl, NaCl, or KCl.

In other embodiments, the electrolyte may comprise a deep eutectic solvent (DES). A "deep eutectic solvent" or "DES" is a metallifeorous solution composed of cations and anions via a disproportionation process. The DES may be prepared by mixing a Lewis Acid, such as any of the Lewis acids described above, and a polar molecule. The polar molecule may be any suitable polar molecule capable of forming a DES, including, without limitation, urea, dimethylsulfone, an amide, a glyme, or any combination thereof.

In particular embodiments, the Lewis acid is a haloaluminate $AlX_3$, where X is Cl or Br. RTILs or DESs may be prepared from the mixing of the haloaluminate with a salt or polar molecule as explained above. The haloaluminate should be mixed with a sufficient amount of the salt or polar molecule to prepare a reducible $[AlX_4]^-$ or $[Al_2X_7]^-$ haloalumine. In electrolytes comprising chloroaluminates, for example, Al and Al alloy coatings can be prepared from those containing more than 50 mol % $AlCl_3$, i.e., Lewis acidic RTILs in which the reducible $[Al_2Cl_7]^-$ ion exists (as shown in eqn 2). Although the $[AlCl_4]^-$ ion, which is a major constituent of these electrolytes, is in principle reducible to Al, the organic cation component is typically reduced at more positive potentials than this ion. Thus reduction of $[AlCl_4]^-$ is typically only seen in metal halide-$AlC_3$ electrolytes. Thus its often preferable for the $[Al_2Cl_7]^-$ ion to be present. The reactivity of the haloaluminates as well as their adjustable Lewis acidity make them well suited for the applications described herein.

The molar ratio of the Lewis acid to the Lewis base or polar molecule determines the acidity of the electrolyte and the concentration of the ion species. When the molar ratio of Lewis acid to Lewis base or Lewis acid to polar molecule is greater than 1.0, the electrolyte is acidic. Suitable molar ratios of Lewis acid to Lewis base or polar molecule are typically greater than 1.0. In some embodiments, the molar ratio is between 1.0 and 2.0, including within 1.2 and 1.8 or 1.2 to 1.6.

Exemplary electrolytes include those described in the following references: Electrochemistry, 82(11):946-948 (2014); ACS Appl. Mater. Interfaces 8: 27444-27448 (2016); Journal of The Electrochemical Society, 164 (8):H5007-H5017 (2017); Proc Natl Acad Sci 114(5):834-839 (2017); Angewandte Chemie 130(7):1916-1920 (2017); Chem 4(3): 586-598 (2018); and Chem. Commun., 54:4164-4167 (2018).

In some embodiments, provided herein are methods of preparing a cathode material comprising a macrocycle described herein; methods of preparing a cathode comprising said cathode material; methods of preparing a battery comprising said cathode; and methods of preparing a device comprising said battery.

In some embodiments, provided herein are systems, compositions, and devices comprising organic capacitors, super capacitors, organic dopants, redox-active charge carriers, photovoltaics, solar cells, organic thin-film semiconductors, etc. comprising a macrocycle described herein.

Design and Synthesis of Phenanthrenequinone Derivatives

Figure 14A:
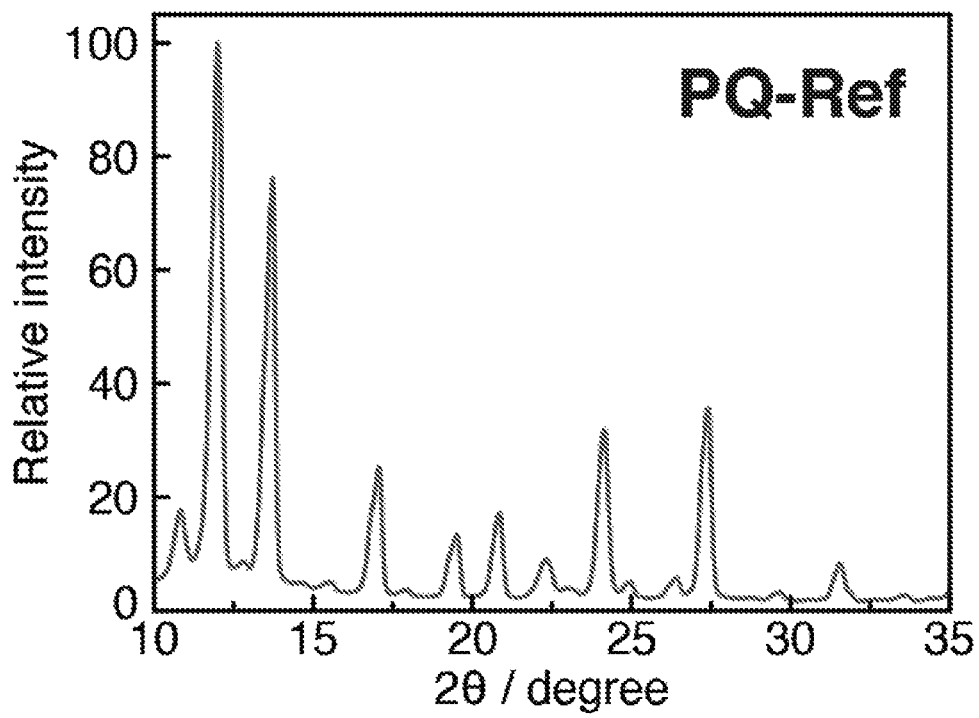
FIGS. 14A-14C show the powder X-ray diffraction results.
Figure 14B:
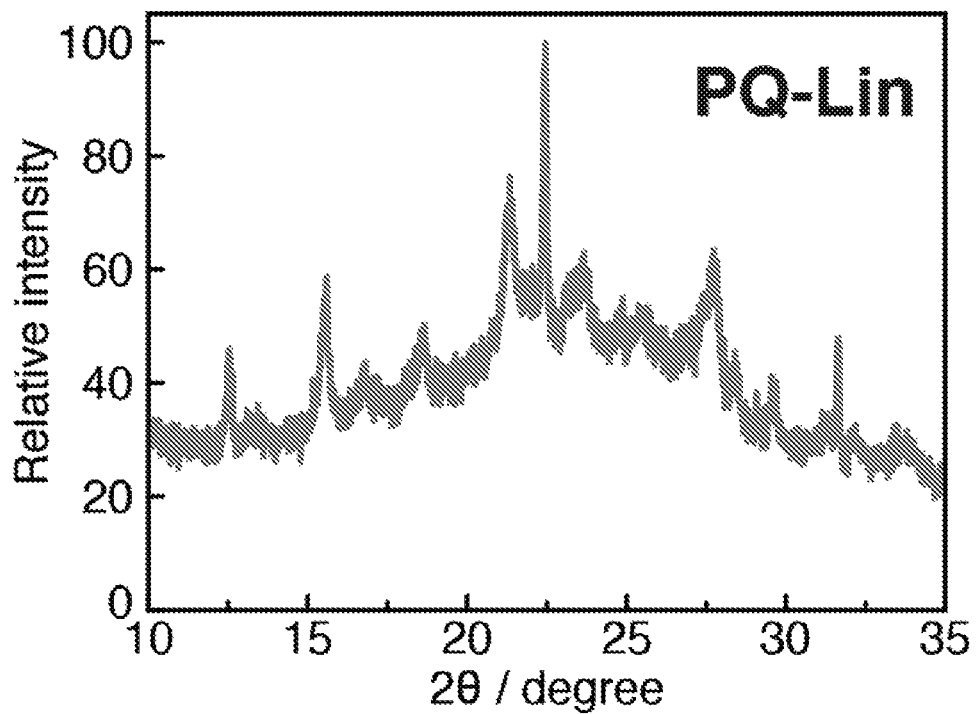
Figure 14C:
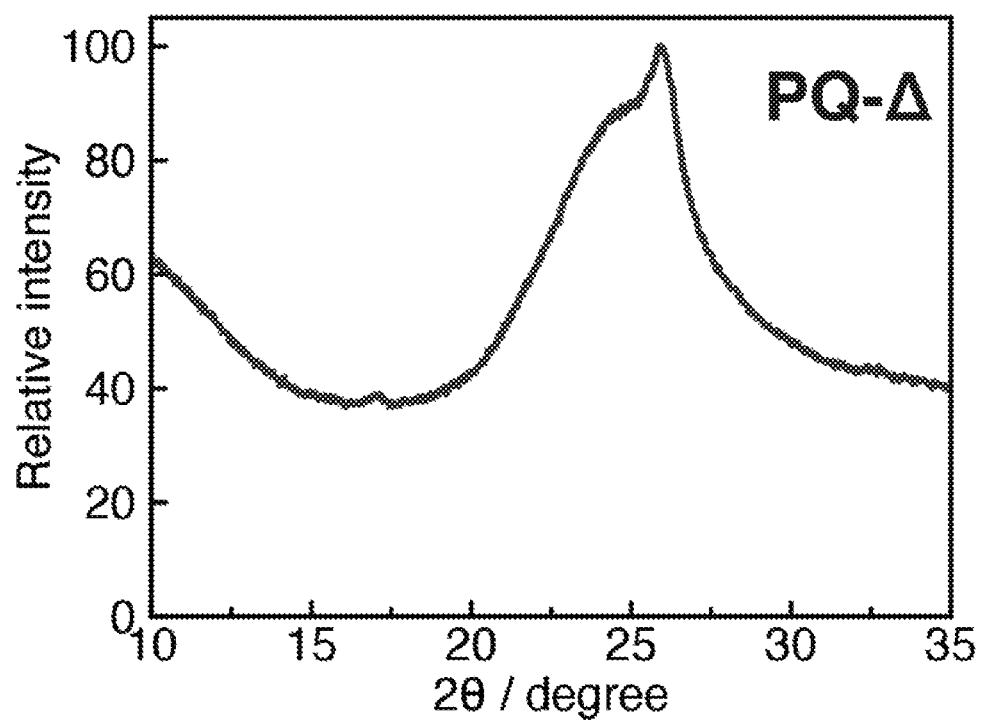
Figure 15A:
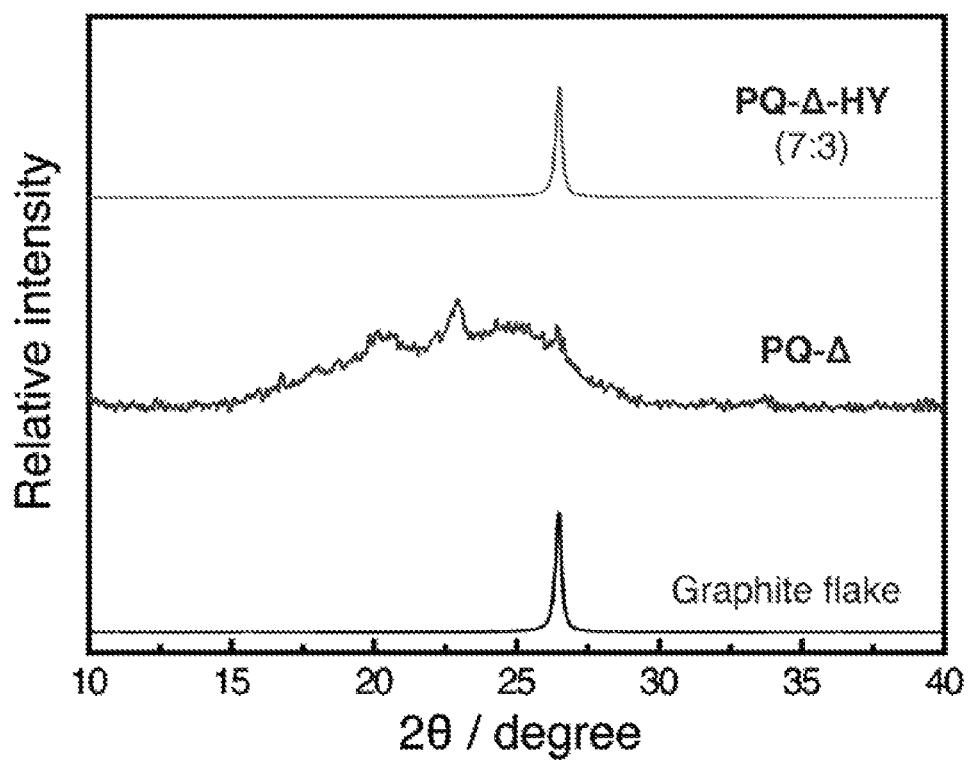
FIGS. 15A-15B show the powder X-ray diffraction results.
Figure 15B:
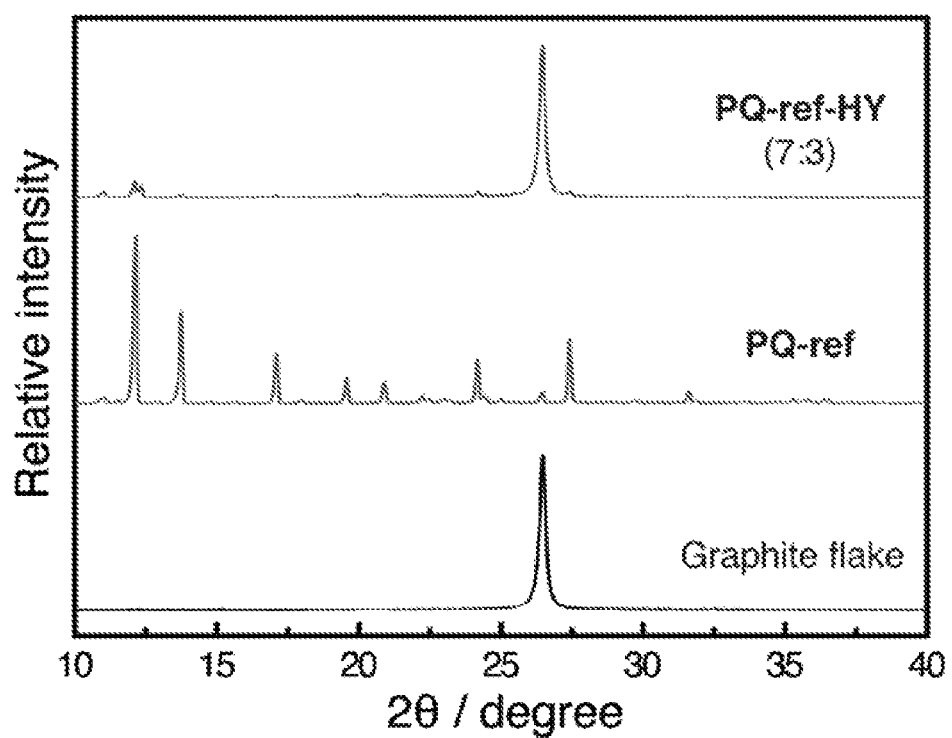
Figure 17A:
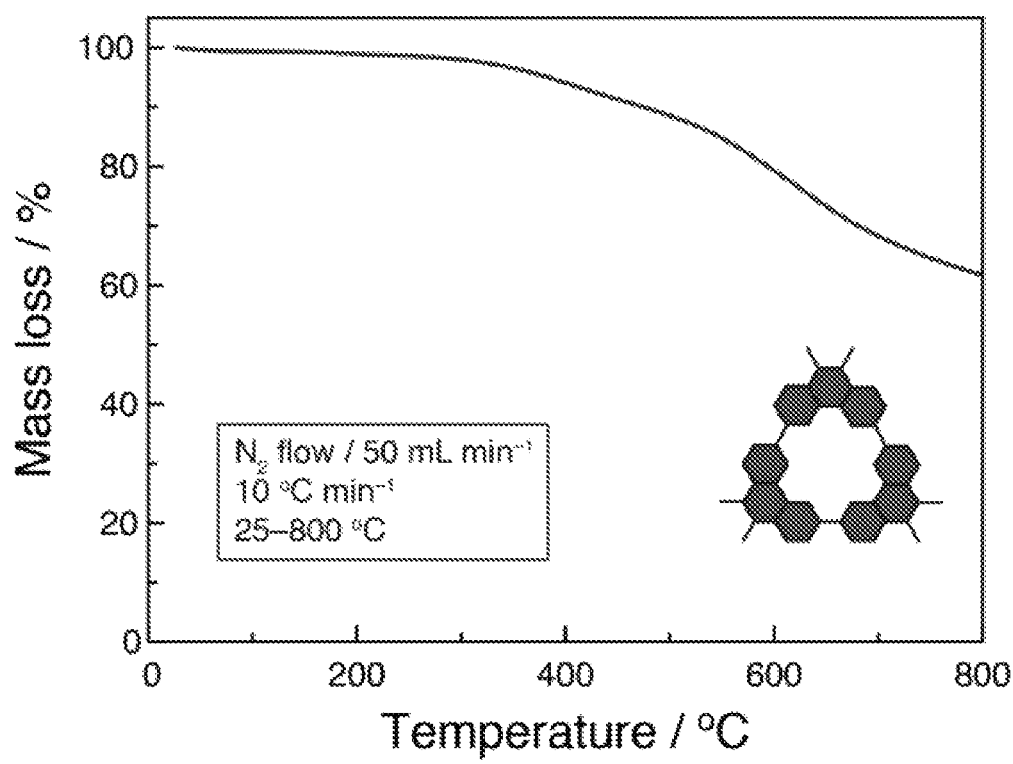
FIG. 17A shows the TGA curve of PQ-Δ.
Figure 17B:
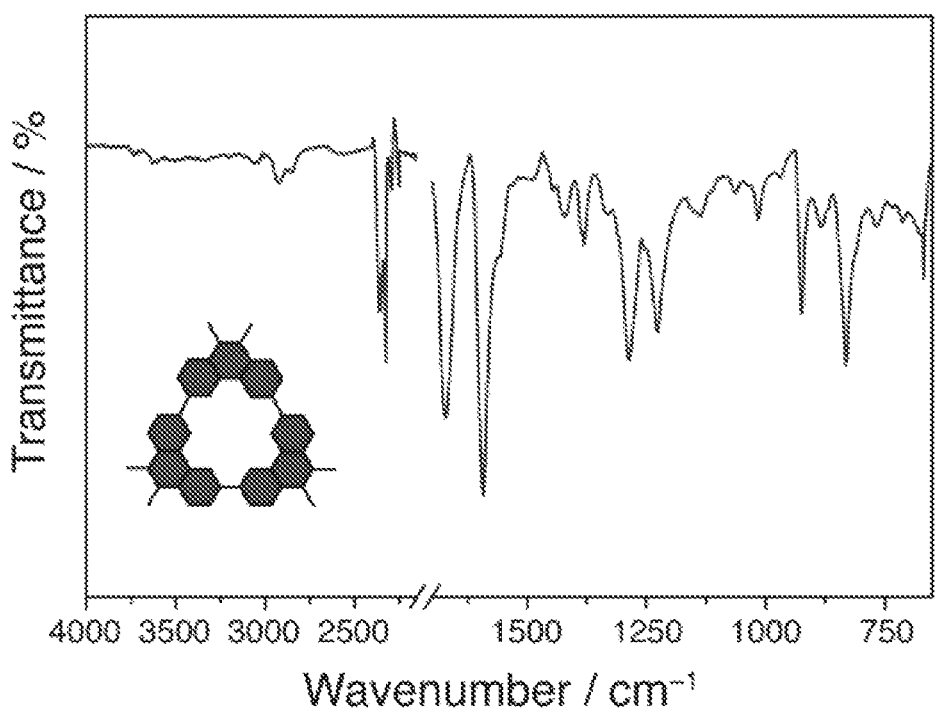
FIG. 17B shows the FT-IR spectrum of PQ-Δ.

In an effort to achieve the reversible intercalation of Al-complex ion, we explored rigid and geometrically planar PQ-based compounds (FIG. 1B): PQ-Δ, previously reported by Müllen and co-workers[23]. Briefly, PQ was brominated in the presence of elemental bromine, 2,2'-bipyridine, and benzyl peroxide in refluxing nitrobenzene, resulting in the generation of 3,6-dibromophenanthrenequinone which was then subjected to a Yamamoto homocoupling process, using bis(cyclooctadiene)nickel as the reducing agent. The crude product was purified by Soxhlet extraction and PQ-Δ was isolated in 44% yield. In an effort to investigate the relationship between molecular geometry and ALB performance, we also prepared the phenanthrenequinone monomer (PQ-Ref) (FIG. 1A) and linear phenanthrenequinone trimer (PQ-Lin) (FIG. 1C). PQ-Ref was purchased from a commercial vendor and used as received. PQ-Lin was synthesised[24] by Suzuki coupling in a 1:2 molar ratio of a boronic acid ester and the iodide precursors of PQ, respectively. Detailed experimental conditions and procedures are described in the Examples. -Δ is insoluble in all common deuterated NMR solvents. Therefore, we conducted $^{13}$C CP MAS solid-state NMR measurements and confirmed the presence of the expected aromatic peaks for PQ-Δ. We also performed MALDI-TOF experiments using a 1:1 mixture of 2,5-dihydroxybenzoic acid and α-cyano-4-hydroxy-cinnamic acid as a matrix, and our data matched the theoretical and previously reported values.[23] The TGA profile of PQ-Δ reveals (FIG. 17A) that the macrocycle does not have a clear melting point, while the FTIR absorption at 1670 cm$^{-1}$ matches (FIG. 17B) well with that of a quinone reference peak. Notwithstanding many efforts, we could not produce a sufficiently high quality single crystal of PQ-Δ because of its poor solubility in all solvents. And so we turned our attention to powder X-ray diffraction (PXRD) and confirmed the crystallinity of all three compounds. The diffraction peak of PQ-Ref indicates (FIG. 14A) the highly crystalline phase, whereas the PQ-Lin diffraction peak (FIG. 14B) become broadened, on account of the rotational flexibility associated with its linear constitution. It transpires that PQ-4, which exhibits (FIG. 14C) one broad peak around 2θ=22-28°, makes it distinct from the other two PQ derivatives. This broad diffraction peak implies the presence of an amorphous layered structure[25, 26], resulting from the stacking of the rigid and planar molecular geometry.[27]

Electrochemical Measurements of Rechargeable Aluminum Batteries

Figure 7A:
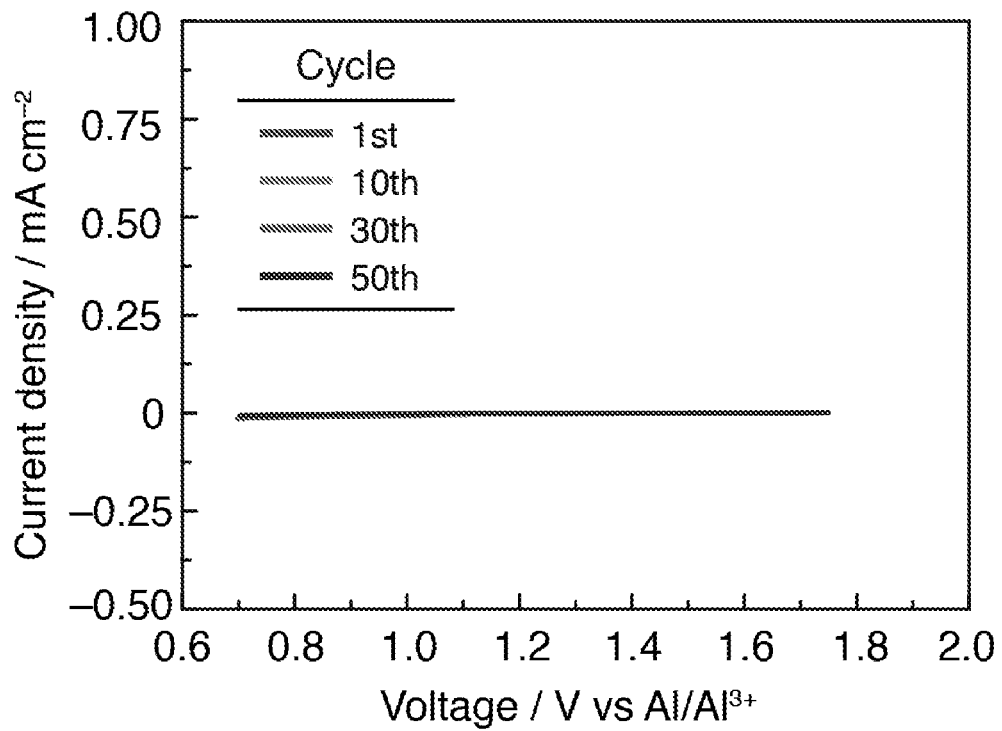
FIGS. 7A-7B show the cyclic voltammetry (CV) of pyrolytic graphite-based current collector.
Figure 7B:
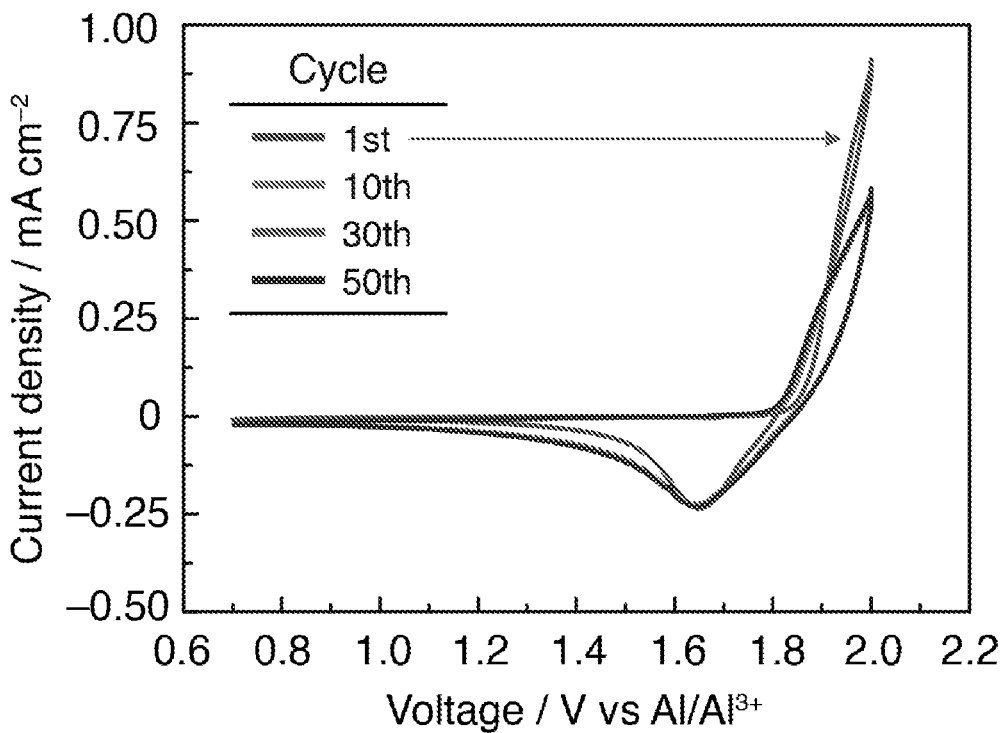

A modified Swagelok-type two-electrode cell[28] was used for making electrochemical measurements on ALBs. Detailed electrode preparations and cell configurations are described below. Hereafter, all potentials are based on Al/Al$^{3+}$ (−0.7 V vs NHE, in AlCl$_3$/EMImCl=1.3) redox couple, unless otherwise stated. Prior to analyzing the redox properties of the PQ derivatives, we confirmed (FIG. 7A) the stable voltage range of the imidazolium chloride electrolyte[28] and the graphite current collector[12] by conducting cyclic voltammetry (CV) without any active materials. During the CV measurement, we did not identify any noticeable redox peaks in the voltage range between 0.70-1.75 V, indicating a stable electrochemical cell configuration for ALB characterization. When the voltage range was increased (FIG. 7B) up to 2.00 V, however, new oxidation and reduction peaks appeared around 1.90 and 1.70 V, respectively, an observation which can most likely be attributed to the intercalation of anionic chloroaluminates inside the graphite current collector.[28]

Figure 2A:
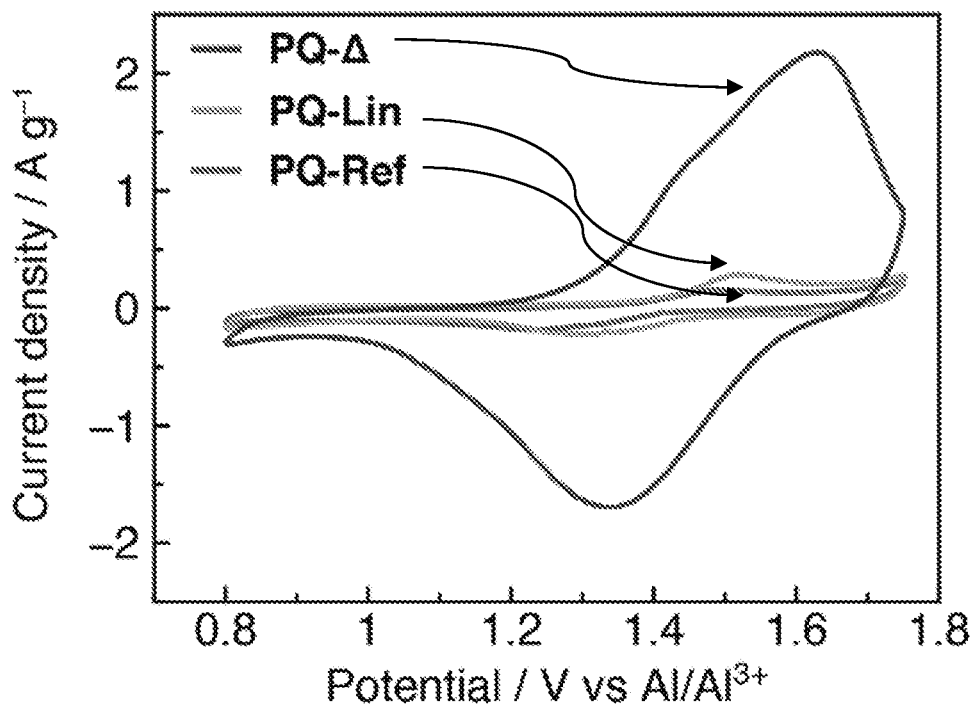
FIGS. 2A-2E show a series of electrochemical measurements of PQ derivatives. All of the electrochemical measurements were performed in the voltage range of 0.8-1.75 V vs $Al/Al^{3+}$. In galvanostatic measurements, theoretical specific capacity and C-rate (C) were calculated based on a 1:1 ratio of PQ:chloroaluminate.
Figure 2B:
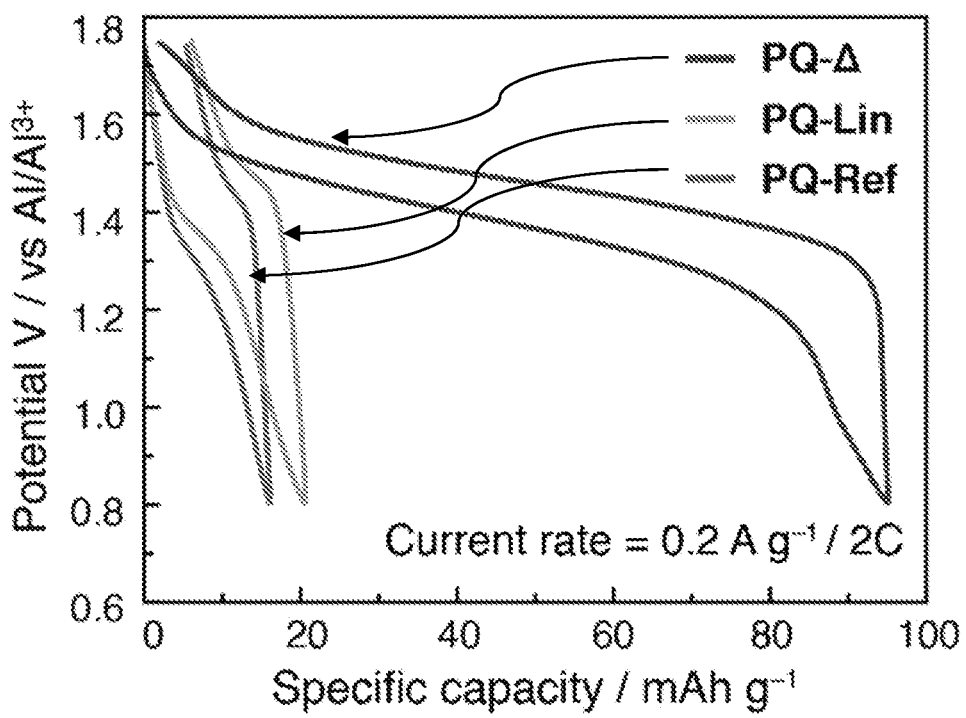
Figure 2C:
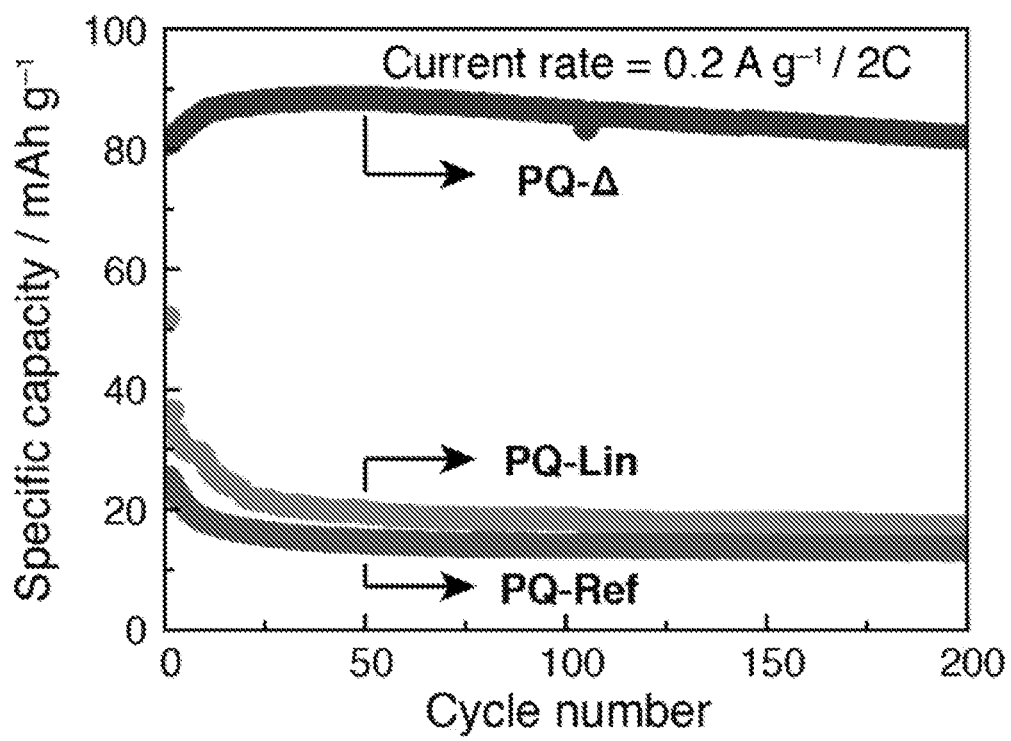
Figure 2D:
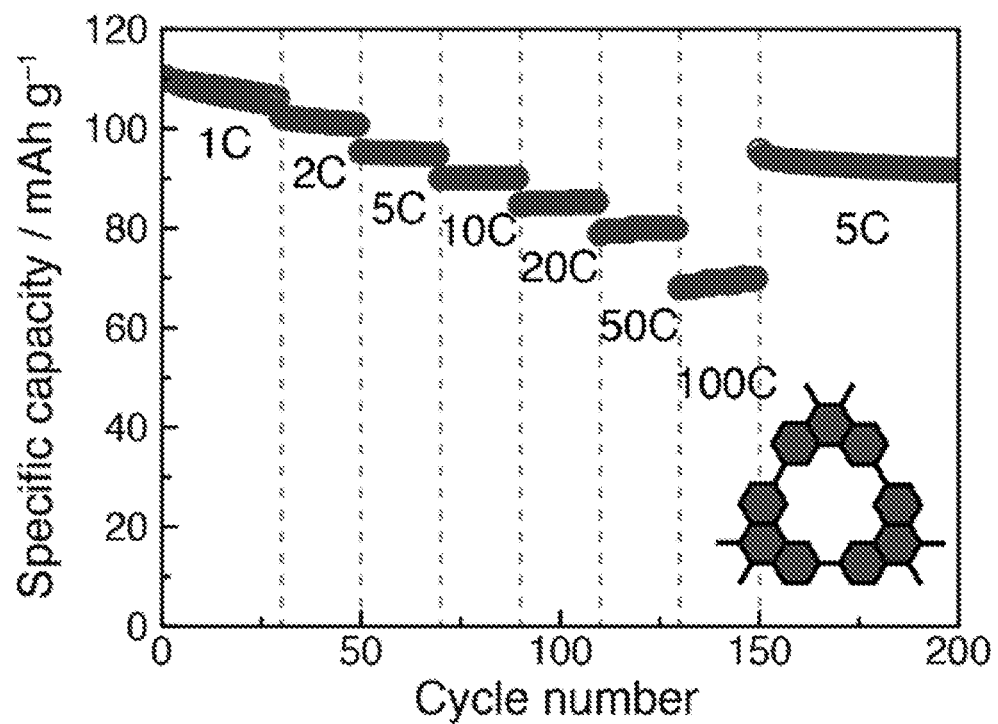
Figure 2E:
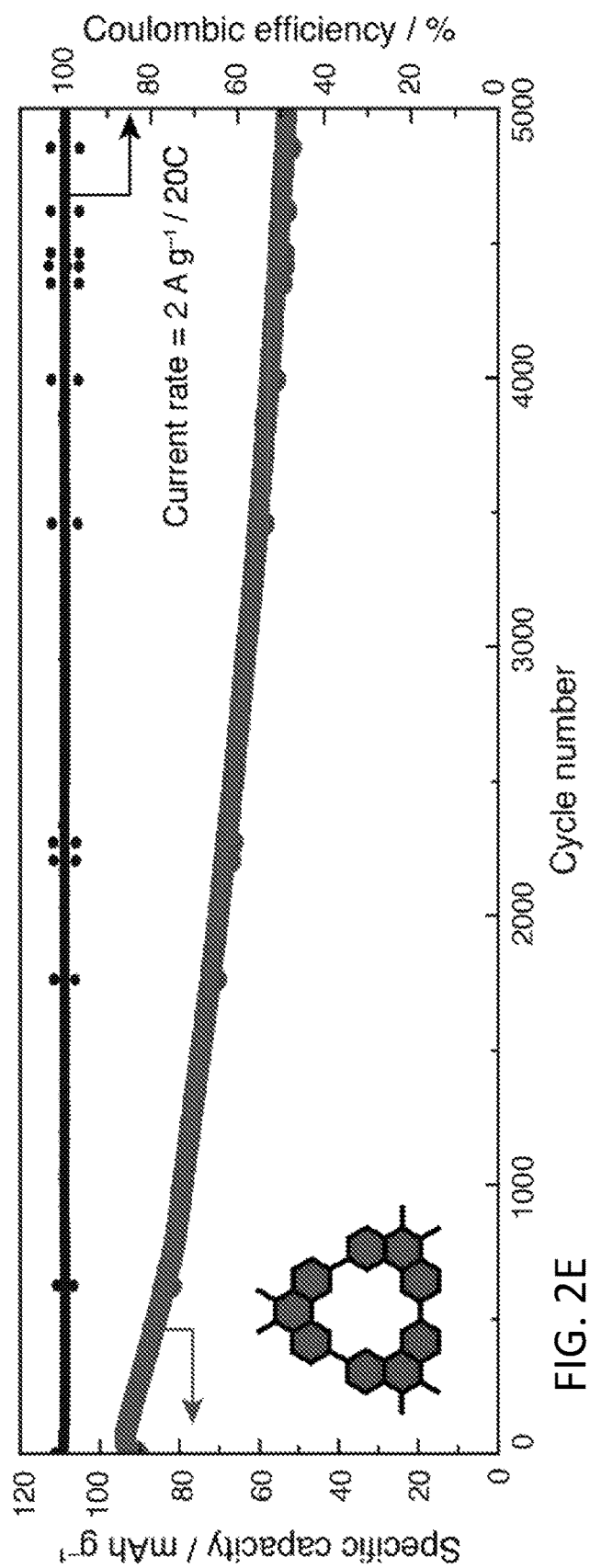
Figure 8A:
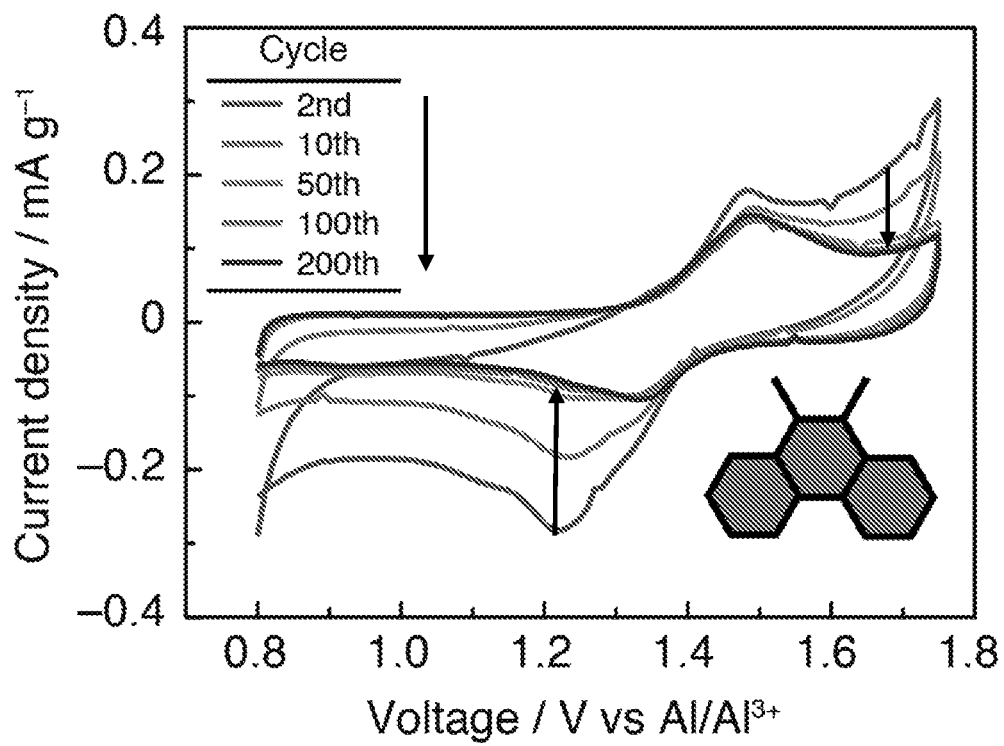
FIGS. 8A-8C show cyclic voltammetry profiles.
Figure 8B:
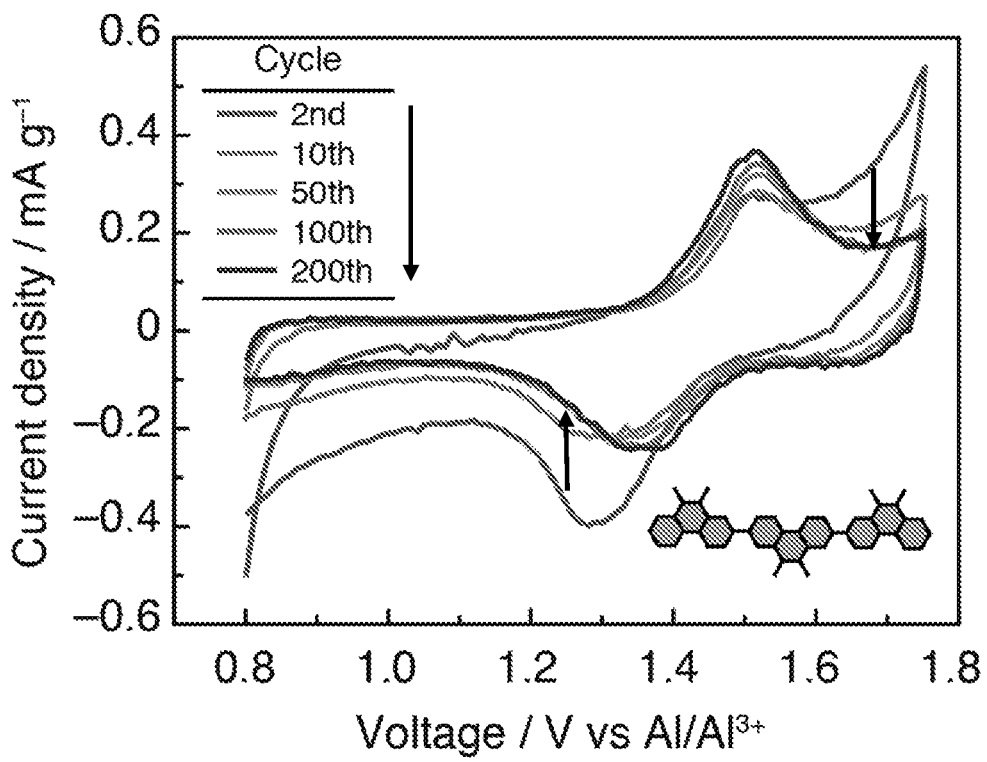
Figure 8C:
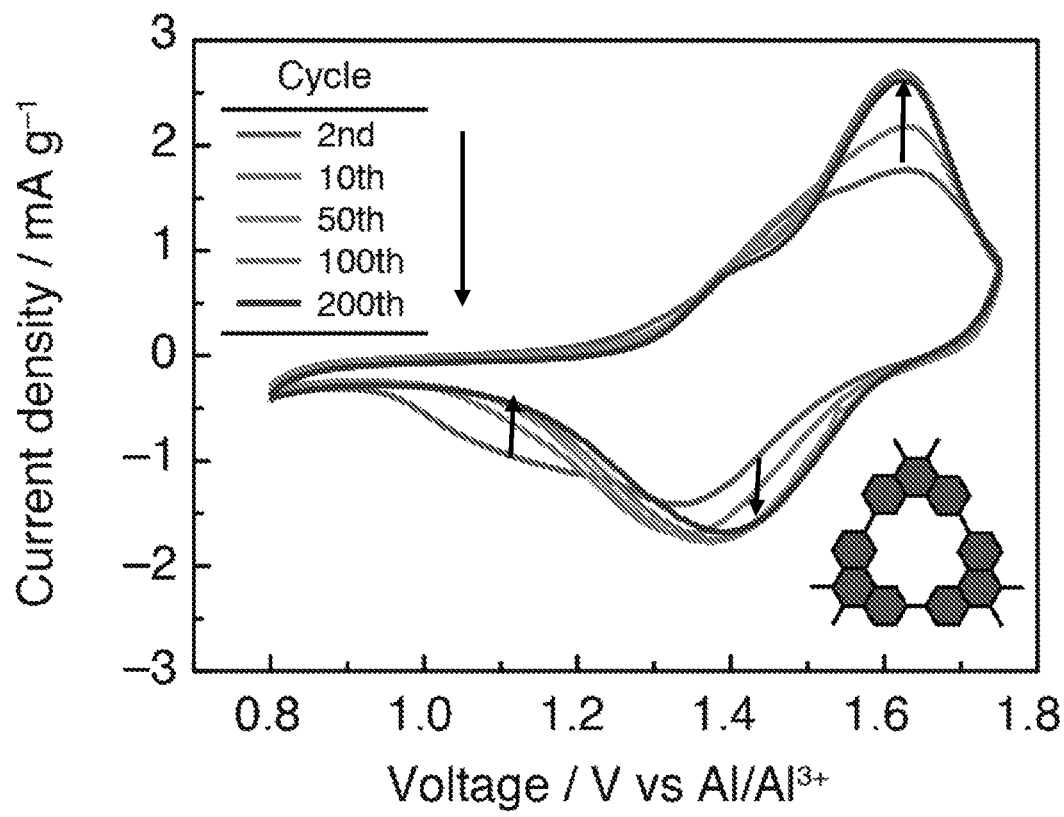
Figure 9A:
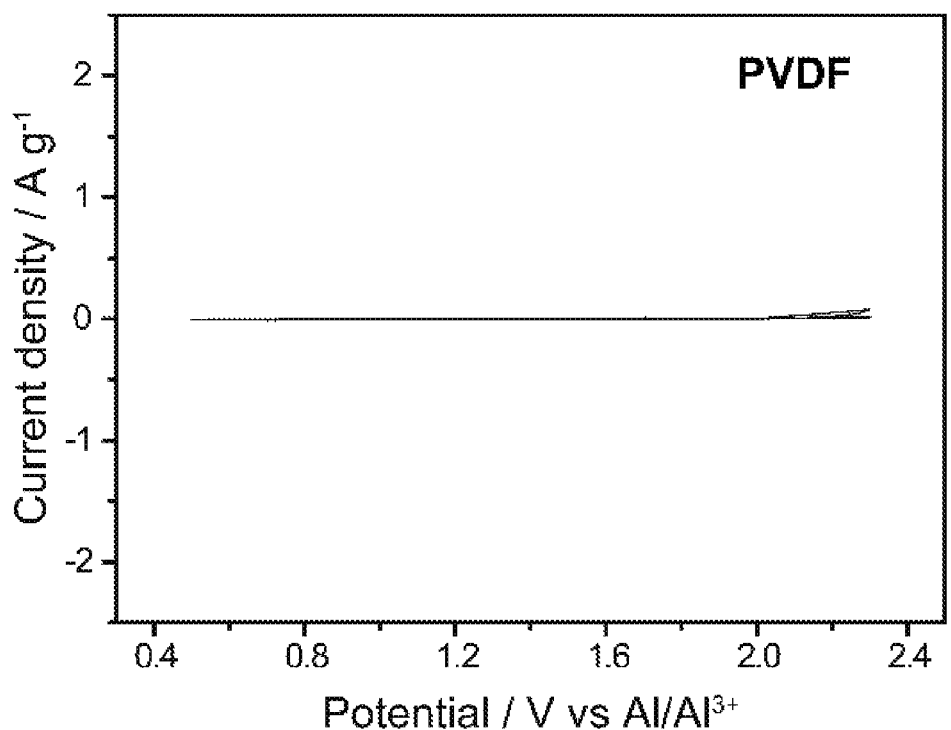
FIGS. 9A-9B show cyclic voltammetry profiles.
Figure 9B:
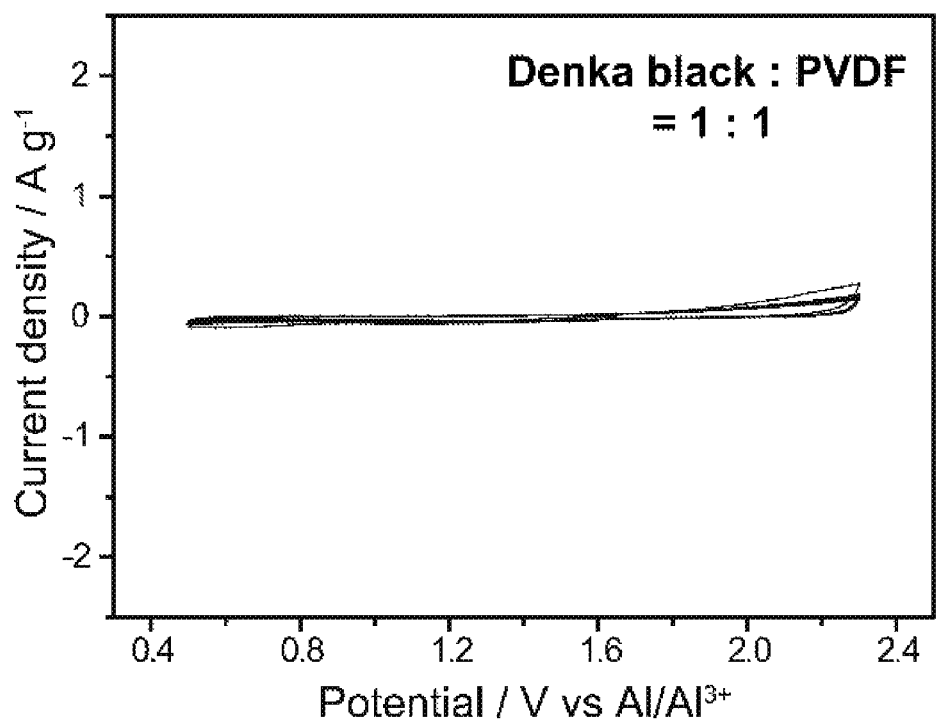
Figure 10A:
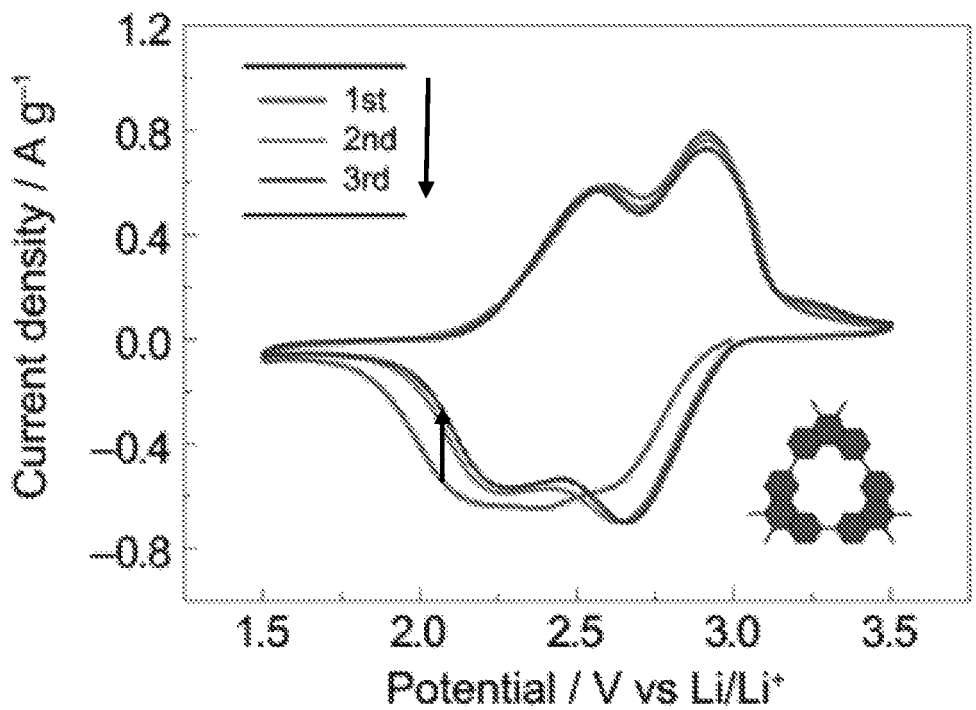
FIGS. 10A-10C show the CV and galvanostatic measurement of PQ-Δ in lithium-ion battery configuration. Both measurements were performed using coin-type cell and the active electrode was composed of PQ-Δ, carbon black, and PVDF in a weight ratio of 3:5:2.
Figure 10B:
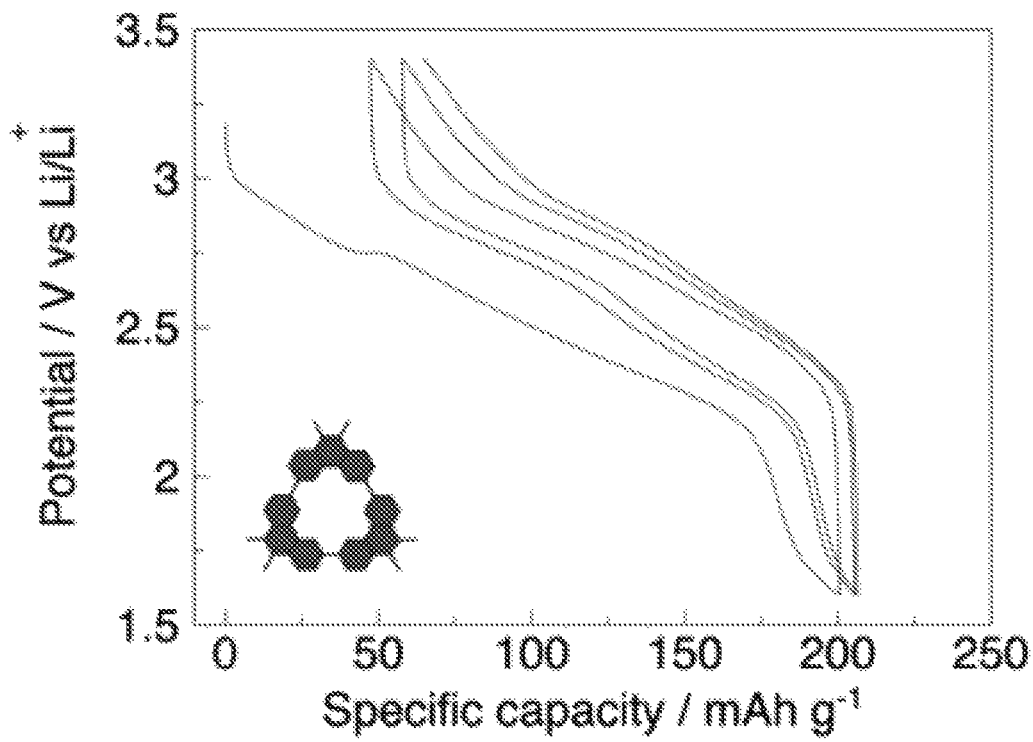
Figure 10C:
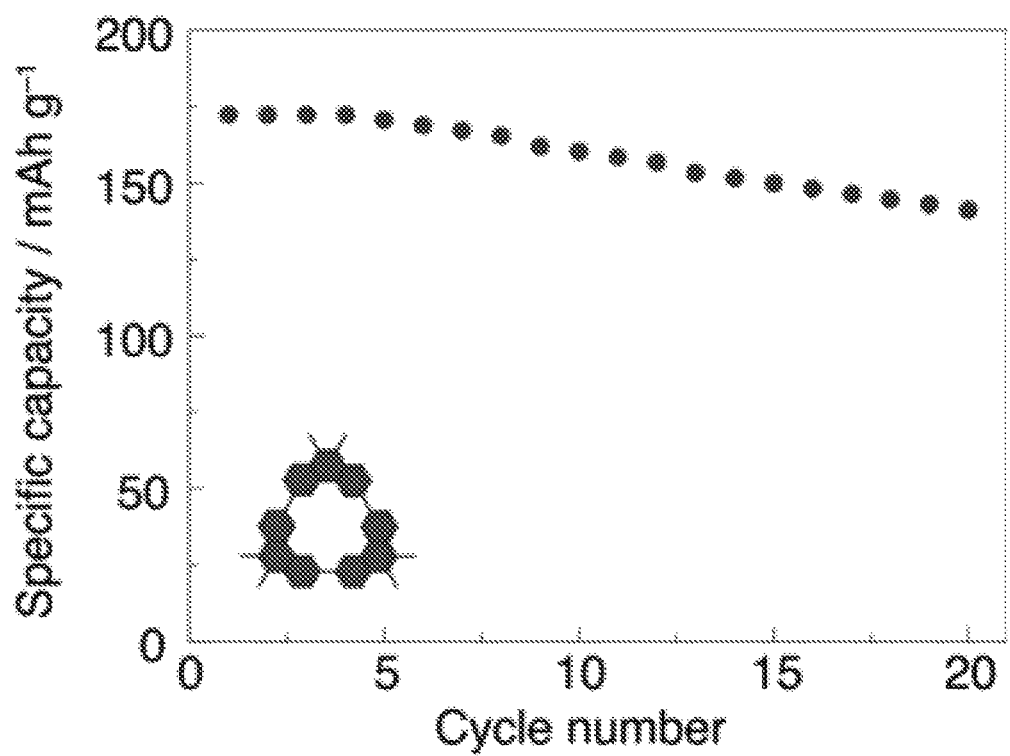
Figure 20:
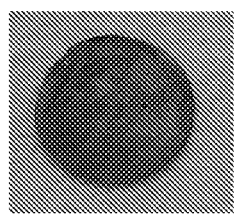
FIG. 20 shows the photograph of the separators of PQ-Ref, PQ-Lin, and PQ-Δ cells after 50 cycles of cyclic voltammetry.
Figure 20:
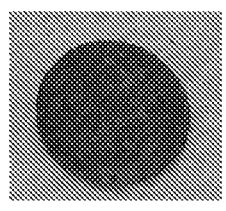
Figure 20:
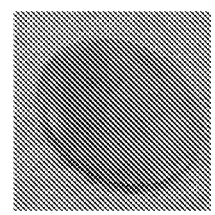

Based on the established stable voltage range for the electrolyte and current collector in the ALB environment, we subsequently carried out CV measurements on PQ-Ref, PQ-Lin and PQ-Δ in the voltage range of 0.70-1.75 V. All PQ derivatives exhibited (FIG. 2A) one pair of reversible reduction and oxidation peaks around 1.3 and 1.5 V, respectively. It is worth mentioning that the current density of PQ-Ref and PQ-Lin decreased gradually with each cycle (FIG. 8A-B), an observation which we ascribe to the gradual dissolution (FIG. 20) of the active materials in the electrolyte. For PQ-Δ, however, the current density increased gradually (FIG. 8C) during extended cycles. This current density increase could be a result of microstructural rearrangements in PQ-4, which increases the activity of PQ-Δ during cycles.[29] After observing the reversible redox nature of PQ derivatives in the ALB system, we carried out galvanostatic measurements of PQ-Ref, PQ-Lin, and PQ-Δ as the active materials of ALBs. Theoretical specific capacities and C-rate (C) were calculated based on a 1:1 ratio of PQ:chloroaluminate, while the charge and discharge processes refer to the oxidation (Al-complex ion extraction) and reduction (Al-complex ion insertion), respectively. At a current rate of 0.2 A g$^{-1}$, PQ-Ref and PQ-Lin showed (FIG. 2B) a single smooth plateau around 1.2-1.6 V for both discharging and charging, with specific capacities of 15 and 20 mAh g$^{-1}$, respectively. In the case of PQ-Δ, the triangular macrocycle displayed a similar voltage profile with the substantially increased reversible capacity of 94 mAh g$^{-1}$ under identical measurement conditions. It is worth mentioning that the specific capacities obtained correspond to one-electron transfer per Al-complex ion, not three electrons. Previous reports[18, 30] have revealed that soluble halides of group 13 elements undergo asymmetric cleavage in solution, generating $[MX_2]^+$ and $[MX_4]^-$ ions. Thereafter, the cationic complex reacts with the radical anion of the PQ, resulting in a single electron transfer.[30, 31, 32] This observation raises the possibility of PQ-$\Delta^{3\bullet-}$ interacting also with the cationic aluminum complex ($AlCl_2^+$), comprising the stable tetracoordinate centers ((PQ-$\Delta^{3*}$)·3$AlCl_2$) with both quinone oxygens chelating one aluminum center.[19] Upon discharging, the macrocycle (PQ-$\Delta$) (FIG. 1B) is reduced to its semiquinone state (PQ-$\Delta^{3\bullet-}$), followed by interacting with the cationic chloroaluminates ($AlCl_2^+$), which were generated by the asymmetric cleavage of dialuminum hexachloride, resulting in the formation of the tetracoordinate complex, (PQ-$\Delta^{3*}$)·3$AlCl_2$ (FIG. 1D). Because of the formation of a strong cationic aluminum complex, we suspect that PQ derivatives cannot be fully reduced to a dianionic state in the ALB system, an observation which is consistent (FIG. 2A) with the CV results. More recent research from the battery standpoint by Kravchyk et al.[33] has also confirmed that bare aluminum-ion does not directly engage in intercalation by means of electrochemical redox in an imidazolium chloride-based electrolyte environment, but rather chloroaluminate anions, such as $AlCl_4^-$ and $Al_2Cl_7^-$, express the redox processes. Our electrochemical results suggest strongly that the cationic chloroaluminate migrates through the PQ-$\Delta^{3\bullet-}$, therefore enabling reversible intercalation. The use of the cationic carrier ions in the cathode reactions is more beneficial in energy density that takes the amount of electrolyte into account, compared to typical Al-complex ion batteries where anionic carrier ions are used for cathode reactions. When all three compounds were subjected to galvanostatic cycling tests at a current rate of 0.2 A $g^{-1}$ (FIGS. 2B-C), PQ-$\Delta$ displayed an excellent capacity retention of 82 mAh $g^{-1}$ after 200 cycles, corresponding to 100.9% retention with respect to that observed in the first cycle. This specific capacity, after 200 cycles, is compared with 17 mAh $g^{-1}$ for PQ-Lin and 13 mAh $g^{-1}$ for PQ-Ref. This substantial capacity retention of PQ-$\Delta$ suggests that the macrocyclic constitution restricts the rotational possibility between neighboring PQ moieties under these electrolyte conditions which minimizes the solvation event in the presence of the battery electrolyte.[34] We have also investigated the ALB performance of PQ-$\Delta$ and found that it displays (FIG. 2D) an excellent rate capability, which could originate from its conjugated molecular constitution. PQ-$\Delta$ exhibited a specific capacity of 110 mAh $g^{-1}$ at a current rate of 0.1 A $g^{-1}$. When the current rate was increased up to 100 times (10 A $g^{-1}$), a specific capacity of 70 mAh $g^{-1}$ was still observed, indicating the extraordinary rate capability of PQ-$\Delta$. This rate performance is attributed to well-defined ion channels along the π-π stacked superstructure of PQ-$\Delta$. Also, PQ-$\Delta$ maintained excellent capacity retention (95 mAh $g^{-1}$) when the current rate was decreased back to 0.5 A $g^{-1}$. The discrepancy in the specific capacities at 2 C between FIGS. 2C and 2D is attributed to different degrees of activation of PQ-$\Delta$; in the rate capability test in FIG. 2D, the preceding cycles at 0.1 C are likely to activate PQ-$\Delta$ more significantly and thus increase the specific capacity. Since the cycle life is of primary importance for large-scale energy storage applications, we then subjected PQ-$\Delta$ to extensive cycling performance testing (FIG. 2E). The macrocycle preserved 53 mAh $g^{-1}$ after 5000 cycles, corresponding to a capacity fade of only 0.0082% for each cycle. This remarkable cycling performance highlights the robustness of the molecular triangle and the reversible accessibility of cationic chloroaluminate throughout galvanostatic cycling.

Ex-Situ Characterization of PQ-$\Delta$ Electrode

Figure 3A:
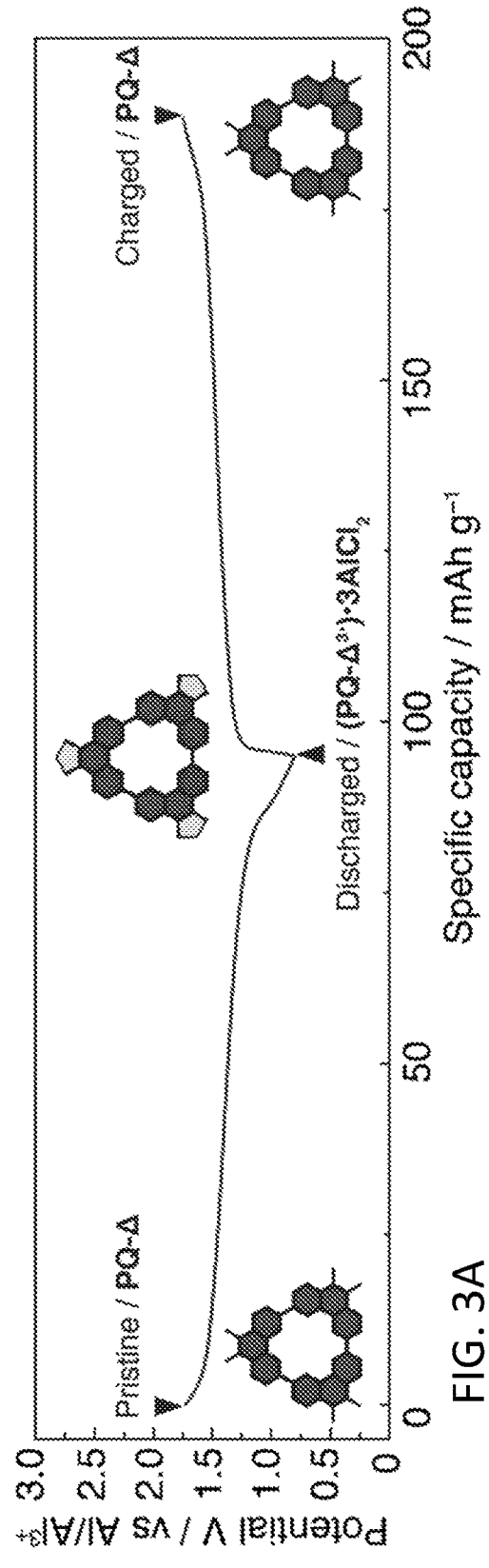
FIGS. 3A-3E show the ex-situ characterizations of PQ-Δ.
Figure 3B:
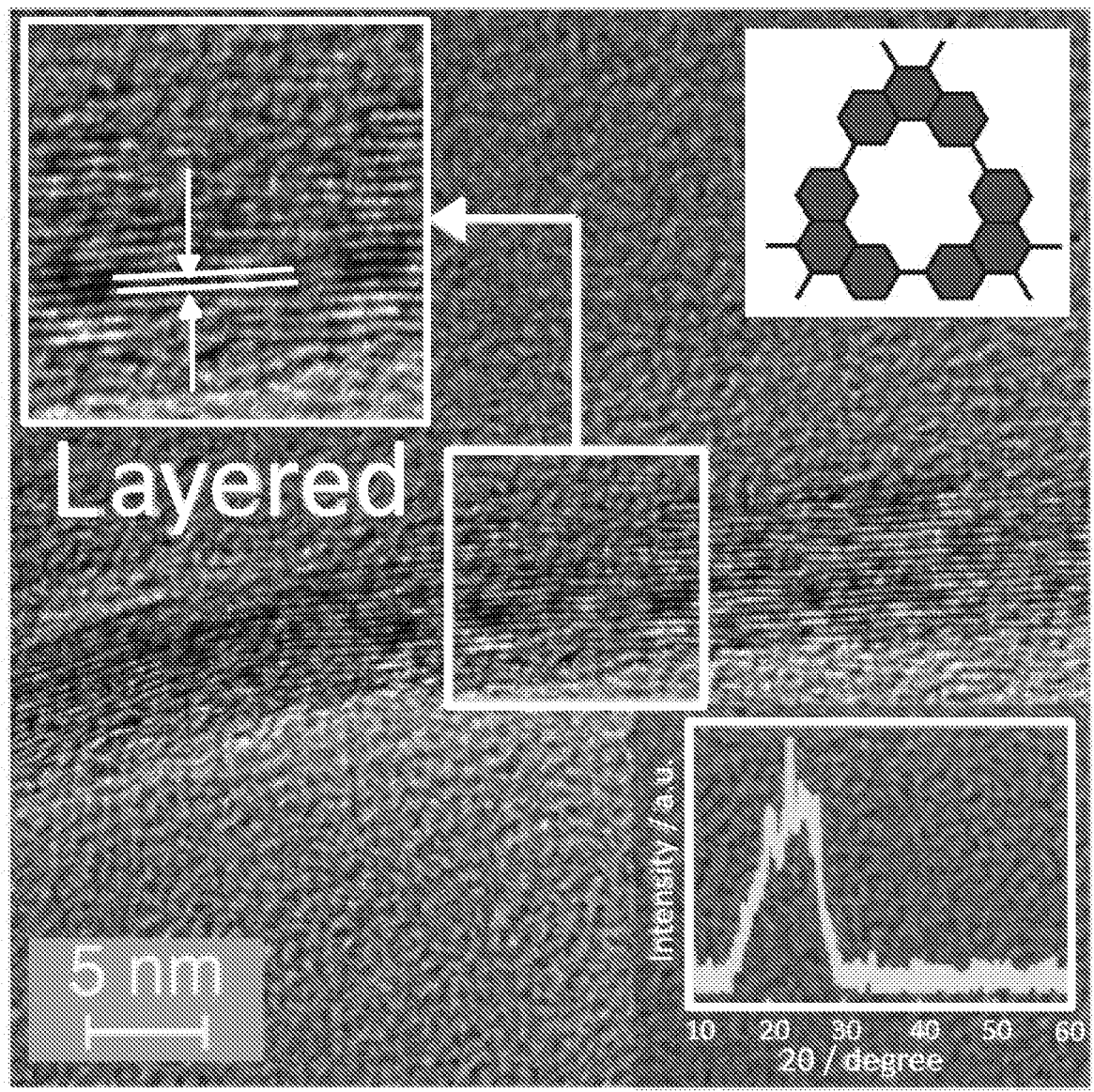
Figure 3C:
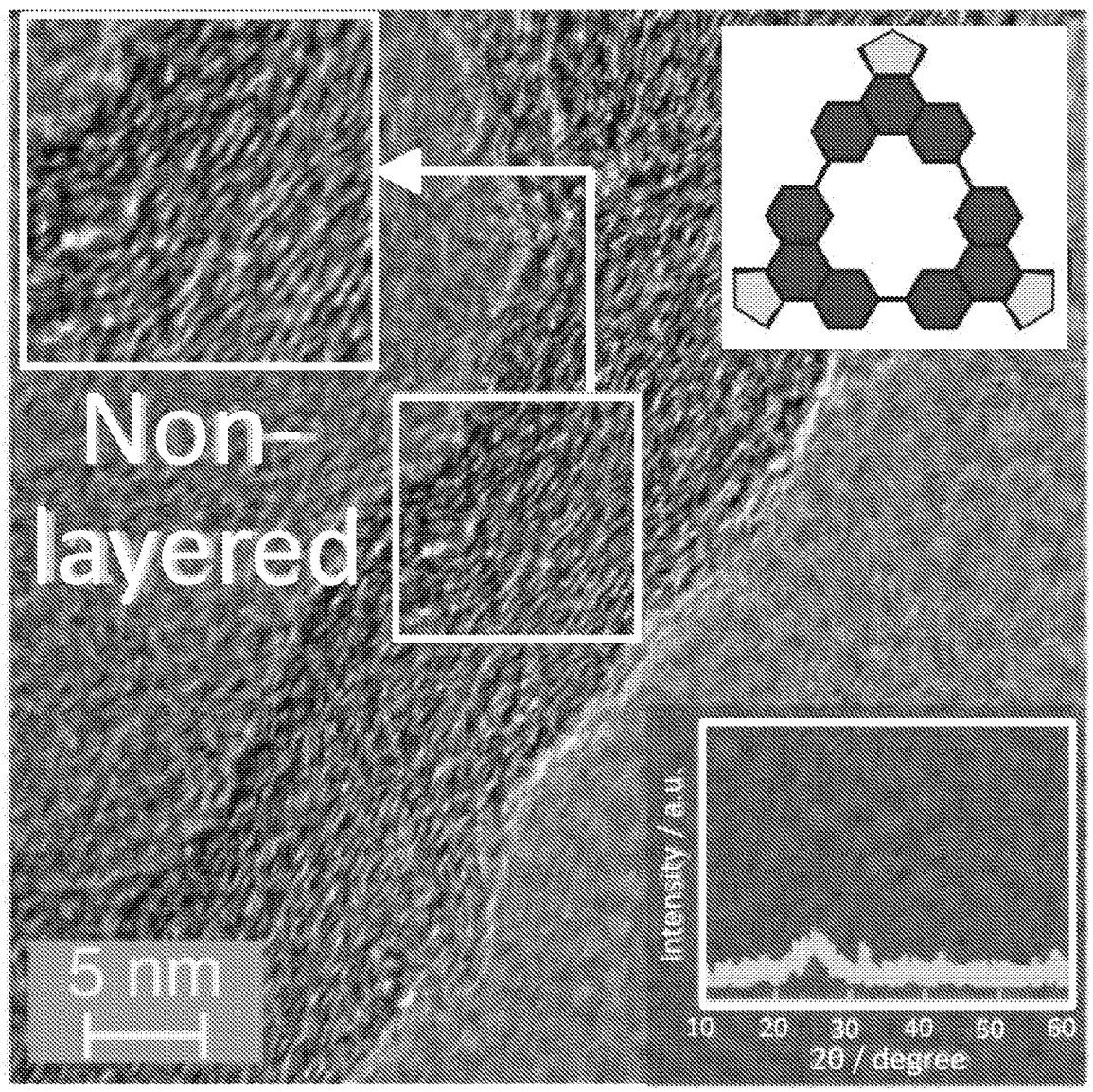
Figure 3D:
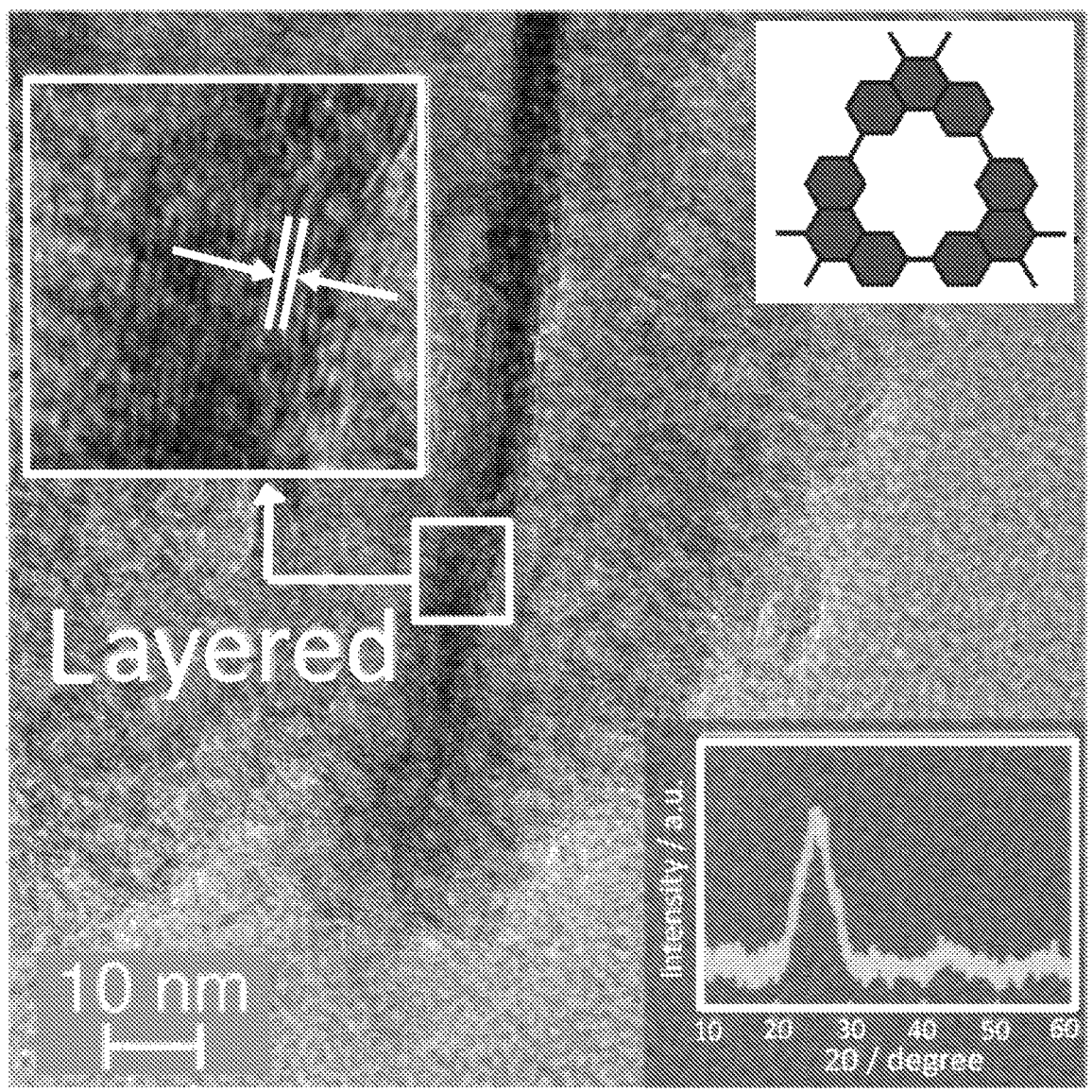
Figure 3E:
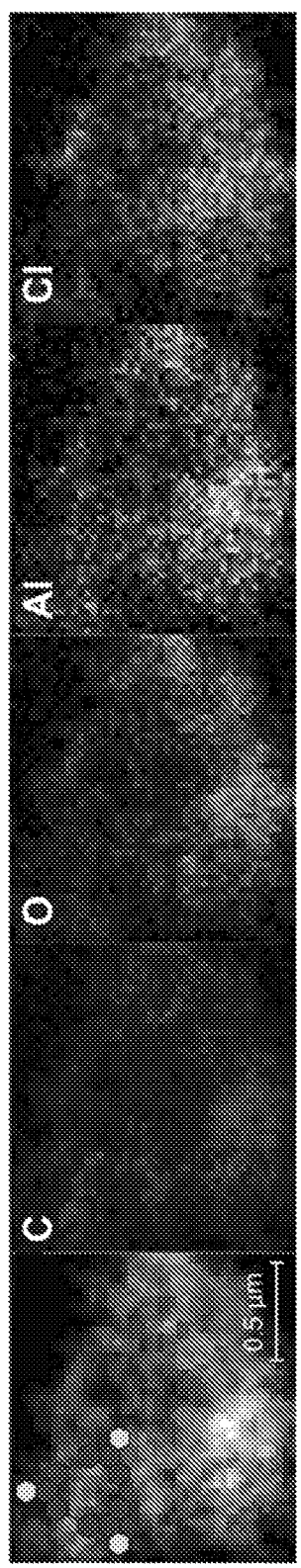
Figure 16:
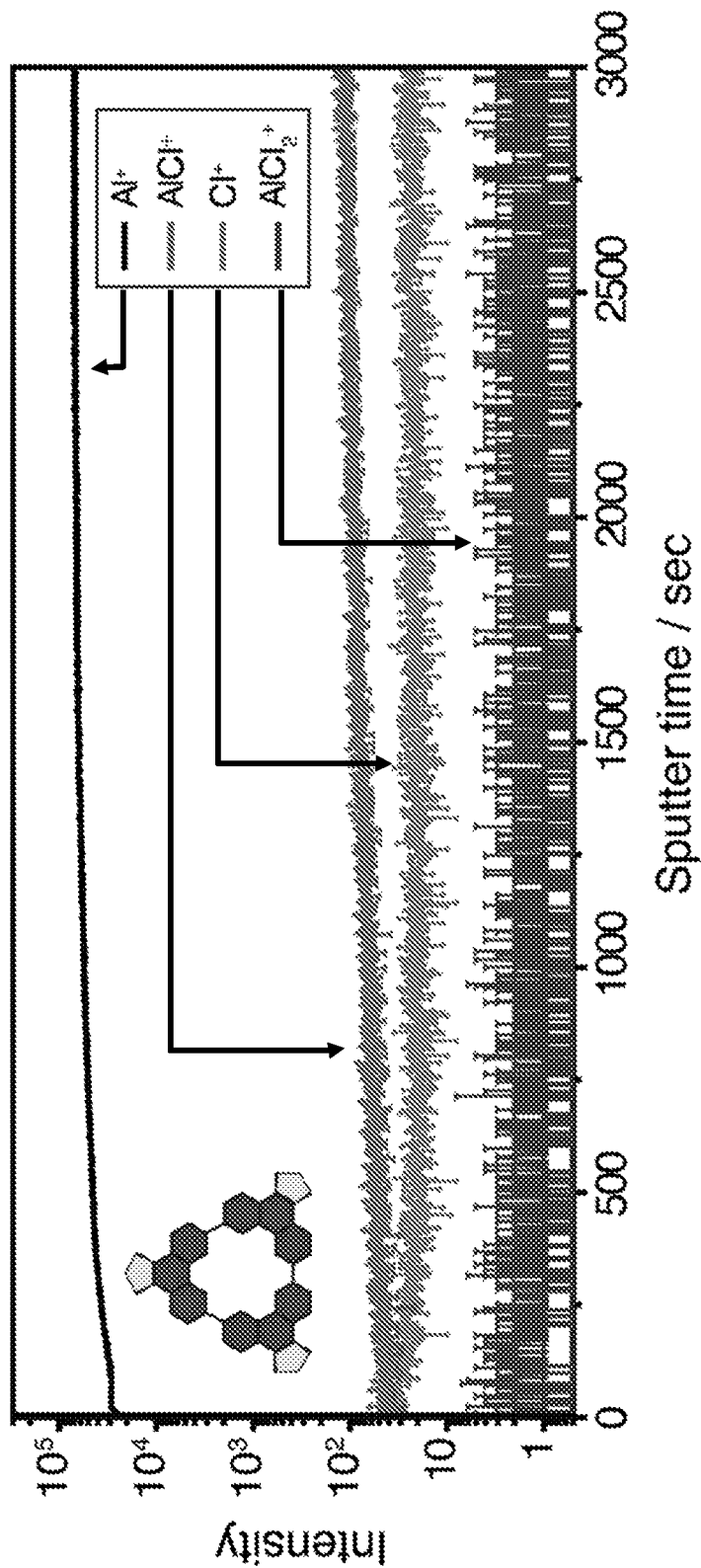
FIG. 16 shows the ToF-SIMS spectra of the discharged PQ-Δ electrode.
Figure 19A:
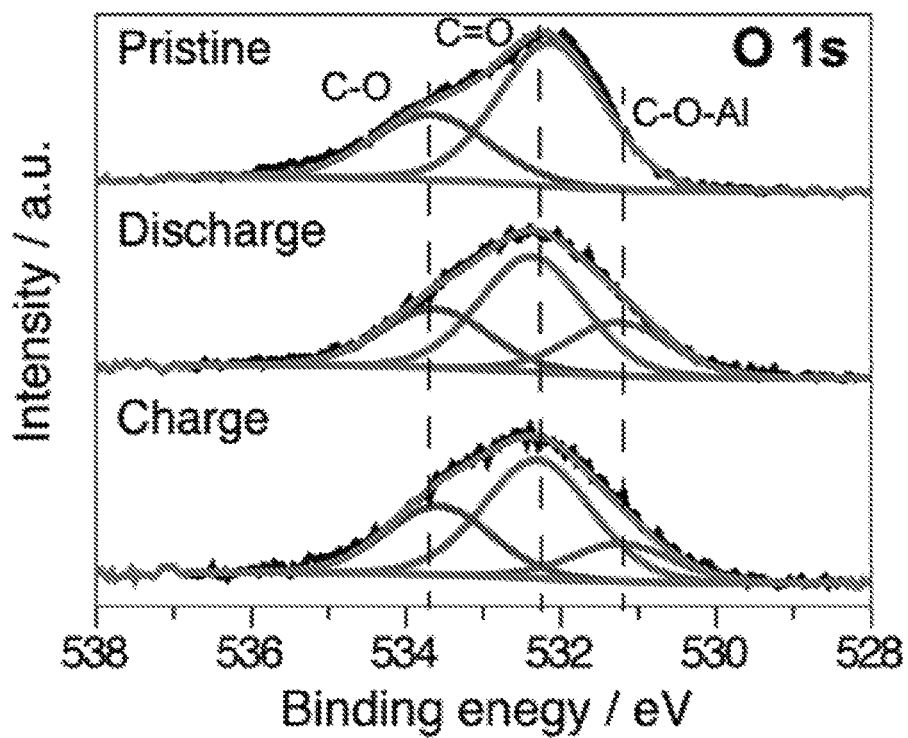
FIGS. 19A-19B show the XPS Spectra of pristine, discharged, and charged PQ-Δ electrodes.
Figure 19B:
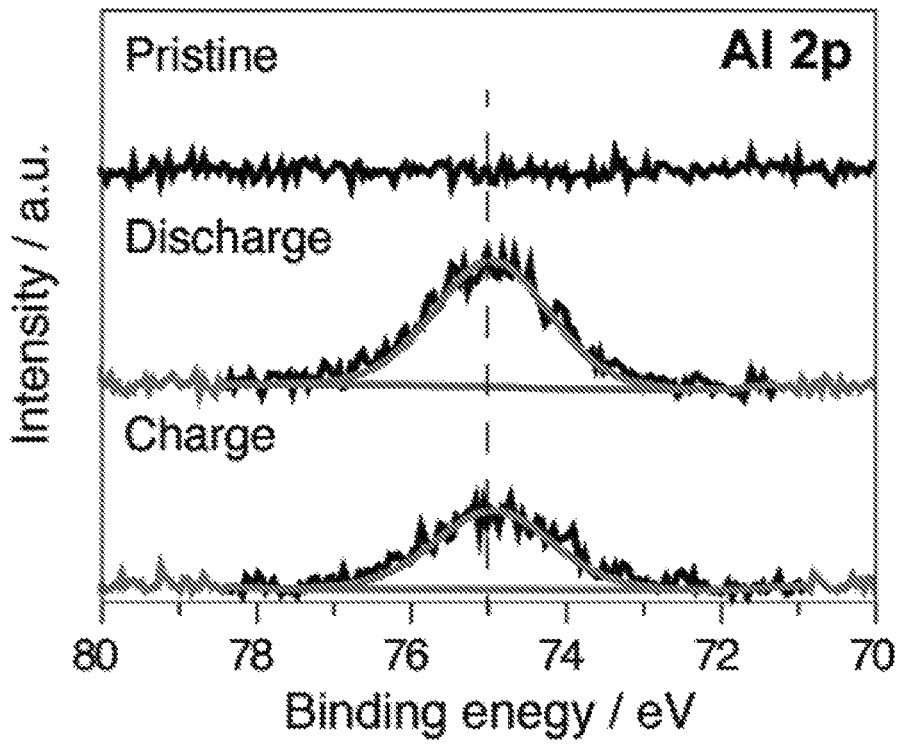

In order to assess the intercalation of chloroaluminate in PQ-$\Delta$ during battery cycling, we analyzed PQ-$\Delta$ electrodes by using both ex-situ PXRD and transmission electron microscopy (TEM). Detailed ex-situ sample preparations are described in the Examples. All of the ex-situ analysis samples were collected after neutral state, charging or discharging, followed by disassembling inside of the glove box. The galvanostatic voltage profile of PQ-$\Delta$, as well as the schematic for each ex-situ state is illustrated in FIG. 3A. According to PXRD analysis, the amorphous layered superstructure of PQ-$\Delta$ is carried over into the battery electrode fabrication. We observed once again in the electrode material a diffraction peak around 2θ=22-28°, which corresponds (inset in FIG. 3B) to a layer-to-layer distance of 0.36 nm. This layered superstructure (FIG. 3B) of pristine PQ-$\Delta$ was confirmed by TEM analysis. In the discharged state, ex-situ PXRD diffraction showed (inset in FIG. 3C) peak broadening as a result of the insertion of chloroaluminate ions between the PQ-$\Delta$ layers, causing (FIG. 3C) physical distortion of the stacked superstructure.[35] As indicated by PXRD diffraction analysis (inset in FIG. 3D), the stacking structure (FIG. 3D) and PXRD diffraction peak (inset of FIG. 3D) was restored to its neutral state, resulting in the extraction of chloroaluminate from the electrode. Furthermore, we conducted time-of-flight secondary ion mass spectrometry (ToF-SIMS) on the discharged electrode along with energy-dispersive X-ray spectroscopy (EDX), in order to investigate the elemental composition of the discharged PQ-$\Delta$. The mass spectrum of the discharged electrode exhibits (FIG. 16) the signal corresponding to cationic chloroaluminates, whereas EDX verifies (FIG. 3E) the presence of both aluminum and chlorine. These two analytic techniques taken together make it reasonable to adopt the insertion of $AlCl_2^+$ toward PQ-$\Delta$ electrode. In addition, we performed ex-situ X-ray photoelectron spectroscopy (XPS) analysis on the discharged electrode. This analysis indicates (FIGS. 19A-19B) that the O 1s edge shifted to a lower energy after discharging on account of the decreased oxidation state of the quinone group. After charging, the O 1s edge was restored to its pristine state. Taken together, ex-situ studies of PQ-$\Delta$ provide a valuable insight into the reversible intercalation of chloroaluminate within the wet electrolyte environment.

Fabrication of Hybrid Electrode and Battery Performances

Figure 4A:
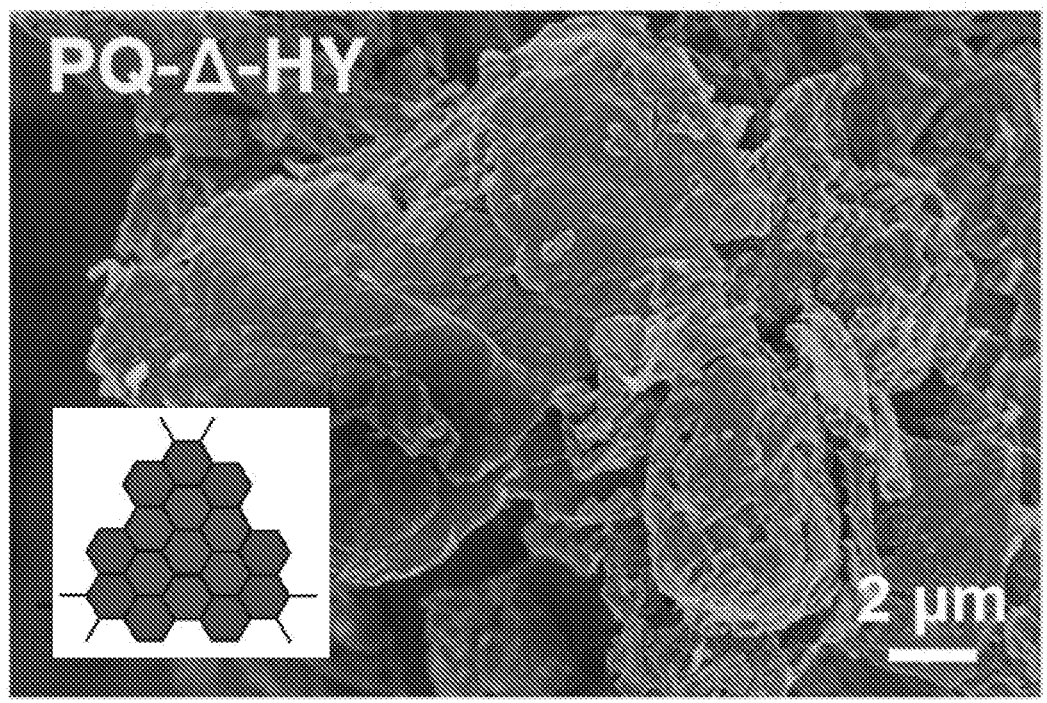
FIGS. 4A-4E show the fabrication of the graphite flake-blended phenanthrenequinone triangle hybrid (PQ-Δ-HY) and its electrochemical performance. Equal weight (1:1 w/w) of PQ-Δ and graphite flakes were used to fabricate the PQ-Δ-HY.
Figure 4B:
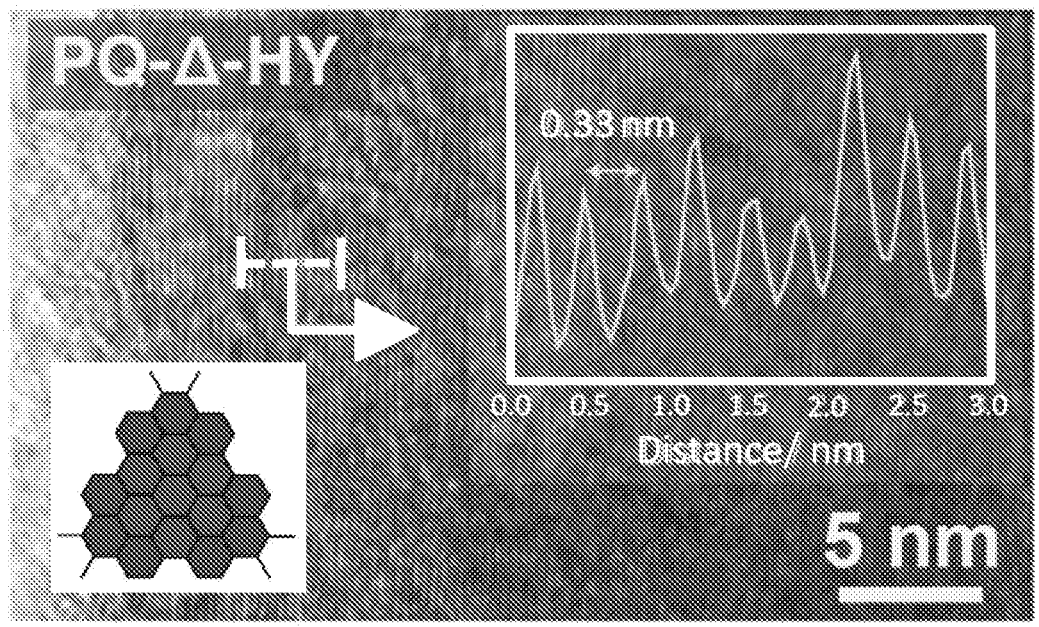
Figure 4C:
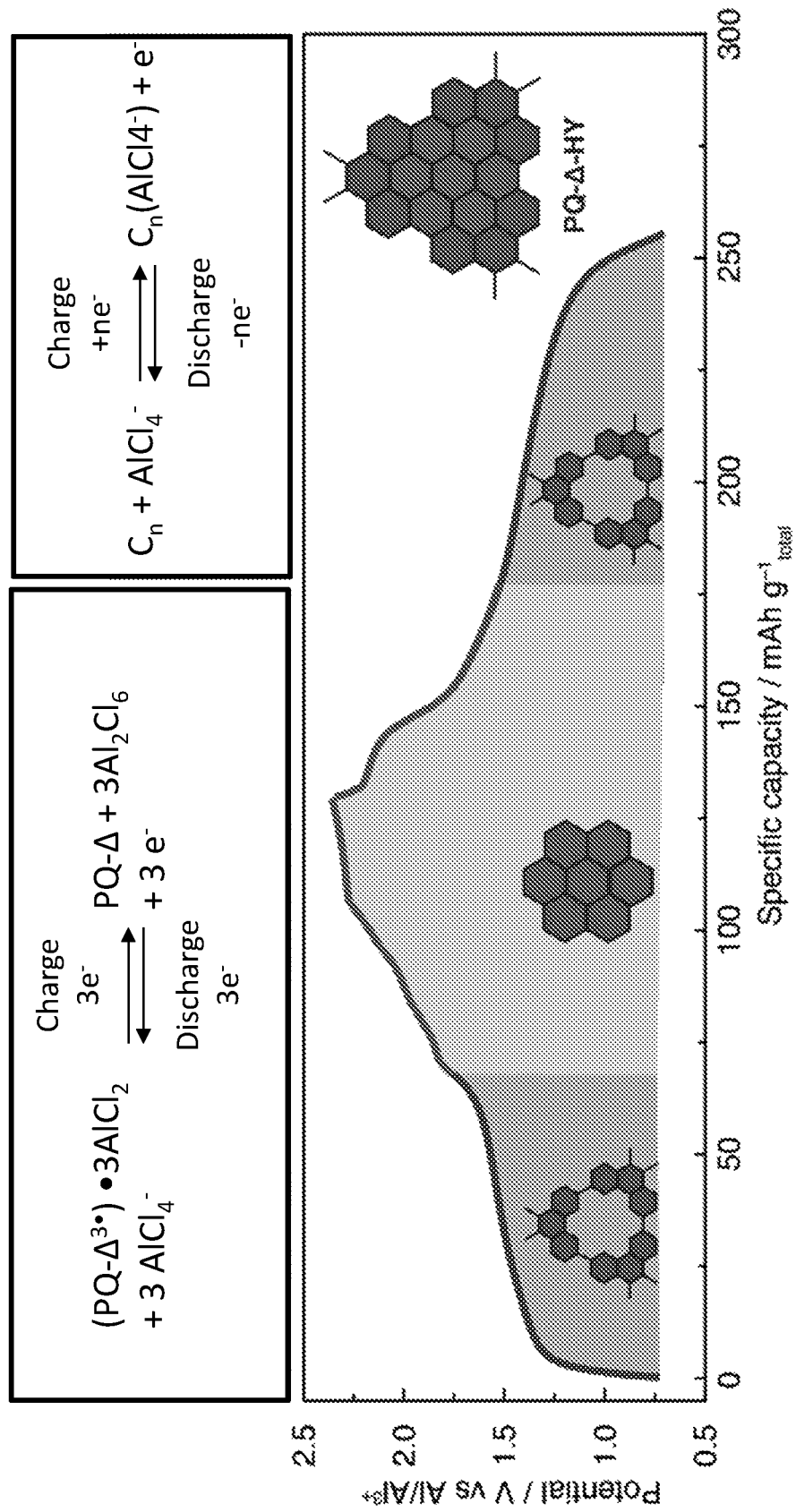
Figure 4D:
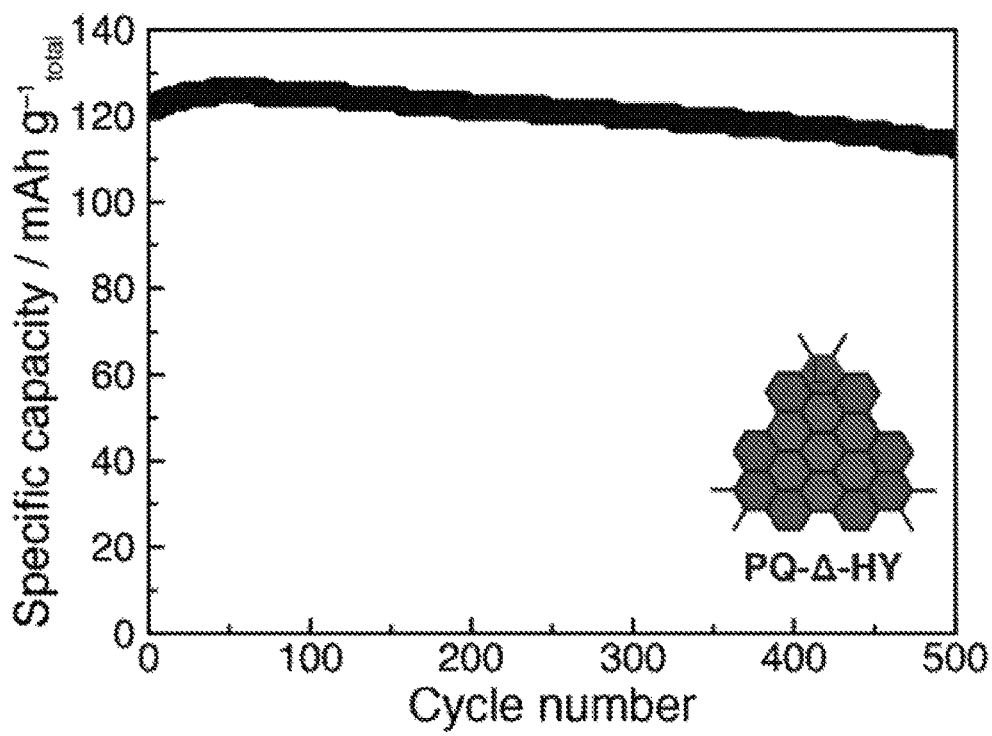
Figure 4E:
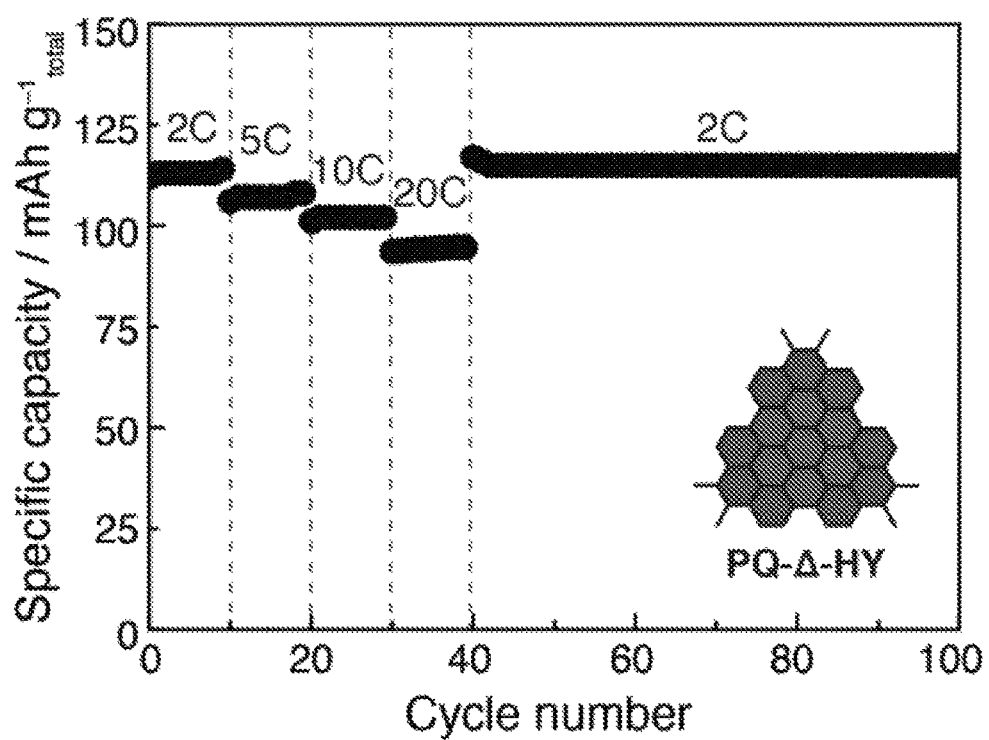
Figure 11A:
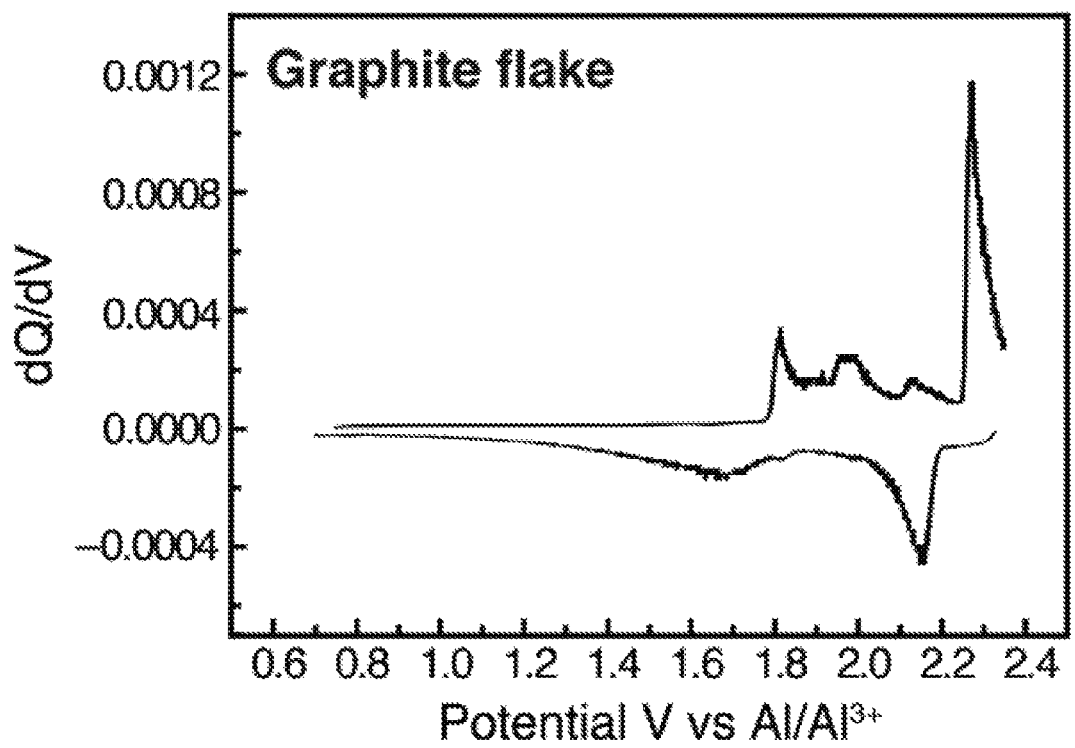
FIGS. 11A-11B show the voltage versus differential capacity plot.
Figure 11B:
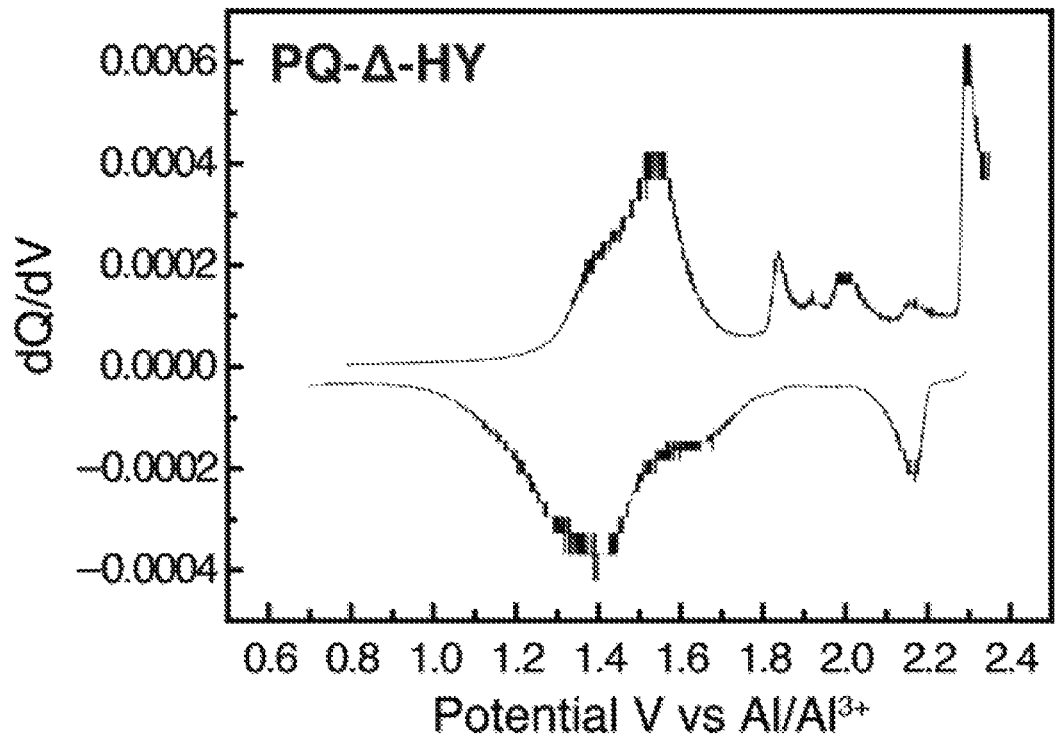
Figure 12:
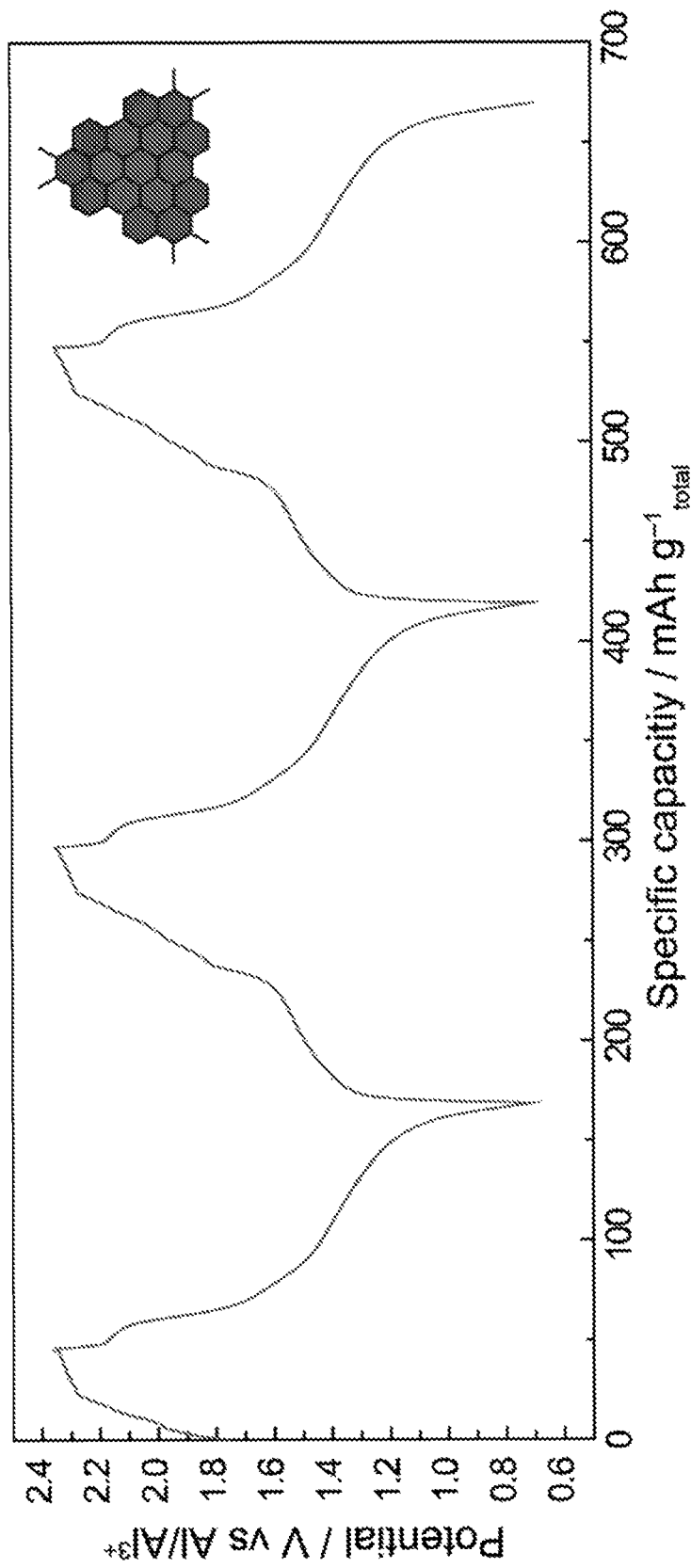
FIG. 12 shows the galvanostatic voltage profile of PQ-Δ-HY for the first three cycles.
Figure 13A:
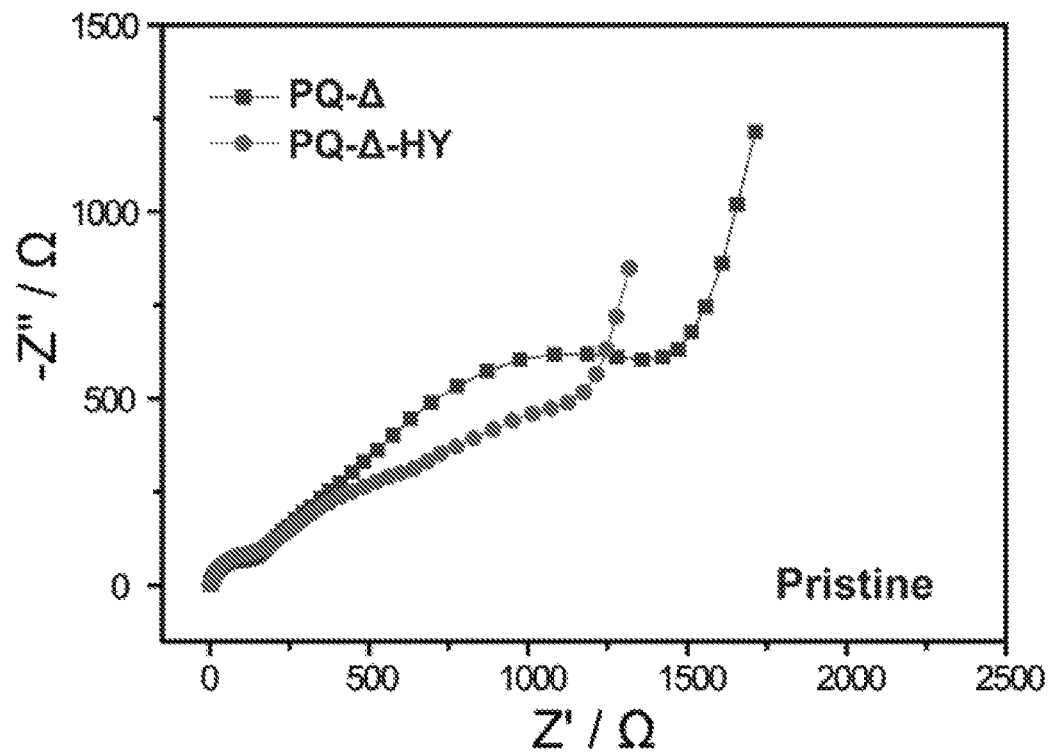
FIGS. 13A-13B show the EIS results of PQ-Δ and PQ-Δ-HY electrodes.
Figure 13B:
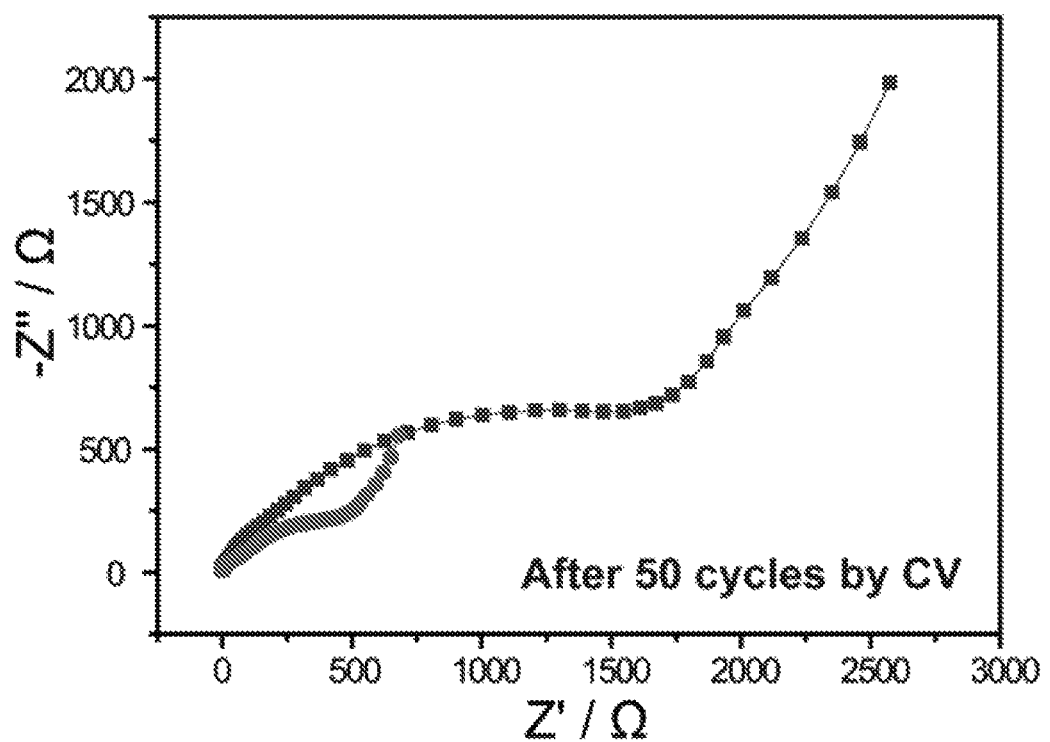
Figure 18A:
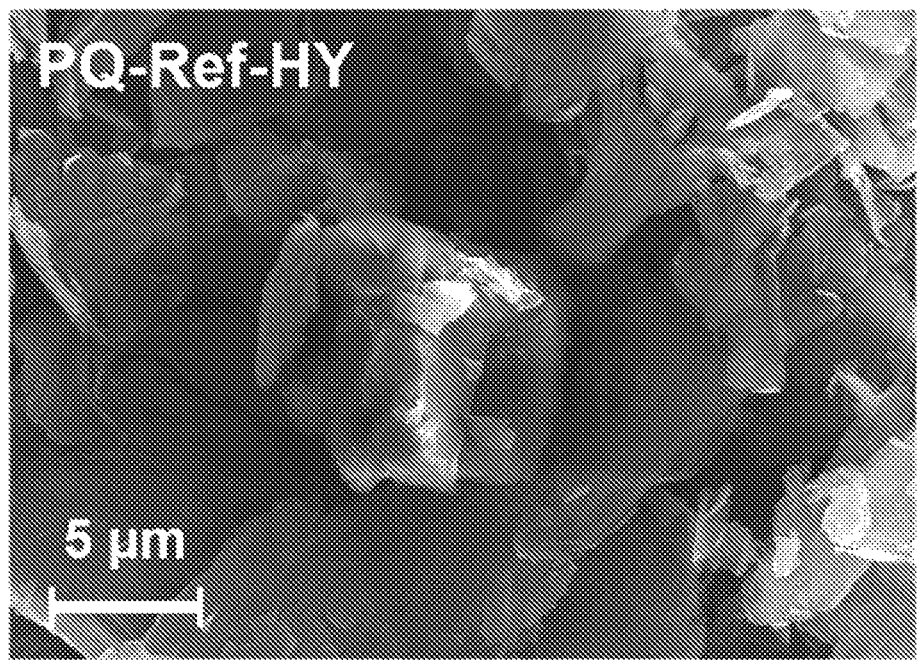
FIGS. 18A-18C show an SEM image and EDX mapping of PQ-Ref-HY.
Figure 18B:
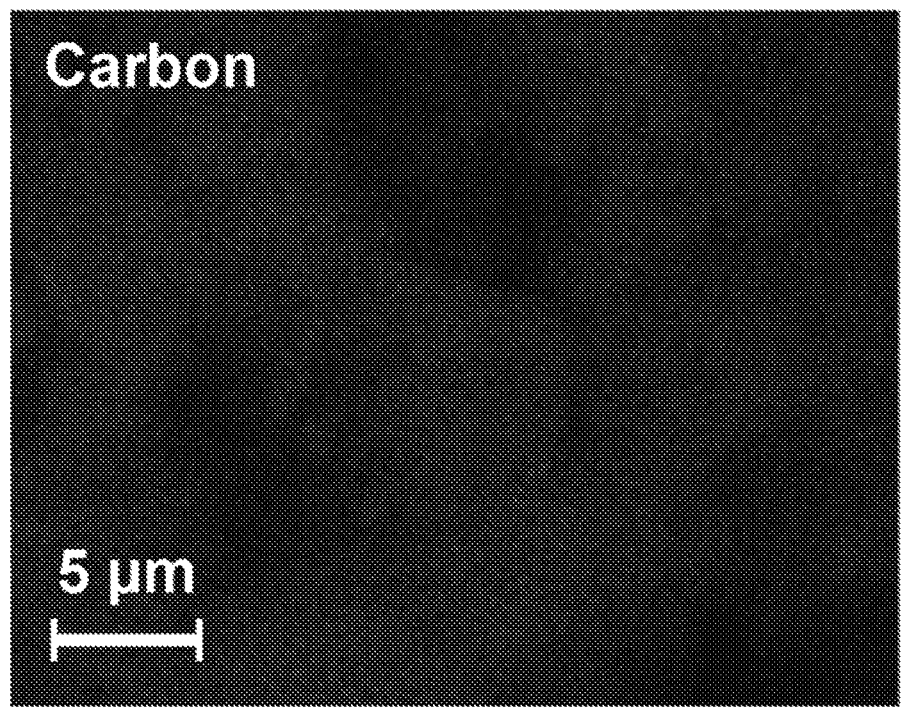
Figure 18C:
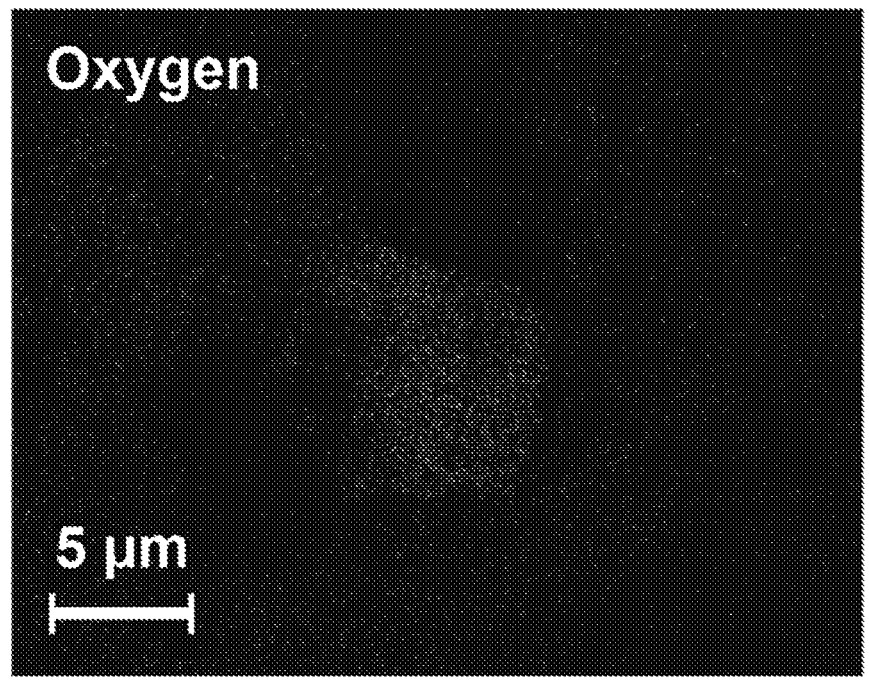

The exceptional cyclability of PQ-$\Delta$ as the active material for ALBs, encouraged us to enhance its feasibility in a practical electrode setting by designing a hybrid electrode with graphite flakes. In previous reports, Dai et al.[28] demonstrated a graphite flake-based, ALB showing excellent cyclability and power capability. Recently, Kravchyk et al.[33] investigated the detailed mechanism of chloroaluminate anion insertion into graphite flakes. Noticeably, we recognized (FIGS. 8A-C and 11A-B) the redox potential differences between PQ-$\Delta$ (1.4 V vs Al/$Al^{3+}$) and graphite flakes (1.8 V vs Al/$Al^{3+}$), attributed to the different types of chloroaluminate ions engaged in each compound. Thus, by taking advantage of the redox potential differences and the planar geometry of PQ-$\Delta$, we have fabricated a graphite flake-blended phenanthrenequinone triangle hybrid (PQ-$\Delta$-HY) electrode. The highlight of this hybrid composition is that the graphite flakes, not only increase electronic conductivity as the conductive agent, but also serve as the active material along with PQ-$\Delta$ in the higher voltage range. It is worth noting that the exclusive use of redox-active organic compounds is usually impractical in high-loading electrodes because of their poor electronic conductivity and unstable stacking architecture. In order to overcome the insufficient electronic conductivity, organic-based electrodes frequently require a considerable amount of conductive carbon filler, such as carbon black[36], carbon nanotubes[37], or graphene.[38] While adding carbon fillers apparently enhances the conductivity of the electrode, it decreases the energy density of the battery cell on account of the small active mass content. Moreover, addition of carbon fillers does not resolve the issue of limited electrode loadings. In our investigation, PQ-Δ-HY was prepared by sonicating an equal molar weight of PQ-Δ and graphite flake using N-methyl-2-pyrrolidone as the solvent. Detailed electrode preparation procedures are described in the Examples. The formation of a PQ-Δ-HY superstructure was confirmed by scanning electron microscopy SEM (FIG. 4A) and TEM (FIG. 4B), indicating the homogeneous stacking of PQ-Δ and graphite flakes. For the control experiment, we attempted to fabricate the hybrid electrode using PQ-Ref and graphite flakes. We could not, however, achieve a similar morphology (FIGS. 18A-C), implying the importance of the constitution and geometry of the molecules. The electrochemical behavior of PQ-Δ-HY displays a unique combination of PQ-Δ and graphite flakes, which is similar to the previously reported[39, 40] bipolar battery system. From the voltage versus the differential capacity plot (FIGS. 11A-11B), the oxidation and reduction peaks are confirmed at 1.55, 1.83-2.15 V and 1.40, 2.15 V, respectively. These multiple redox peaks can be attributed to the co-existence of PQ-Δ and graphite flakes within a single electrode, and the potential values are consistent with our earlier results (PQ-Δ, FIG. 8C) and previous graphite flake reports[28, 41]. We have confirmed (FIG. 4C) the two-stage redox behavior in galvanostatic measurements of PQ-Δ-HY. PQ-Δ exists in the reduced form of $(PQ-\Delta^{3\bullet})\cdot 3AlCl_2$ in its fully discharged state (0.75 V), while the graphite flakes are present in their neutral state ($C_n$). For reference, the specific capacities of PQ-Δ-HY were calculated based on the weight of both PQ-Δ and graphite flake for the electrochemical evaluation of PQ-Δ-HY. Upon charging, oxidation of $(PQ-\Delta^{3\bullet})\cdot 3AlCl_2$ reveals one smooth plateau in the range of 0.75-1.75 V, with a specific capacity of 68 mAh g$^{-1}$ total. Additionally, PQ-Δ-HY could charge up to 2.35 V, through the oxidation of the graphite flakes, accompanied by the intercalation of $AlCl_4^-$, with the total specific capacity reaching 130 mAh g$^{-1}_{total}$. During discharge, this multi-step oxidation process is reversed. Notably, this specific capacity of 130 mAh g-total is greater than those of individual PQ-Δ-HY and graphite (110 and 80 mAh g$^{-1}$, respectively). This unexpected result can be explained by the fact that enhanced electronic conductivity in the PQ-Δ-HY electrode (FIGS. 13A-B) by the integration of the graphite increases the specific capacity of PQ-Δ. In fact, in the PQ-Δ-HY composite electrode, the capacity contributions at discharge from PQ-Δ and graphite were found to be 140 and 90 mAh g$^{-1}$, respectively, according to the differential capacity (dQ/dV) profile of PQ-Δ-HY (FIG. 11B). Remarkably, the observed 140 mAh g$^{-1}$ corresponds to the theoretical capacity of PQ-Δ, thus verifying the importance of electronic conductivity for the electrochemical activity of PQ-Δ. The cycling performance test of PQ-Δ-HY was also carried out (FIG. 4D) and again demonstrated excellent capacity retention, as 94% (114 mAh g$^{-1}_{total}$) of capacity was preserved after 500 cycles. We conducted (FIG. 4E) galvanostatic measurements by increasing the current rates, where PQ-Δ-HY exhibited excellent rate capability. When the initial current rate (0.2 A g$^{-1}$) was increased 2.5, 5, and 10 times, the hybrid electrode exhibited 94, 83, and 81%, respectively, of the initial specific capacity. In addition, we calculated specific energy and power, based on the total weight of electrode and electrolyte. The specific energy value is 69 or 32% higher than singularly composed electrodes of either the graphite flakes or PQ-Δ, demonstrating remarkable advances with high practical impact.

Figure 5A:
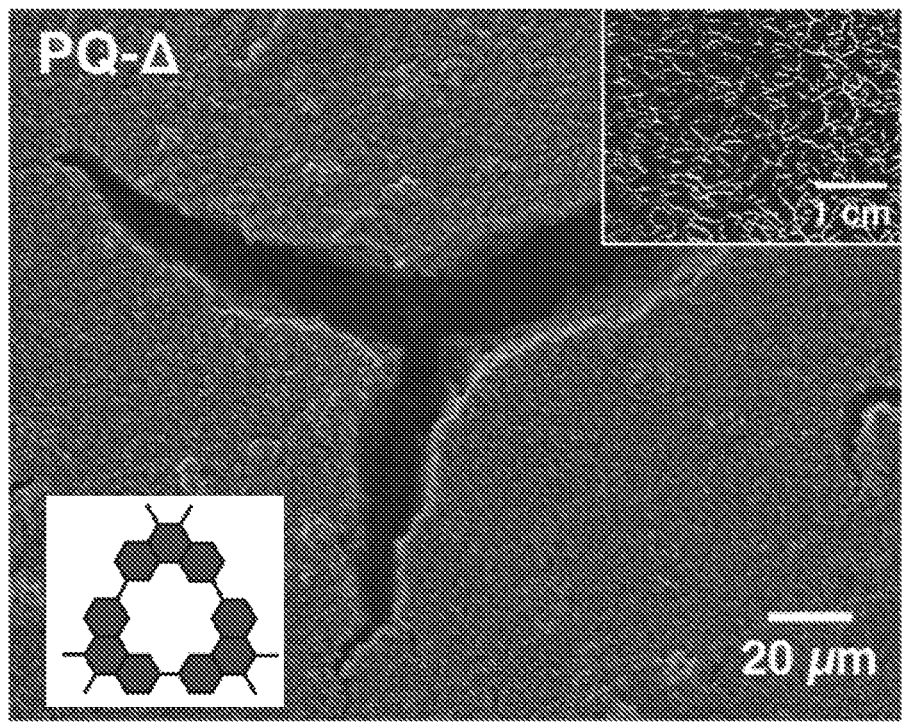
FIGS. 5A-5F show the mechanical stability and electrochemical performance of the hybrid electrode.
Figure 5B:
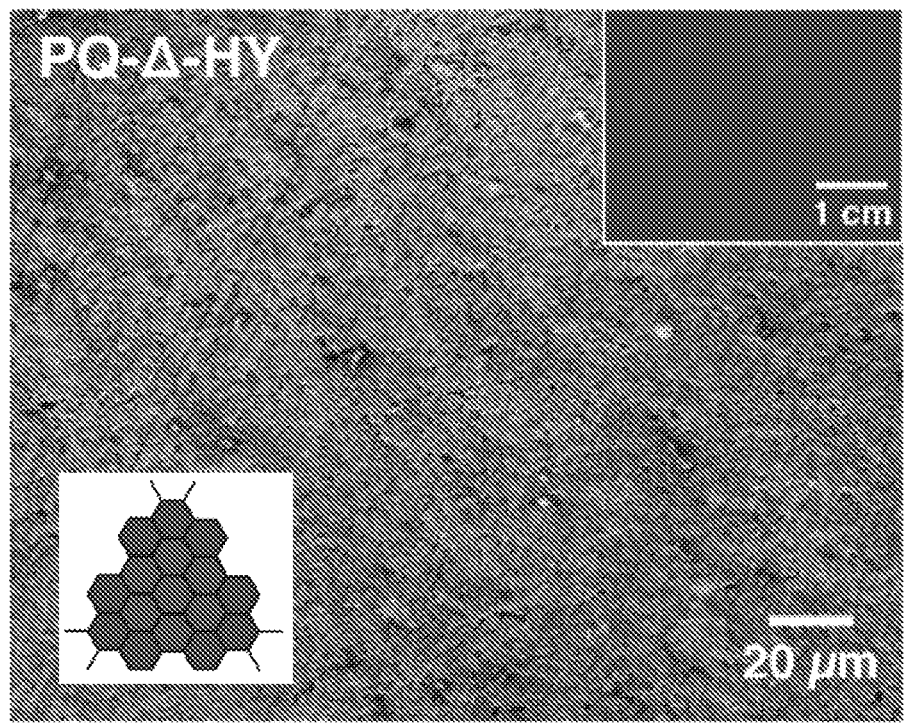
Figure 5C:
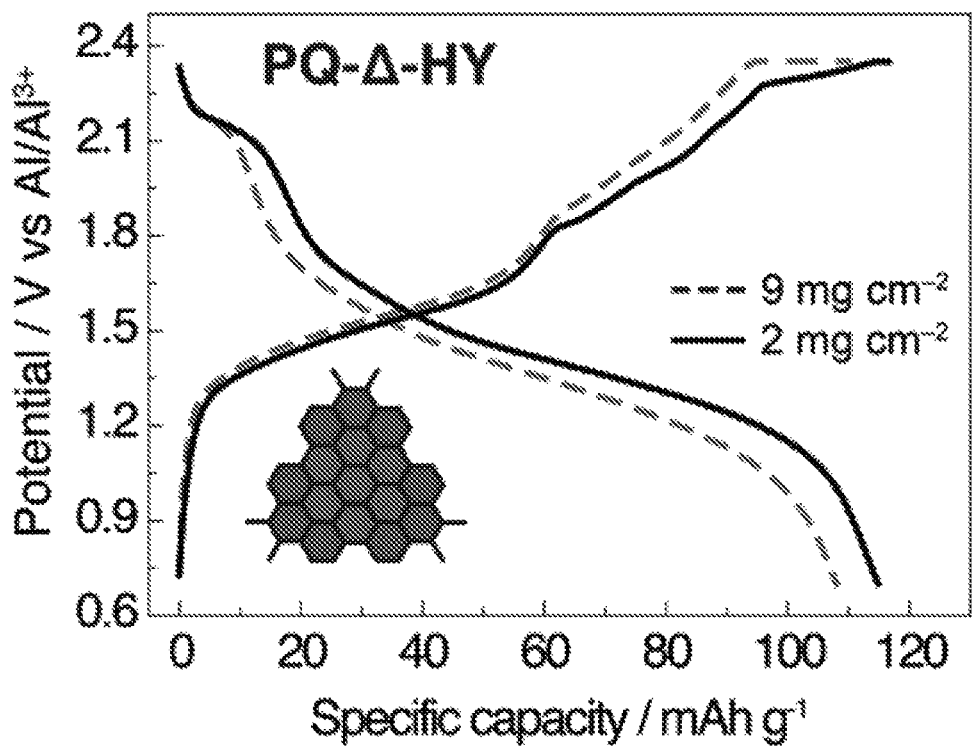
Figure 5D:
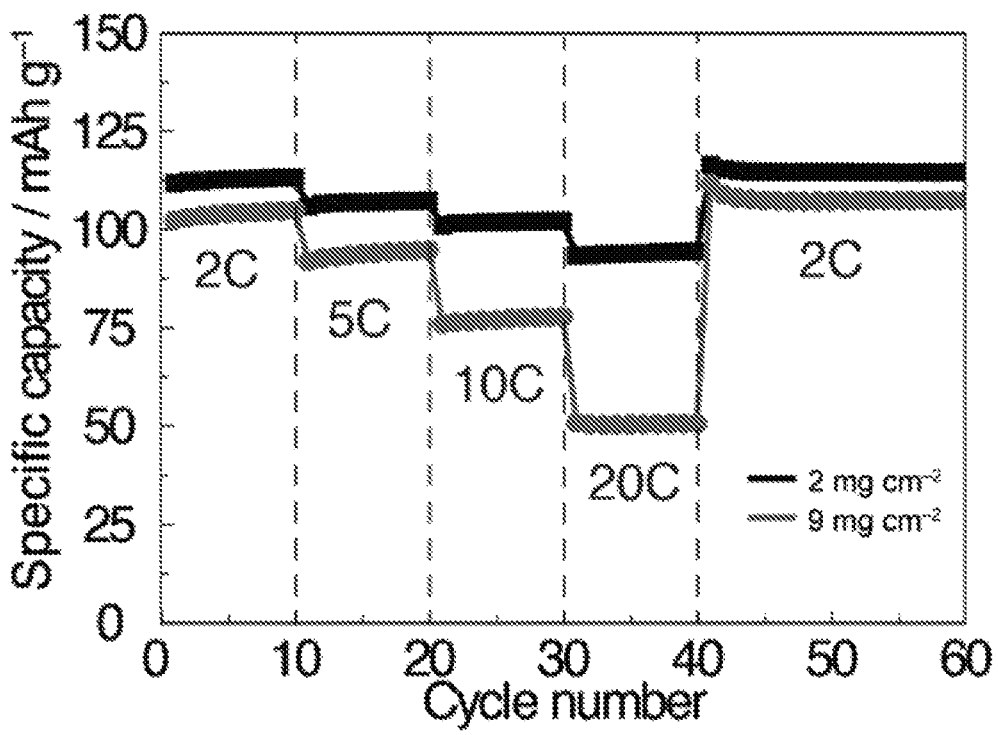
Figure 5E:
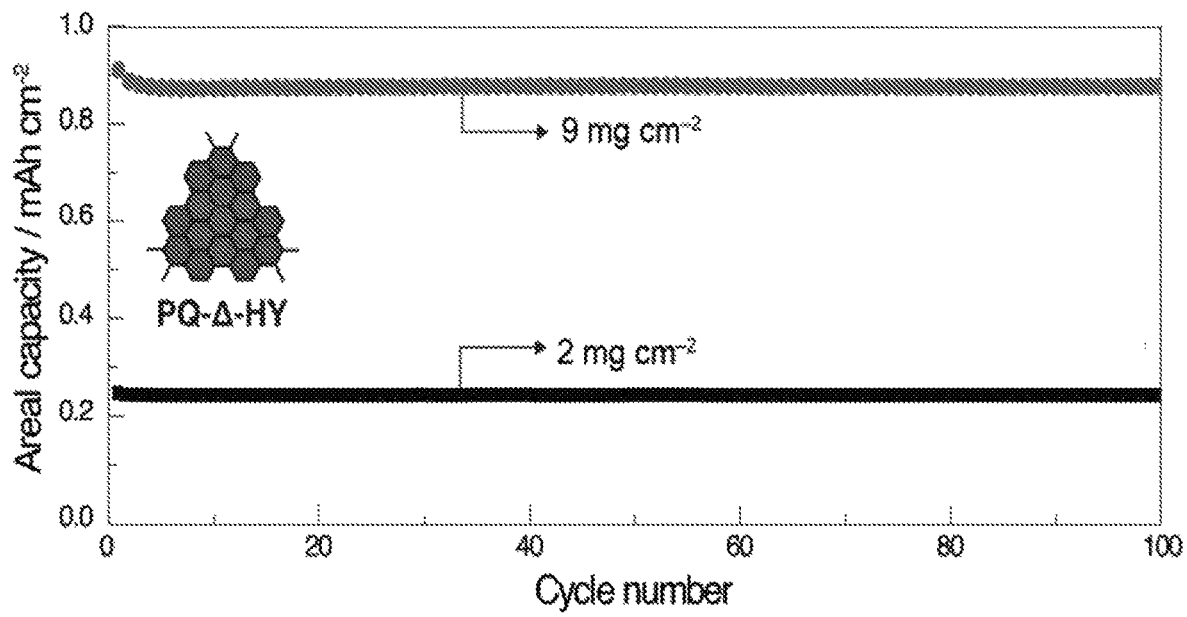
Figure 5F:
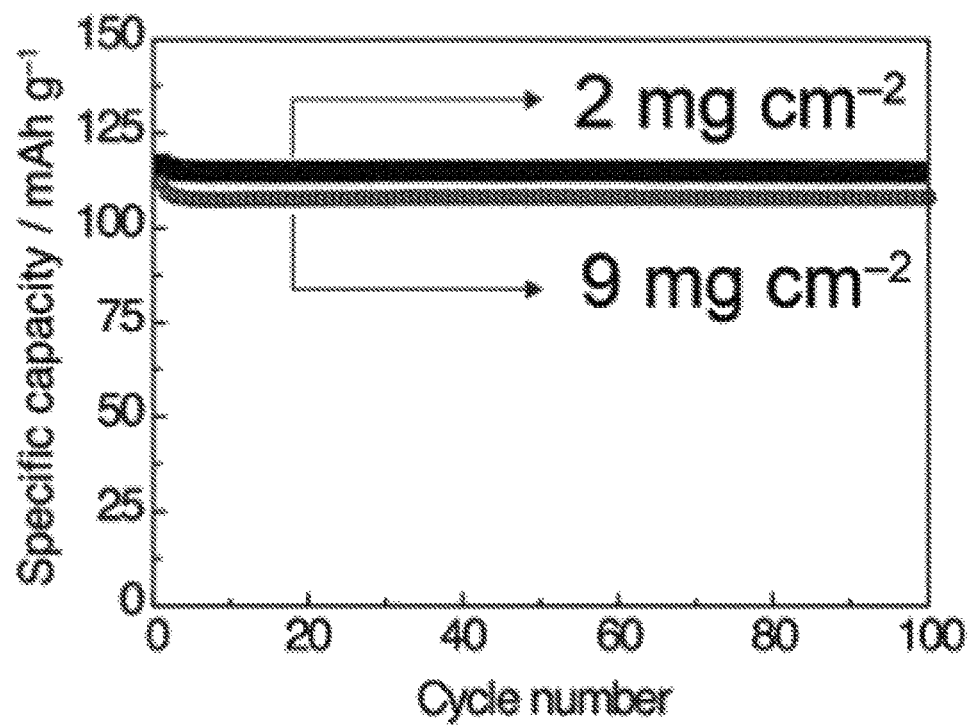
Figure 6:
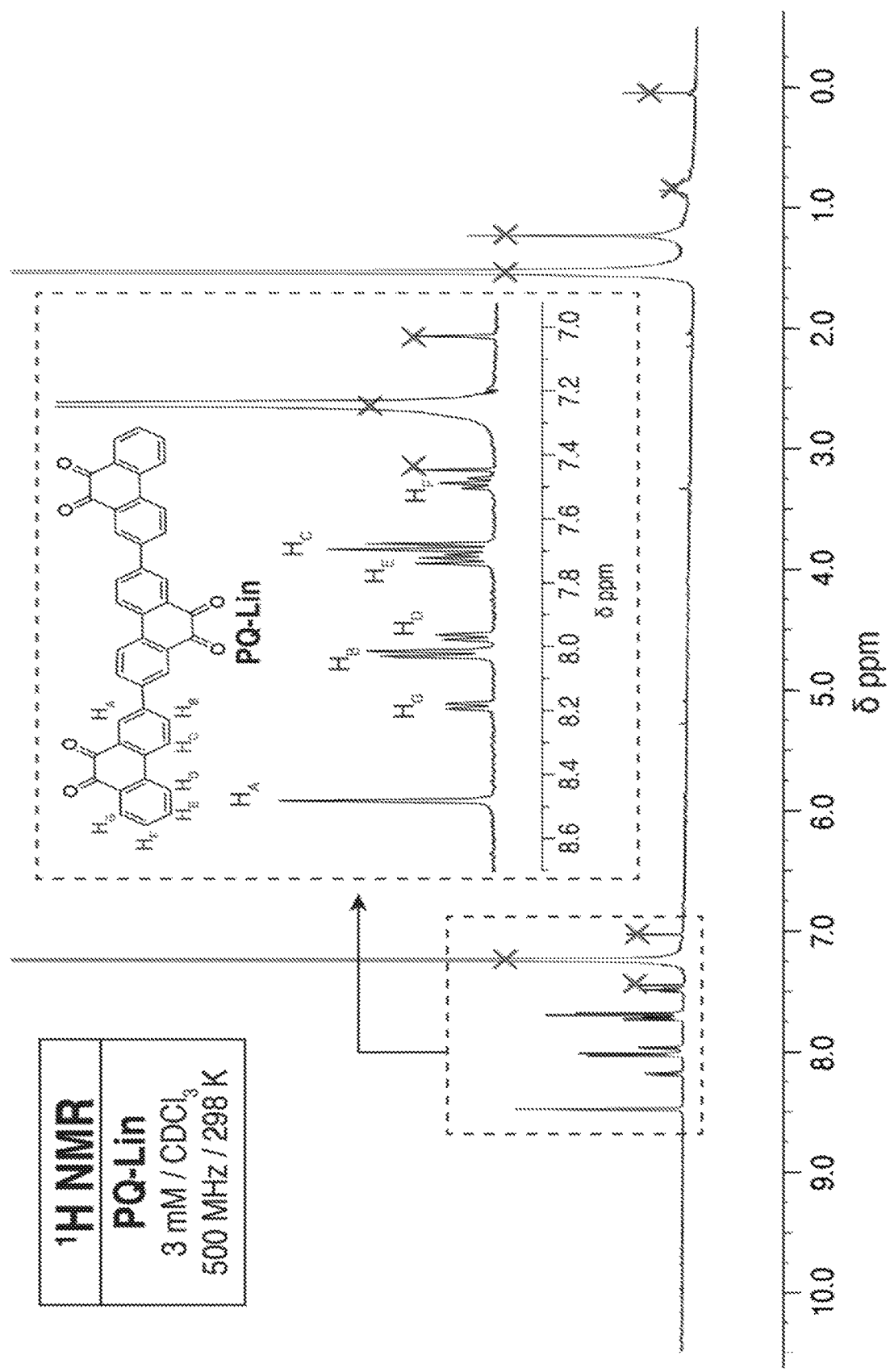
FIG. 6 shows the annotated 1H NMR spectra (500 MHZ, $CDCl_3$) PQ-Lin of compound.

One challenge with organic electrode materials lies in increasing substantially (i) their weight portion and (ii) the areal loading of the electrode. In order to appreciate the impact of the graphite integration in PQ-Δ-HY with respect to these aspects, we fabricated PQ-Δ and PQ-Δ-HY electrodes by means of a conventional casting process and checked their morphologies. In the case of PQ-Δ electrodes containing 50 wt % Denka black, the electrodes suffered from crack formation and peel-off during the drying process in the electrode fabrication, even at an active mass loading of 2 mg cm$^{-2}$, an observation which can be ascribed[42] to significant generation of stress in stacking PQ-Δ. This phenomenon can also be interpreted in a way that the stress is not well distributed (FIG. 5A) through conductive carbon fillers. With an increased portion of PQ-Δ (i.e., >40 wt %), the peeling issue of the electrode becomes more serious because of increased stress generation along the PQ-Δ stack[43, 44]. By contrast, even at an areal loading of 9 mg cm$^{-2}$, PQ-Δ-HY electrodes were able to maintain (FIG. 5B) their integrity by co-stacking of graphite flakes and PQ-Δ during the same drying process. With the areal loading of 9 mg cm$^{-2}$, PQ-Δ-HY electrode achieved (FIG. 5C) a capacity of 110 mAh g$^{-1}_{total}$ at 0.1 A g$^{-1}$. When the current rate was increased by 20 times (2 A g$^{-1}$) for this electrode, a specific capacity of 51 mAh g$^{-1}_{total}$ was still preserved, indicating (FIG. 5D) the excellent rate capability of PQ-Δ-HY electrodes. This rate performance can be attributed to the well distributed graphite in PQ-Δ-HY as a result of π-π interactions between PQ-Δ and graphite which facilitates efficient electron transport. PQ-Δ-HY electrodes with a loading of 9 mg cm$^{-2}$ also showed (FIG. 5E) good cyclability, as 96% (108 mAh g$^{-1}$) of the initial capacity was preserved after 100 cycles.

Energy Density Calculation

Unlike Li-ion batteries in which Li$^+$ ions are exclusively used as carrier ions, rechargeable aluminum batteries such as our case in which PQ-Δ serves as a cathode material require a different metric for energy density evaluation because the carrier ions of the anode (Al$^{3+}$) and the cathode (AlCl$_2^+$) are different. This condition equally leads to the fact that the amount of electrolyte for the storage of unit charge is different between the current rechargeable aluminum batteries and conventional Li-ion batteries. It is known[56] that total capacity in consideration of the amount of electrolyte can be calculated based on the following formula:

$$C_{total} = \frac{Fx(r-1)C_C}{Fx(r-1) + C_C(rM_{AlCl_3} + M_{EMIMCl})} \quad \text{(eqn 1)}$$

where F is Faraday constant, 26.8×103 mAh mol$^{-1}$, x=number of electrons used to reduce 1 mol of anodic material (i.e., AlCl$_3$), r is the AlCl$_3$/[EMIm]Cl molar ratio, Cc is the specific capacity of the cathode (mAh g$^{-1}$), $M_{AlCl3}$ is the molar mass of AlCl$_3$ (g mol$^{-1}$), and $M_{EMIMCl}$ is the molar mass of [EMIm]Cl or any other Cl$^-$ source (g mol$^{-1}$).

A cell that uses graphite as a cathode material operates based on the following reactions:

Anode:

$$AlCl_4^- + \frac{1}{3}Al \leftrightarrow \frac{4}{3}AlCl_3 + e^- \quad \text{(eqn 2)}$$

Cathode: $C_n[AlCl_4] + e^- \leftrightarrow C_n + AlCl_4^-$ (eqn 3)

Full-cell:

$$C_n[AlCl_4] + \frac{1}{3}Al^{3+} \leftrightarrow \frac{4}{3}AlCl_3 + C_n(1e^- \text{ reaction}), x = \frac{3}{4} \quad \text{(eqn 4)}$$

A cell that uses PQ-Δ as a cathode material operates based on the following reactions:

Anode: $3AlCl_4^- + Al \leftrightarrow 4AlCl_3 + 3e^-$ (eqn 5)

Cathode: PQ-Δ+6AlCl$_3$+3e$^-$↔PQ-Δ[3AlCl$_2$]+ 3AlCl$_4^-$ (eqn 6)

Full-cell:

$$PQ-\Delta + 2AlCl_3 + Al \leftrightarrow PQ-\Delta[3AlCl_2](3e^- \text{ reaction}), \quad \text{(eqn 7)}$$
$$x = \frac{3}{2}$$

In calculating the number of electrons used to reduce 1 mol of AlCl$_3$ (x in the formula), all Al$_2$Cl$_7^-$ ions are assumed to be replaced with AlCl$_4^-$+AlCl$_3$. According to the above reactions, x values for graphite and PQ-Δ are calculated to be 3/4 and 3/2, respectively, which means that PQ-Δ requires a smaller amount of electrolyte for the given charge storage. The energy density is obtained by multiplication of total capacity and operation voltage: E=C$_{total}$·V. When graphite and PQ-Δ are used as cathodes, the total capacities and energy densities are as follows:

With graphite cathode: C$_{total}$=21.9 mA/g, Energy density=40 Wh/kg (voltage=1.8V) (eqn 8)

With PQ-Δ cathode: C$_{total}$=38 mA/g, Energy density=54 Wh/kg (voltage=1.4V) (eqn 9)

The comparison of both properties reveals that when the amount of electrolyte is taken into consideration, organic cathode material that uses cationic charge carriers (thus acquires smaller amount of Cl$^-$ from the electrolyte to form Al-complex ion) can be more competitive in energy density compared to the case that uses anionic charge carriers (thus acquires larger amount of Cl$^-$ from the electrolyte to form Al-complex ion).

Conclusions

In summary, we have prepared phenanthrenequinone derivatives as active materials for emerging ALBs and explored their structure-performance relationships. While these compounds share similar redox potentials, we have observed that the triangular disposition of the redox-active units influences very strongly the accessibility of chloroaluminate ions, as well as the solubility of the triangular molecules. Most notably, the rigid triangular macrocycle increases the specific capacity and the cyclability dramatically, as a consequence of its layered architecture and the minimization of solvent effects. In addition, fabricating the hybrid electrode with graphite flakes overcomes significantly the inherently low electronic conductivity and limited areal loading of conventional organic electrodes, enabling the bipolar storage of anions and cations to increase the specific capacity.

Definitions

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C$_1$-C$_{12}$ alkyl, C$_1$-C$_{10}$-alkyl, and C$_1$-C$_6$-alkyl, respectively.

The term "alkylene" refers to a diradical of an alkyl group. An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as C$_2$-C$_{12}$-alkenyl, C$_2$-C$_{10}$-alkenyl, and C$_2$-C$_6$-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C$_2$-C$_{12}$-alkynyl, C$_2$-C$_{10}$-alkynyl, and C$_2$-C$_6$-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C$_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a C$_5$-C$_{14}$, C$_5$-C$_{12}$, C$_5$-C$_8$, or C$_5$-C$_6$ membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using Cx-Cx nomenclature where x is an integer specifying the number of ring atoms. For example, a C$_3$-C$_7$ heterocyclyl group refers to a saturated or partially unsaturated 3- to 7-membered ring structure containing one to four heteroatoms, such as nitrogen, oxygen, and sulfur. The designation "C$_3$-C$_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Examples

Materials preparation and characterization. Starting materials and reagents were purchased from commercial suppliers (Sigma Aldrich, Fisher Scientific or Tokyo Chemical Industry) and used without further purification. All reactions were performed under a nitrogen atmosphere, using anhydrous solvents unless otherwise stated. The crude reaction mixture was separated by silica gel column chromatography or on a Teledyne Isco Combiflash RF 200 system. Solution and solid-state nuclear magnetic resonance (NMR) spectra were recorded on Bruker Avance III 500 MHz and Varian VNMRS 400 MHz spectrometers, respectively, with working frequencies of 500 MHZ ($^1$H nuclei), 125 MHz ($^{13}$C nuclei), and 100 MHz ($^{13}$C CP MAS solid-state). All chemical shifts are reported in ppm with reference to deuterated chloroform (CDCl$_3$ $\delta_H$=7.26 and $\delta_C$=77.2 ppm). High-resolution mass spectra (HRMS) were performed on an Agilent 6210 Time of Flight (TOF) LC-MS, using an electrospray ionization (ESI) source. MALDI-TOF was carried out on a Bruker Autoflex III spectrometer using a 1:1 mixture of 2,5-dihydroxybenzoic acid and α-cyano-4-hydroxycinnamic acid as a matrix. Morphological changes in battery electrodes were characterized by field-emission scanning electron microscopy (FE-SEM, S-4800, Hitachi) and ultra-high resolution SEM (Magellan 400, FEI). Elemental mapping of electrode surfaces was carried out by energy-dispersive X-ray spectroscopy (EDS). Powder X-ray diffraction (PXRD) profiles of the phenanthrenequinones (PQ) were obtained using an X-ray diffractometer (SmartLab, Rigaku, Japan) based on Cu-Kα (λ=0.15406 nm) radiation. Thermogravimetric analysis (TGA, SDTA851, Mettler Toledo Instruments) was carried out from 25 to 800° C. at 10° ° C. min$^{-1}$, under nitrogen flow rate of 50 mL min$^{-1}$.

ex-situ Characterization of PQ-Δ electrodes. The Swagelok cells were disassembled in an argon-filled glovebox and the electrodes were washed with tetrahydrofuran. In order to remove PVDF binder and residual electrolyte, the electrode samples were sealed and sonicated in dimethoxyethane for 1 h, followed by drying under vacuum for 12 h. In order to avoid exposure to oxygen and moisture, a home-made gas-tight XRD holder was employed during XRD analyses. Field-emission TEM (FE-TEM, Tecnai) was used to identify changes in the layered superstructures of the charged and discharged PQ-Δ electrodes.

Preparation of electrodes and measurements. ALB electrodes were prepared according to the following procedures. PQ Derivatives, Denka black, and polyvinylidene fluoride (PVDF, Arkema) binder were dispersed in N-methyl-2-pyrrolidone (NMP) in a weight ratio of 3:5:2, respectively. The resultant slurry was then cast onto a tantalum foil (99.95%, Thermo Fisher) or pyrolytic graphite foil (MTI) which serve as current collectors. These casted electrodes were dried at 70° ° C. for 24 h under vacuum to remove residual NMP and the average electrode loading weight was found to be 0.5 mg cm$^{-2}$. PQ-Δ-HY was prepared by blending PQ-Ref or PQ-Δ with nano graphite flakes (N006, Digichem) according to the following procedure. Firstly, graphite (50 mg) was added to NMP (5 mL) and sonicated for 6 h, followed by addition of 50 mg of PQ-Ref or PQ-Δ: the mixture was dispersed for another 3 h. The solution was evaporated at 70° C. for 72 h under vacuum, yielding PQ-Δ-HY. Electrodes incorporating PQ-Δ-HY were fabricated using a composite of PQ-Δ-HY:Denka black:PVDF=8:1:1=w:w:w in which PQ-Δ and graphite were mixed in equal amounts by weight. The loading of active materials on PQ-Δ-HY electrodes was either 2 or 9 mg cm$^{-2}$. The ALB electrolyte was prepared inside the glovebox. Aluminum trichloride (AlCl$_3$) was added slowly to ethyl-3-methylimidazolium tetrachloroaluminate (EMImAlCl$_4$) in a molar ratio of 1.0 to 1.5, and then the mixture was stirred for a further 6 h, after which the electrolyte exhibited a light-yellowish color. The electrochemical measurements were conducted using a modified Swagelok-type cell, which was composed of the aluminum metal anode, a glass fiber membrane (GF/D, Whatman, USA), and the PQ derived cathode. The entire cell assembly process was carried out inside an argon-filled glovebox. All electrochemical measurements were performed using a battery cycler (MACCOR series 4000). CVs of PQ-based electrodes were performed at a rate of 5 mV s$^{-1}$ in the range of 0.8-1.75 V, while linear sweep voltammetry was performed from −0.7 to 3 V (vs Al/Al$^{3+}$) at a current rate of 1 mV s$^{-1}$ to confirm the electrochemical stability of the tantalum foil. Galvanostatic measurements were carried out after cycling 50 times by CV in order to activate PQ compounds. The rate performance was evaluated, based on a current density of 1 C=100 mA g$^{-1}$. In the case of PQ-Δ-HY, the CV was measured at a scan rate of 5 mV s$^{-1}$ in the range of 0.7-2.35 V. Furthermore, galvanostatic measurements were carried out at a current density of 1 C=100 mA g$^{-1}$ in the range of 0.7-2.35 V.

Synthetic Procedures
1) Synthesis of PQ-Δ

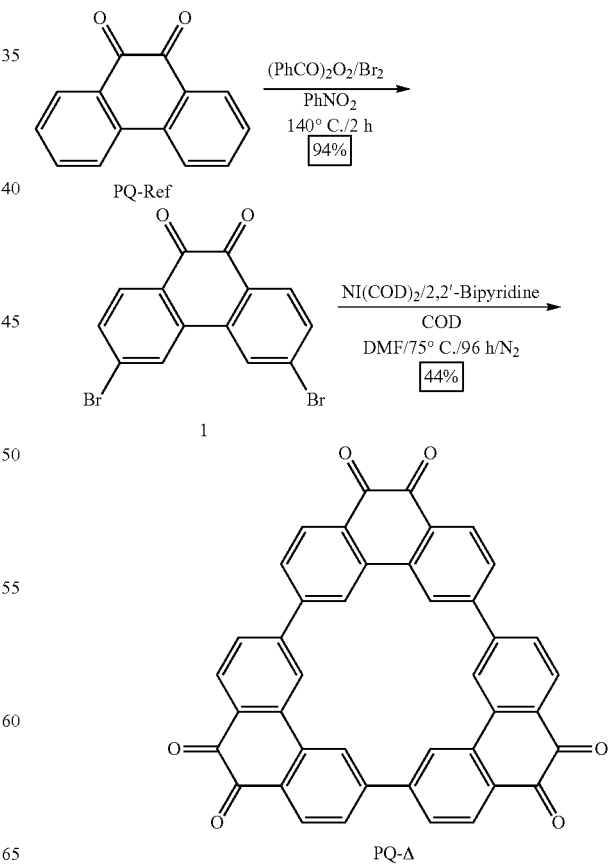

Synthesis Scheme 1|Synthesis of 3,6-dibromophenanthrenequinone and Phenanthrenequinone Triangle (PQ-Δ).

PQ-Ref was purchased from commercial vendor and used as it received. 1 and PQ-Δ were prepared from following synthetic procedures described in the literature[45]. 1: $^1$H NMR (500 MHZ, CDCl$_3$, 298 K) δ 8.10 (d, J=1.8 Hz, 2H), 8.06 (dd, J=8.3, 1.2 Hz, 2H), 7.65 (dd, J=8.4, 1.7 Hz, 2H); $^{13}$C NMR (125 MHz, CDCl$_3$, 298 K) δ 178.86, 135.94, 133.43, 132.10, 129.85, 127.40 ppm. PQ-Δ: $^{13}$C CP MAS solid-state NMR (400 MHZ, 298 K) δ=179.00, 146.26, 141.98, 135.34, 130.21 ppm.

2) Synthesis of Linear Phenanthrenequinone Trimer (PQ-Lin)

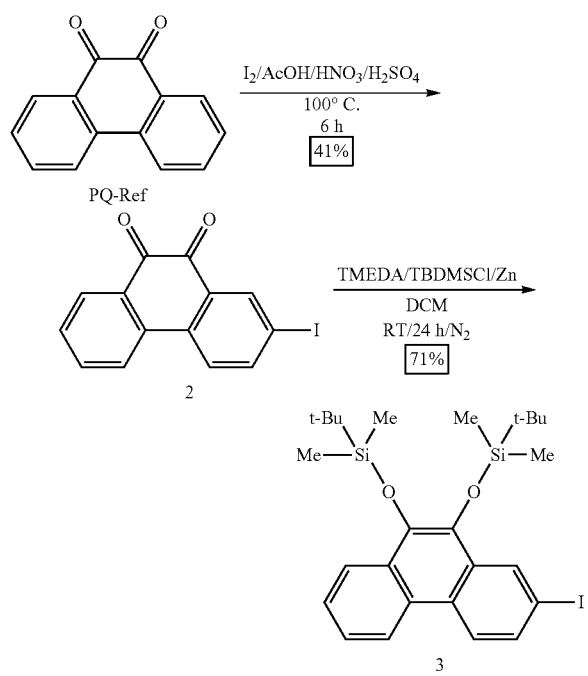

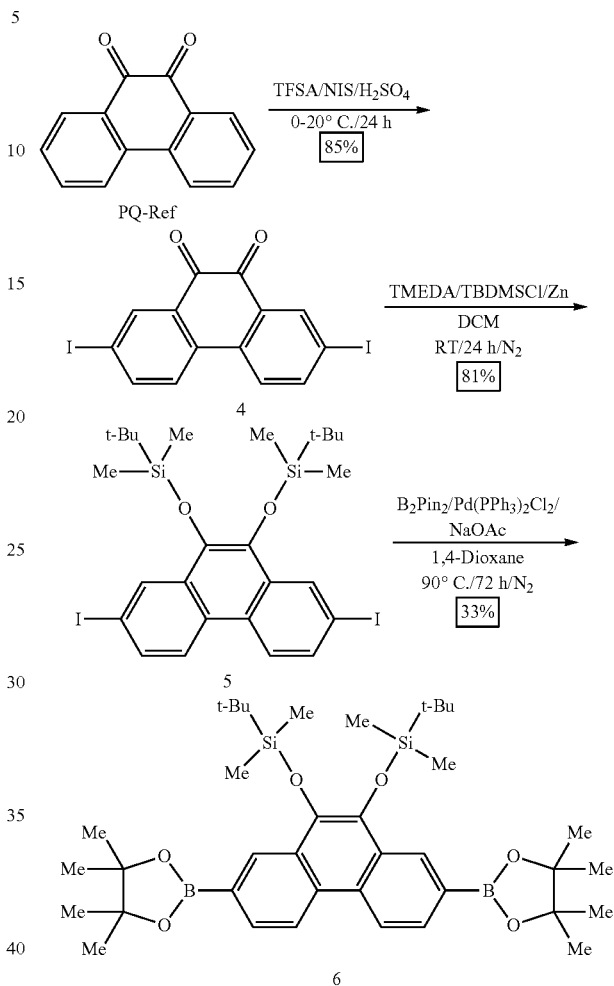

Synthesis Scheme 2|Synthesis of 2-iodo-9,10-dimethoxyphenanthrenequinone and 2-iodo-9,10-dimethoxyphenanthrenequinone.

2, 3, and 4 were prepared by following protocols described in previously reports[46, 47] in 41 and 71% yield, respectively. To a flask containing 2 (1.0 g, 3 mmol) in DCM (100 mL), N,N,N',N'-tetramethyl ethylenediamine (1.8 g, 15 mmol), t-butyl dimethyl chlorosilane (1.9 g, 12.6 mmol), and zinc powder (3 g) were added and stirred at room temperature for 36 hours. The crude product was washed through silica plug using ethyl acetate and further purified by column chromatography to yield 2.39 g of compound 4 (71%).

2: $^1$H NMR (500 MHz, CDCl$_3$, 298 K) δ 8.48 (t, J=1.6 Hz, 1H), 8.19 (dd, J=7.8, 1.5 Hz, 1H), 8.04-7.94 (m, 2H), 7.76-7.66 (m, 2H), 7.53-7.44 (m, 1H); $^{13}$C NMR (125 MHz, CDCl$_3$, 298 K) δ 179.38, 179.24, 144.78, 144.61, 139.14, 136.18, 135.19, 135.13, 132.00, 130.84, 130.06, 125.58, 123.92, 95.18 ppm. 3: $^1$H NMR (500 MHZ, CDCl$_3$) δ 8.56 (dd, J=3.2, 1.9 Hz, 1H), 8.52 (d, J=8.0 Hz, 1H), 8.25 (dd, J=32.8, 8.7 Hz, 1H), 8.20-8.15 (m, 1H), 7.77 (dt, J=8.7, 2.5 Hz, 1H), 7.61-7.49 (m, 2H), 1.15-1.10 (m, 18H), 0.07 (d, J=2.9 Hz, 12H); $^{13}$C NMR (125 MHZ, CDCl$_3$, 298 K) δ 137.80, 137.02, 135.88, 132.84, 131.62, 131.58, 130.04, 129.98, 127.31, 126.95, 126.29, 126.09, 125.58, 124.84, 124.46, 123.76, 122.76, 122.64, 121.99, 121.85, 91.48, 26.18, 26.14, 26.10, 26.06, 18.39, -3.82 ppm. HRMS (ESI) m z=564.1376 [M$^+$], calcd. for [C$_{26}$H$_{37}$IO$_2$Si$_2$] 564.1371.

Synthesis Scheme 3|Synthesis of 3,6-diiodophenanthrenequinone, 2,7-diiodo-9,10-bis(tert-butyldimethylsiloxy)phenanthrene and 2,2'-bis(tert-butyldimethylsiloxy)-bis(4,4,5,5-tetramethyl-1,3,2-dioxaborolane).

4, 5, and 6 were prepared by following or modifying previously reported procedure[46, 48, 49]. Prepared 5 (1.50 g, 2.15 mmol) was dissolved in 100 mL of 1,4-dioxane, followed by adding bispinacol diboron (1.32 g, 5.16 mmol), bis(triphenylphosphine)palladium(II) dichloride (0.23 g, 0.32 mmol), and sodium acetate (0.71 g, 8.6 mmol). The mixture was stirred at 90° C. for 72 hours. The crude mixture was filtered through celite and purified by column chromatography (hexane/ethyl acetate), affording compound 6.

4: $^1$H NMR (500 MHz, CDCl$_3$, 298 K) δ 8.48 (d, J=2.0 Hz, 2H), 8.02 (dd, J=8.4, 2.0 Hz, 2H), 7.69 (d, J=8.5 Hz, 2H). 13C NMR (125 MHz, CDCl$_3$, 298 K) δ 144.77, 139.43, 134.42, 125.43, 95.71 ppm. 5: $^1$H NMR (500 MHz, CDCl$_3$, 298 K) δ 8.56 (d, J=1.9 Hz, 2H), 8.22 (d, J=8.7 Hz, 2H), 7.77 (dd, J=8.7, 1.9 Hz, 2H), 1.13 (s, 18H), 0.07 (s, 12H); $^{13}$C NMR (125 MHZ, CDCl$_3$, 298 K) δ 133.61, 132.13, 123.91, 92.34, 26.42, 18.75, -3.49 ppm. 6: $^1$H NMR (500 MHZ, CDCl$_3$, 298 K) δ 8.56 (d, J=1.9 Hz, 2H), 8.22 (d, J=8.8 Hz, 2H), 7.77 (dd, J=8.6, 1.9 Hz, 2H), 1.19-1.05 (m, 24H), 0.90 (s, 18H), 0.08 (s, 12H).

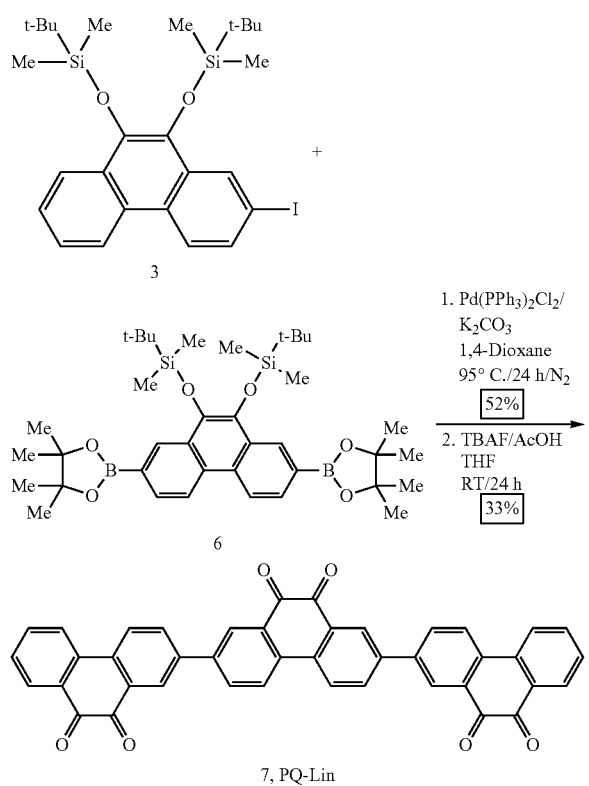

Synthesis Scheme 4|Synthesis of PQ-Lin Through Suzuki Coupling.

PQ-Lin-TBS and PQ-Lin were prepared following previous references[47]. 7: Prepared 4 (0.5 g, 0.75 mmol) and 6 (1.23 g, 2.17 mmol) compounds were dissolved in 150 mL of 1,4-dioxane, followed by adding bis(triphenylphosphine) palladium(II) dichloride (0.41 g, 0.58 mmol) and potassium acetate (0.1 g, 0.72 mmol). The mixture was stirred at 95° C. for 24 hours and filtered through celite. The crude mixture was purified by column chromatography (hexane/ethyl acetate). The TBS protected linear trimer fraction (0.1 g) was dissolved in THF (10 mL) and tetrabutylammonium fluoride (2.3 mL) and acetic acid (64 µL) were added to a solution of the linear trimer. The mixture was stirred at ambient temperature for overnight. After the reaction, the crude mixture was filtered through celite and purified by column chromatography (hexane/ethyl acetate).

7, PQ-Lin: $^1$H NMR (500 MHZ, CDCl$_3$ 298 K) δ 8.50-8.46 (m, 4H), 8.19 (dd, J=7.8, 1.5 Hz, 2H), 8.02 (dt, J=8.4, 1.9 Hz, 5H), 7.97 (d, J=8.1 Hz, 1H), 7.74-7.67 (m, 6H), 7.49 (td, J=7.7, 1.1 Hz, 2H); $^{13}$C NMR (125 MHz, CDCl$_3$, 298 K) δ 144.77, 139.43, 139.14, 136.18, 130.84, 125.42 ppm.

REFERENCES

1. Huggins R. *Advanced batteries: Materials science aspects*. Springer Science & Business Media, 2008.
2. Dunn B., Kamath H. & Tarascon J.-M. Electrical energy storage for the grid: A battery of choices. *Science* 334, 928-935 (2011).
3 Chu S., Cui Y. & Liu N. The path towards sustainable energy. *Nat. Mater.* 16, 16-22 (2017).
4. Tarascon J.-M. & Armand M. Issues and challenges facing rechargeable lithium batteries. *Nature* 414, 359-367 (2001).
5. Goodenough J. B. & Park K.-S. The Li-ion rechargeable battery: A perspective. *J. Am. Chem. Soc.* 135, 1167-1176 (2013).
6. Choi J. W. & Aurbach D. Promise and reality of post-lithium-ion batteries with high energy densities. *Nat. Rev. Mater.* 1, 16013 (2016).
7. Armand M. & Tarascon J.-M. Building better batteries. *Nature* 451, 652-657 (2008).
8. Elia G. A., et al. An overview and future perspectives of aluminum batteries. *Adv. Mater.* 28, 7564-7579 (2016).
9. Li Q. & Bjerrum N. J. Aluminum as anode for energy storage and conversion: A review. *J. Power Sources* 110, 1-10 (2002).
10. Canepa P., et al. Odyssey of multivalent cathode materials: Open questions and future challenges. *Chem. Rev.* 117, 4287-4341 (2017).
11. Muldoon J., Bucur C. B. & Gregory T. Quest for nonaqueous multivalent secondary batteries: Magnesium and beyond. *Chem. Rev* 114, 11683-11720 (2014).
12. Yoo D.-J., Kim J.-S., Shin J., Kim K. J. & Choi J. W. Stable performance of aluminum metal battery by incorporating lithium ion chemistry. *ChemElectroChem* 4, 2345-2351 (2017).
13. Dagorne S. & Atwood D. A. Synthesis, characterization, and applications of group 13 cationic compounds. *Chem. Rev.* 108, 4037-4071 (2008).
14. Atwood D. A. Cationic group 13 complexes. *Coord. Chem. Rev.* 176, 407-430 (1998).
15. Buchanan R. M. & Pierpont C. G. Tautomeric catecholate-semiquinone interconversion via metal-ligand electron-transfer—structural, spectral, and magnetic-properties of (3,5-di-tert-butylcatecholato)-(3,5-di-tert-butylsemiquinone)(bipyridyl)cobalt(III), a complex containing mixed-valence organic-ligands. *J. Am. Chem. Soc.* 102, 4951-4957 (1980).
16. Piskunov* A. V., Maleeva A. V., Fukin G. K., Baranov E. V. & Kuznetsova O. V. Quinone complexes of aluminum: Synthesis and structures. *Russ. J. Coord. Chem.* 36, 161-169 (2010).
17. Connelly N. G. & Geiger W. E. Chemical redox agents for organometallic chemistry. *Chem. Rev.* 96, 877-910 (1996).
18. Klimov E. S., Lobanov A. V. & Abakumov G. A. Electron-spin-resonance spectra of chelate complexes of 1,2-naphthoquinone and 9,10-phenanthrenequinone with halides of group-III elements. *Russ. Chem. Bull.* 30, 1664-1666 (1981).
19. Barker P. E., Hudson A. & Jackson R. A. The reaction of aluminium trichloride with 9,10-phenanthrenequinone. *J. Organomet. Chem.* 208, C1-C2 (1981).
20. Aurbach D., et al. Prototype systems for rechargeable magnesium batteries. *Nature* 407, 724-727 (2000).
21. Hudak N. S. Chloroaluminate-doped conducting polymers as positive electrodes in rechargeable aluminum batteries. *J. Phys. Chem. C* 118, 5203-5215 (2014).
22. Jayaprakash N., Das S. K. & Archer L. A. The rechargeable aluminum-ion battery. *Chem. Commun.* 47, 12610-12612 (2011).
23. Zhang J., et al. Metal-free phenanthrenequinone cyclotrimer as an effective heterogeneous catalyst. *J. Am. Chem. Soc.* 131, 11296-11297 (2009).
24. Ohtsuka Y., Yoshida J. & Nokami T., inventors; Panasonic Corporation, assignee. Phenanthrenequinone compound, electrode active material, and power storage device patent U.S. Ser. No. 12/530,382. 2008.

25. Tang L., et al. Preparation, structure, and electrochemical properties of reduced graphene sheet films. *Adv. Funct. Mater.* 19, 2782-2789 (2009).
26. Geim A. K. & Novoselov K. S. The rise of graphene. *Nat. Mater.* 6, 183-191 (2007).
27. Schwab M. G., et al. Torands revisited: Metal sequestration and self-assembly of cyclo-2,9-tris-1,10-phenanthroline hexaaza macrocycles. *Chem. Eur. J.* 21, 8426-8434 (2015).
28. Lin M.-C., et al. An ultrafast rechargeable aluminium-ion battery. *Nature* 520, 324-328 (2015).
29. Hassan F. M., et al. Evidence of covalent synergy in silicon-sulfur-graphene yielding highly efficient and long-life lithium-ion batteries. *Nat. Commun.* 6, 8597 (2015).
30. Kaim W. Radical-forming electron-transfer reactions involving main-group organometallics. *Acc. Chem. Res.* 18, 160-166 (1985).
31. Koten G. V., Jastrzebski J. T. B. H. & KeesVrieze. Stable 1,4-diaza-1,3-butadiene($\alpha$-diimine)-zinc and -aluminium radicals formed in single electron transfer reactions: Their consequences for organic syntheses. *J. Organomet. Chem.* 250, 49-61 (1983).
32. Razuvaev G. A., Abakumov G. A., Klimov E. S., Gladyshev E. N. & Bayushkin P. Y. Reactions of sterically hindered o-quinones with alkyl derivatives of group III elements. *Russ. Chem. Bull.* 26, 1034-1037 (1977).
33. Kravchyk K. V., Wang S., Piveteau L. & Kovalenko M. V. Efficient aluminum chloride-natural graphite battery. *Chem. Mater.* 29, 4484-4492 (2017).
34. Kim D. J., et al. Redox-active macrocycles for organic rechargeable batteries. *J. Am. Chem. Soc.* 139, 6635-6643 (2017).
35. Armand M., et al. Conjugated dicarboxylate anodes for Li-ion batteries. *Nat. Mater.* 8, 120-125 (2009).
36. Morita Y., et al. Organic tailored batteries materials using stable open-shell molecules with degenerate frontier orbitals. *Nat. Mater.* 10, 947-951 (2011).
37. Lee M., et al. Organic nanohybrids for fast and sustainable energy storage. *Adv. Mater.* 26, 2558-2565 (2014).
38. Liang Y., Tao Z. & Chen J. Organic electrode materials for rechargeable lithium batteries. *Adv. Energy. Mater.* 2, 742-769 (2012).
39. Zhang Z., Yoshikawa H. & Awaga K. Discovery of a "bipolar charging" mechanism in the solid-state electrochemical process of a flexible metal-organic framework. *Chem. Mater.* 28, 1298-1303 (2016).
40. Fang C., et al. A metal-organic compound as cathode material with superhigh capacity achieved by reversible cationic and anionic redox chemistry for high-energy sodium-ion batteries. *Angew. Chem. Int. Ed.* 129, 6897-6901 (2017).
41. Wang D.-Y., et al. Advanced rechargeable aluminium ion battery with a high-quality natural graphite cathode. *Nat. Commun.* 8, 14283 (2017).
42. Chen C. J., et al. Highly conductive, lightweight, low-tortuosity carbon frameworks as ultrathick 3D current collectors. *Adv. Energy. Mater.* 7, 1700595 (2017).
43. Lee J. H., et al. Restacking-inhibited 3d reduced graphene oxide for high performance supercapacitor electrodes. *Acs Nano* 7, 9366-9374 (2013).
44. Wu K. H., Wang D. W. & Gentle I. R. The value of mixed conduction for oxygen electroreduction on graphene-chitosan composites. *Carbon* 73, 234-243 (2014).
45. Zhang J., et al. Metal-free phenanthrenequinone cyclotrimer as an effective heterogeneous catalyst. *J. Am. Chem. Soc.* 131, 11296-11297 (2009).
46. Chaudhuri D., et al. Tuning the singlet triplet gap in metal-free phosphorescent $\pi$-conjugated polymers. *Angew. Chem. Int. Ed.* 49, 7714-7717 (2010).
47. Ohtsuka Y., Yoshida J. & Nokami T., inventors; Panasonic Corporation, assignee. Phenanthrenequinone compound, electrode active material, and power storage device patent U.S. Ser. No. 12/530,382. 2008.
48. Ciszek J. W. & Tour J. M. Synthesis of ladder polyaromatics as new molecular device candidates. *Tetrahedron Lett.* 45, 2801-2803 (2004).
49. Kim Y. A., et al. Structure-property relationship of D-A type copolymers based on phenanthrene and naphthalene units for organic electronics. *J Mater Chem C* 5, 10332-10342 (2017).
50. Kravchyk K. V., Wang S., Piveteau L. & Kovalenko M. V. Efficient aluminum chloride-natural graphite battery. *Chem. Mater.* 29, 4484-4492 (2017).

We claim:

1. A cathodic material comprising a macrocycle comprising a substituted or unsubstituted phenanthrenequinone unit and a graphite flake, wherein the macrocycle comprises three substituted or unsubstituted phenanthrenequinone units in a triangular arrangement.

2. The cathodic material of claim 1, wherein the substituted or unsubstituted phenanthrenequinone unit comprises

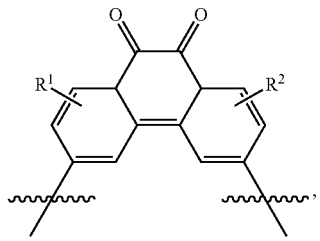

wherein $R^1$ and $R^2$ are independently selected from hydrogen, halogen, azide, alkyl, aralkyl, alkenyl, alkynyl, cycloalkyl, hydroxyl, alkoxyl, amino, nitro, imino, amido, carbonyl, —C(O)alkyl, carboxy, —CO$_2$alkyl, alkylthio, sulfonyl, sulfonamido, sulfhydryl, sulfonamide, heterocyclyl, aryl, heteroaryl moieties, —CF$_3$, or —CN.

3. The cathodic material of claim 2, wherein the macrocycle comprises a compound of formula

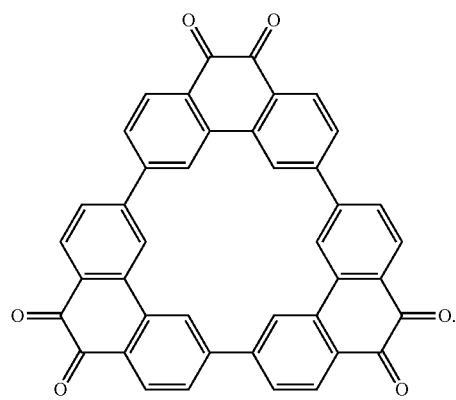 [SMILES: O=c1c(=O)c2ccc3cc2c2cc(ccc12)c1ccc2c(=O)c(=O)c4ccc(cc4c2c1)c1ccc2c(=O)c(=O)c4ccc3cc4c2c1]

4. The cathodic material of claim 1, wherein the macrocycle comprises a cationic aluminum complex.

5. The cathodic material of claim 4, wherein the macrocycle comprises three substituted or unsubstituted phenanthrenequinone units in a triangular arrangement and each of the phenanthrenequinone units chelate a cationic aluminum center.

6. The cathodic material of claim 4, wherein the substituted or unsubstituted phenanthrenequinone unit comprises

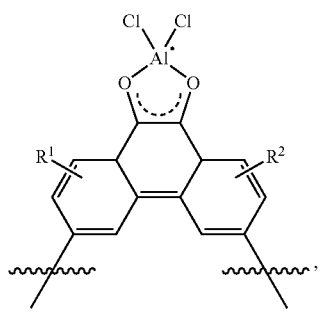

wherein $R^1$ and $R^2$ are independently selected from hydrogen, halogen, azide, alkyl, aralkyl, alkenyl, alkynyl, cycloalkyl, hydroxyl, alkoxyl, amino, nitro, imino, amido, carbonyl, —C(O)alkyl, carboxy, —$CO_2$alkyl, alkylthio, sulfonyl, sulfonamido, sulfhydryl, sulfonamide, heterocyclyl, aryl, heteroaryl, —$CF_3$, or —CN.

7. The cathodic material of claim 6, wherein the macrocycle comprises the cationic aluminum complex of formula

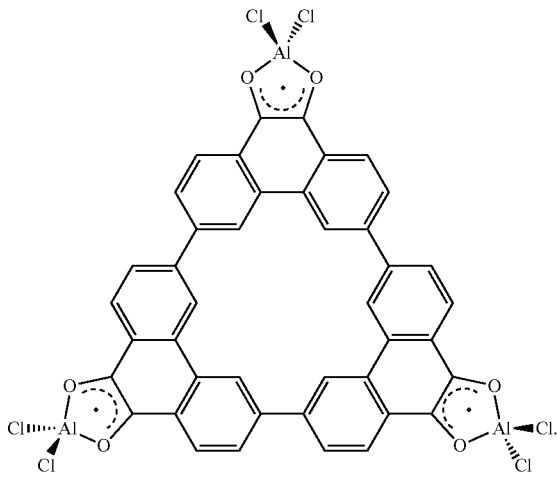

8. The cathodic material of claim 1, wherein the macrocycle is planar.

9. The cathodic material of claim 1, wherein the cathodic material comprises between about 2.0:1.0 and about 1.0:2.0 of the macrocycle to the graphite flake by weight.

10. The cathodic material of claim 1, wherein the cathodic material further comprises an electron-conducting additive.

11. The cathodic material of claim 10, wherein the electron-conducting additive is acetylene black.

12. The cathodic material of claim 1, wherein the cathodic material comprises a binder material.

13. An electrode comprising the cathodic material of claim 1 and a substrate.

14. A battery comprising a cathode, the cathode comprising the cathodic material of claim 1 and an electrolyte.

15. The battery of claim 14, wherein the electrolyte comprises an aluminum halide.

16. The battery of claim 15, wherein the electrolyte comprises tetetrachloroaluminate.

17. The battery of claim 14, wherein the electrolyte comprises an imidazolium.

18. The battery of claim 17, wherein the electrolyte comprises ethyl-3-methylimidazolium.

19. The battery of claim 14 further comprising an anode, the anode comprising aluminum or an aluminum-based active material.

* * * * *